(12) United States Patent
Nemoto et al.

(10) Patent No.: US 11,634,705 B2
(45) Date of Patent: Apr. 25, 2023

(54) HIGH-SPEED IN VITRO SCREENING METHOD

(71) Applicant: EPSILON MOLECULAR ENGINEERING INC., Saitama (JP)

(72) Inventors: Naoto Nemoto, Saitama (JP); Toshiki Miyajima, Saitama (JP); Yuta Matsukawa, Saitama (JP)

(73) Assignee: EPSILON MOLECULAR ENGINEERING INC., Saitama (JP)

( * ) Notice: Subject to any disclaimer, the term of this patent is extended or adjusted under 35 U.S.C. 154(b) by 419 days.

(21) Appl. No.: 17/025,954

(22) Filed: Sep. 18, 2020

(65) Prior Publication Data
US 2021/0079381 A1   Mar. 18, 2021

Related U.S. Application Data

(63) Continuation-in-part of application No. 16/145,292, filed on Sep. 28, 2018, now Pat. No. 10,781,442.
(Continued)

(30) Foreign Application Priority Data

Mar. 30, 2016   (JP) .............................. JP2016-069064

(51) Int. Cl.
*C40B 30/04* (2006.01)
*C12N 15/10* (2006.01)

(52) U.S. Cl.
CPC ..... *C12N 15/1048* (2013.01); *C12N 15/1062* (2013.01); *C40B 30/04* (2013.01)

(58) Field of Classification Search
None
See application file for complete search history.

(56) References Cited

U.S. PATENT DOCUMENTS 6,699,658 B1    3/2004 Wittrup et al.
2005/0038229 A1 2/2005 Lipovsek et al.
(Continued)

FOREIGN PATENT DOCUMENTS

JP   2006-211984 A   8/2006
JP   2009-124946 A   6/2009
(Continued)

OTHER PUBLICATIONS

Feldhaus, Michael J., et al., "Flow-cytometric isolation of human antibodies from a nonimmune *Saccharomyces cerevisiae* surgace display library," Nature Biotech, vol. 21 (2003), pp. 163-170.
(Continued)

*Primary Examiner* — Christian C Boesen
(74) *Attorney, Agent, or Firm* — Faegre Drinker Biddle & Reath LLP

(57) ABSTRACT

The purpose of the present invention is to provide a method for identifying antibody CDR3 clusters using high speed in vitro screening a library selected from the group consisting of cDNA library and nucleic acid aptamer library comprising: (i) preparing a positive spherical shaped structure by binding a target molecule to a spherical shaped molecule, wherein the target molecule is immobilized on the positive spherical shaped structure, wherein the positive spherical shaped structure may contain a fluorescent label; (ii) preparing a negative spherical shaped structure, wherein the target molecule is not immobilized on the negative spherical shaped structure, wherein the negative spherical shaped structure may contain a fluorescent label; (iii) forming a positive spherical shaped conjugate or a negative spherical shaped conjugate by binding a target detecting molecule capable of binding to the target molecule to the positive spherical shaped structure or to the negative spherical structure, wherein the target detecting molecule is selected from
(Continued)

the library having a size equal to or more than $10^{10}$ or equal to or less than $10^{14}$, wherein the target detecting molecule may contain a fluorescent label; (iv) separating the positive and the negative spherical shaped conjugates using a fluorescence cell sorter; (v) selecting the separated positive and the separated negative spherical shaped conjugates at least 1 time and then eluting the selected conjugates to obtain an eluted sample; (vi) amplifying a nucleic acid in the eluted sample using PCR to obtain PCR products; (vii) separating the PCR products using the fluorescence cell sorter; and (viii) conducting amplicon sequencing for CDR3 cluster analysis to identify the antibody CDR3 clusters.

9 Claims, 26 Drawing Sheets

Specification includes a Sequence Listing.

Related U.S. Application Data which is a continuation of application No. PCT/JP2017/013076, filed on Mar. 29, 2017.

(56) References Cited

U.S. PATENT DOCUMENTS

| | | |
|---|---|---|
| 2010/0267585 A1 | 10/2010 | Terbrueggen |
| 2014/0234218 A1 | 8/2014 | Christ et al. |
| 2016/0237119 A1 | 8/2016 | Suga et al. |

FOREIGN PATENT DOCUMENTS

| | | |
|---|---|---|
| JP | 2010-6745 A | 1/2010 |
| JP | 2011-55770 A | 3/2011 |
| JP | 2011-512841 A | 4/2011 |
| JP | 2012-531887 A | 12/2012 |
| JP | 2014-515749 A | 7/2014 |
| JP | 2015-51023 A | 3/2015 |
| JP | 2016-2041 A | 1/2016 |
| WO | WO-2009/114093 A2 | 9/2009 |
| WO | WO-2015/056713 A1 | 4/2015 |

OTHER PUBLICATIONS

Hamada, Eri, et al., "Development of high-speed screening system for peptide aptamer by using FACS," Poster, Exhibition Hall; 16:15 to 17:30, Dec. 2 (Fri), 2016, 2 pages.

Mochizuki, Yuki, et al., "A versatile puromycin-linker using cnvK for high-throughput in vitro selection by cDNA display," Journal of Biotechnology, 212 (2015), pp. 174-180.

Srisawat, Chatchawan, et al.,"Streptavidin aptamers: Affinity tages for the study of RNAs and ribonucleoproteins," RNA (2001), 7:632-641.

Kagaku to Seibutsu, vol. 40, No. 4 (2002), pp. 251-257.

Yamaguchi, Junichi, et al., "cDNA display: a novel screening method for functional disulfide-rich peptides by solid-phase synthesis and stabilization of mRNA-protein fusions," Nucleic Acids Research, 2009, vol. 37, No. 16, 2009, 13 pages.

Yanagawa, Hiroshi, et al., "Development of IVV method into drug discovery," Drug Delivery System, 2011, vol. 26, No. 6, pp. 571-583.

News Release, NEDO, New Energy and Industrial Technology Development Organization, Sep. 2, 2013, http://www.nedo.go.jp/news/press/AA5_100222.html, 8 pages, including partial English language translation.

English translation of International Preliminary Report on Patentability dated Jul. 27, 2018, for PCT/JP2017/013076.

International Search Report and Written Opinion dated Jul. 4, 2017, for PCT/JP2017013076.

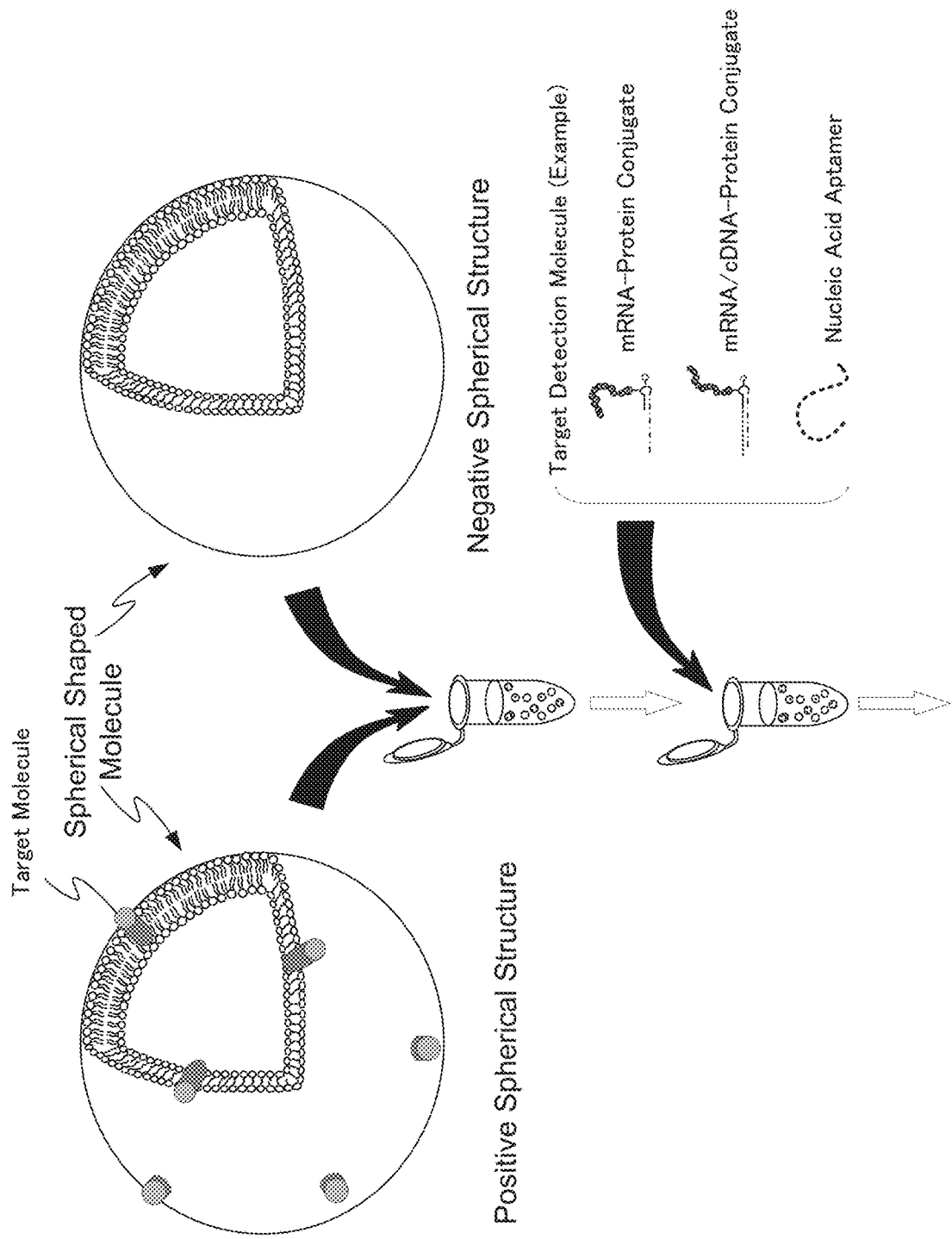

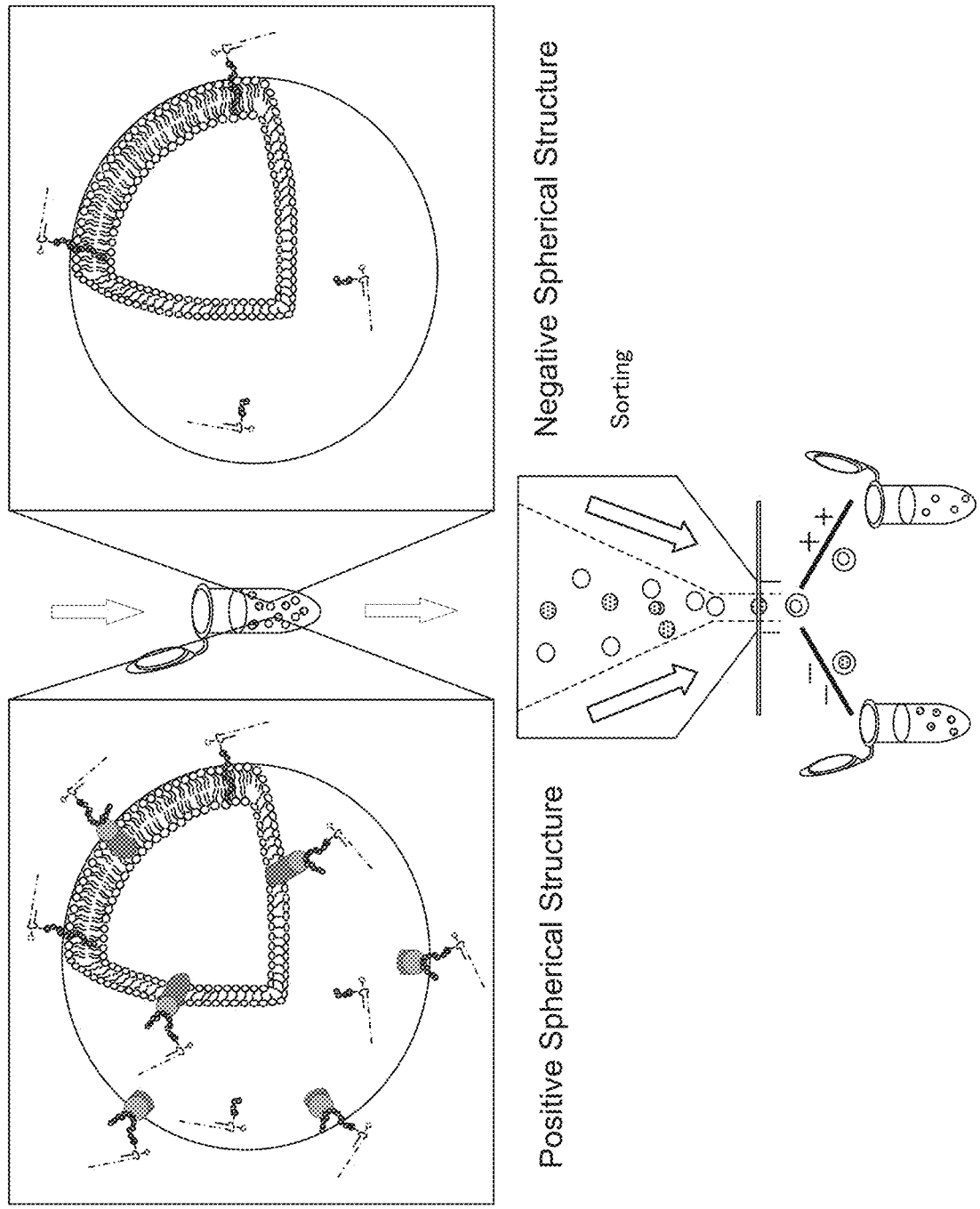

Outer Membrane LBP – mCherry 2 µM

Outer Membrane mCherry 2 µM

R: Reference (Nucleic Acids before FACS selection)
P: Positive (Nucleic acids Eluted from Plus Beads)
N: Negative (Nucleic Acids Eluted from Minus Beads)

SEQUENCE LISTING

<160> NUMBER OF SEQ ID NOS: 40

<210> SEQ ID NO 1
<211> LENGTH: 41
<212> TYPE: DNA
<213> ORGANISM: Artificial Sequence
<220> FEATURE:
<223> OTHER INFORMATION: main branch (backbone of photo-crosslinking
      linker)
<220> FEATURE:
<221> NAME/KEY: misc_feature
<222> LOCATION: (21)..(21)
<223> OTHER INFORMATION: Inosine
<220> FEATURE:
<221> NAME/KEY: misc_feature
<222> LOCATION: (38)..(38)
<223> OTHER INFORMATION: amino modifier C6 dT

<400> SEQUENCE: 1
aaaaaaaaaa aaaaaaaaaa nttccagccg cccccccgncc t                      41

<210> SEQ ID NO 2
<211> LENGTH: 8
<212> TYPE: DNA
<213> ORGANISM: Artificial Sequence
<220> FEATURE:
<223> OTHER INFORMATION: side chain of the linker
<220> FEATURE:
<221> NAME/KEY: misc_feature
<222> LOCATION: (1)..(1)
<223> OTHER INFORMATION: 5'Thiol C6 attached to this nucleotide; shown
      at "R" in specification
<220> FEATURE:
<221> NAME/KEY: misc_feature
<222> LOCATION: (4)..(4)
<223> OTHER INFORMATION: FITC attached to this nucleotide (FITC-dT);
      shown as "Y" in specification
<220> FEATURE:
<221> NAME/KEY: misc_feature
<222> LOCATION: (5)..(6)
<223> OTHER INFORMATION: Spacer 18 (phosphoramidite 18); shown as "M" in
      the specification
<220> FEATURE:
<221> NAME/KEY: misc_feature
<222> LOCATION: (8)..(8)
<223> OTHER INFORMATION: Puromycin attached to this nucleotide as the
      peptide binding site; shown as "K" specifification

<400> SEQUENCE: 2 tcttnncc                                                             8

<210> SEQ ID NO 3
<211> LENGTH: 136
<212> TYPE: DNA
<213> ORGANISM: Artificial Sequence
<220> FEATURE:
<223> OTHER INFORMATION: Random Sequence
<220> FEATURE:
<221> NAME/KEY: misc_feature
<222> LOCATION: (18)..(18)
<223> OTHER INFORMATION: B as defined in Table 6
<220> FEATURE:
<221> NAME/KEY: misc_feature
<222> LOCATION: (19)..(19)
<223> OTHER INFORMATION: D as defined in Table 6
<220> FEATURE:
<221> NAME/KEY: misc_feature
<222> LOCATION: (20)..(20)
<223> OTHER INFORMATION: H as defined in Table 6
<220> FEATURE:
<221> NAME/KEY: misc_feature
<222> LOCATION: (21)..(21)
<223> OTHER INFORMATION: B as defined in Table 6
<220> FEATURE:

```
<221> NAME/KEY: misc_feature
<222> LOCATION: (22)..(22)
<223> OTHER INFORMATION: D as defined in Table 6
<220> FEATURE:
<221> NAME/KEY: misc_feature
<222> LOCATION: (23)..(23)
<223> OTHER INFORMATION: H as defined in Table 6
<220> FEATURE:
<221> NAME/KEY: misc_feature
<222> LOCATION: (24)..(24)
<223> OTHER INFORMATION: K as defined in Table 6
<220> FEATURE:
<221> NAME/KEY: misc_feature
<222> LOCATION: (25)..(25)
<223> OTHER INFORMATION: S as defined in Table 6
<220> FEATURE:
<221> NAME/KEY: misc_feature
<222> LOCATION: (26)..(26)
<223> OTHER INFORMATION: W as defined in Table 6
<220> FEATURE:
<221> NAME/KEY: misc_feature
<222> LOCATION: (27)..(27)
<223> OTHER INFORMATION: R as defined in Table 6
<220> FEATURE:
<221> NAME/KEY: misc_feature
<222> LOCATION: (28)..(28)
<223> OTHER INFORMATION: Y as defined in Table 6
<220> FEATURE:
<221> NAME/KEY: misc_feature
<222> LOCATION: (29)..(29)
<223> OTHER INFORMATION: M as defined in Table 6
<220> FEATURE:
<221> NAME/KEY: misc_feature
<222> LOCATION: (30)..(30)
<223> OTHER INFORMATION: K as defined in Table 6
<220> FEATURE:
<221> NAME/KEY: misc_feature
<222> LOCATION: (31)..(31)
<223> OTHER INFORMATION: S as defined in Table 6
<220> FEATURE:
<221> NAME/KEY: misc_feature
<222> LOCATION: (32)..(32)
<223> OTHER INFORMATION: W as defined in Table 6
<220> FEATURE:
<221> NAME/KEY: misc_feature
<222> LOCATION: (33)..(33)
<223> OTHER INFORMATION: K as defined in Table 6
<220> FEATURE:
<221> NAME/KEY: misc_feature
<222> LOCATION: (34)..(34)
<223> OTHER INFORMATION: S as defined in Table 6
<220> FEATURE:
<221> NAME/KEY: misc_feature
<222> LOCATION: (35)..(35)
<223> OTHER INFORMATION: W as defined in Table 6
<220> FEATURE:
<221> NAME/KEY: misc_feature
<222> LOCATION: (36)..(36)
<223> OTHER INFORMATION: R as defined in Table 6
<220> FEATURE:
<221> NAME/KEY: misc_feature
<222> LOCATION: (37)..(37)
<223> OTHER INFORMATION: Y as defined in Table 6
<220> FEATURE:
<221> NAME/KEY: misc_feature
<222> LOCATION: (38)..(38)
<223> OTHER INFORMATION: M as defined in Table 6
<220> FEATURE:
<221> NAME/KEY: misc_feature
<222> LOCATION: (39)..(39)
<223> OTHER INFORMATION: R as defined in Table 6
<220> FEATURE:
<221> NAME/KEY: misc_feature
<222> LOCATION: (40)..(40)
<223> OTHER INFORMATION: Y as defined in Table 6
<220> FEATURE:
<221> NAME/KEY: misc_feature
<222> LOCATION: (41)..(41)
<223> OTHER INFORMATION: M as defined in Table 6
```

```
<220> FEATURE:
<221> NAME/KEY: misc_feature
<222> LOCATION: (42)..(42)
<223> OTHER INFORMATION: K as defined in Table 6
<220> FEATURE:
<221> NAME/KEY: misc_feature
<222> LOCATION: (43)..(43)
<223> OTHER INFORMATION: S as defined in Table 6
<220> FEATURE:
<221> NAME/KEY: misc_feature
<222> LOCATION: (44)..(44)
<223> OTHER INFORMATION: W as defined in Table
<220> FEATURE:
<221> NAME/KEY: misc_feature
<222> LOCATION: (45)..(45)
<223> OTHER INFORMATION: K as defined in Table 6
<220> FEATURE:
<221> NAME/KEY: misc_feature
<222> LOCATION: (46)..(46)
<223> OTHER INFORMATION: S as defined in Table 6
<220> FEATURE:
<221> NAME/KEY: misc_feature
<222> LOCATION: (47)..(47)
<223> OTHER INFORMATION: W as defined in Table 6
<220> FEATURE:
<221> NAME/KEY: misc_feature
<222> LOCATION: (48)..(48)
<223> OTHER INFORMATION: R as defined in Table 6
<220> FEATURE:
<221> NAME/KEY: misc_feature
<222> LOCATION: (49)..(49)
<223> OTHER INFORMATION: Y as defined in Table 6
<220> FEATURE:
<221> NAME/KEY: misc_feature
<222> LOCATION: (50)..(50)
<223> OTHER INFORMATION: M as defined in Table 6
<220> FEATURE:
<221> NAME/KEY: misc_feature
<222> LOCATION: (51)..(51)
<223> OTHER INFORMATION: K as defined in Table 6
<220> FEATURE:
<221> NAME/KEY: misc_feature
<222> LOCATION: (52)..(52)
<223> OTHER INFORMATION: S as defined in Table 6
<220> FEATURE:
<221> NAME/KEY: misc_feature
<222> LOCATION: (53)..(53)
<223> OTHER INFORMATION: W as defined in Table 6
<220> FEATURE:
<221> NAME/KEY: misc_feature
<222> LOCATION: (54)..(54)
<223> OTHER INFORMATION: K as defined in Table 6
<220> FEATURE:
<221> NAME/KEY: misc_feature
<222> LOCATION: (55)..(55)
<223> OTHER INFORMATION: S as defined in Table 6
<220> FEATURE:
<221> NAME/KEY: misc_feature
<222> LOCATION: (56)..(56)
<223> OTHER INFORMATION: W as defined in Table 6
<220> FEATURE:
<221> NAME/KEY: misc_feature
<222> LOCATION: (57)..(57)
<223> OTHER INFORMATION: R as defined in Table 6
<220> FEATURE:
<221> NAME/KEY: misc_feature
<222> LOCATION: (58)..(58)
<223> OTHER INFORMATION: Y as defined in Table 6
<220> FEATURE:
<221> NAME/KEY: misc_feature
<222> LOCATION: (59)..(59)
<223> OTHER INFORMATION: M as defined in Table 6
<220> FEATURE:
<221> NAME/KEY: misc_feature
<222> LOCATION: (60)..(60)
<223> OTHER INFORMATION: R as defined in Table 6
<220> FEATURE:
<221> NAME/KEY: misc_feature
<222> LOCATION: (61)..(61)
```

```
<223> OTHER INFORMATION: Y as defined in Table 6
<220> FEATURE:
<221> NAME/KEY: misc_feature
<222> LOCATION: (62)..(62)
<223> OTHER INFORMATION: M as defined in Table 6
<220> FEATURE:
<221> NAME/KEY: misc_feature
<222> LOCATION: (63)..(63)
<223> OTHER INFORMATION: K as defined in Table 6
<220> FEATURE:
<221> NAME/KEY: misc_feature
<222> LOCATION: (64)..(64)
<223> OTHER INFORMATION: S as defined in Table 6
<220> FEATURE:
<221> NAME/KEY: misc_feature
<222> LOCATION: (65)..(65)
<223> OTHER INFORMATION: W as defined in Table 6
<220> FEATURE:
<221> NAME/KEY: misc_feature
<222> LOCATION: (66)..(66)
<223> OTHER INFORMATION: B as defined in Table 6
<220> FEATURE:
<221> NAME/KEY: misc_feature
<222> LOCATION: (67)..(67)
<223> OTHER INFORMATION: D as defined in Table 6
<220> FEATURE:
<221> NAME/KEY: misc_feature
<222> LOCATION: (68)..(68)
<223> OTHER INFORMATION: H as defined in Table 6
<220> FEATURE:
<221> NAME/KEY: misc_feature
<222> LOCATION: (69)..(69)
<223> OTHER INFORMATION: B as defined in Table 6
<220> FEATURE:
<221> NAME/KEY: misc_feature
<222> LOCATION: (70)..(70)
<223> OTHER INFORMATION: D as defined in Table 6
<220> FEATURE:
<221> NAME/KEY: misc_feature
<222> LOCATION: (71)..(71)
<223> OTHER INFORMATION: H as defined in Table 6
<220> FEATURE:
<221> NAME/KEY: misc_feature
<222> LOCATION: (72)..(72)
<223> OTHER INFORMATION: B as defined in Table 6
<220> FEATURE:
<221> NAME/KEY: misc_feature
<222> LOCATION: (73)..(73)
<223> OTHER INFORMATION: D as defined in Table 6
<220> FEATURE:
<221> NAME/KEY: misc_feature
<222> LOCATION: (74)..(74)
<223> OTHER INFORMATION: H as defined in Table 6
<220> FEATURE:
<221> NAME/KEY: misc_feature
<222> LOCATION: (75)..(75)
<223> OTHER INFORMATION: B as defined in Table 6
<220> FEATURE:
<221> NAME/KEY: misc_feature
<222> LOCATION: (76)..(76)
<223> OTHER INFORMATION: D as defined in Table 6
<220> FEATURE:
<221> NAME/KEY: misc_feature
<222> LOCATION: (77)..(77)
<223> OTHER INFORMATION: H as defined in Table 6
<220> FEATURE:
<221> NAME/KEY: misc_feature
<222> LOCATION: (78)..(78)
<223> OTHER INFORMATION: K as defined in Table 6
<220> FEATURE:
<221> NAME/KEY: misc_feature
<222> LOCATION: (79)..(79)
<223> OTHER INFORMATION: S as defined in Table 6
<220> FEATURE:
<221> NAME/KEY: misc_feature
<222> LOCATION: (80)..(80)
<223> OTHER INFORMATION: W as defined in Table 6
<220> FEATURE:
<221> NAME/KEY: misc_feature
```

```
-continued

<222> LOCATION: (81)..(81)
<223> OTHER INFORMATION: R as defined in Table 6
<220> FEATURE:
<221> NAME/KEY: misc_feature
<222> LOCATION: (82)..(82)
<223> OTHER INFORMATION: Y as defined in Table 6
<220> FEATURE:
<221> NAME/KEY: misc_feature
<222> LOCATION: (83)..(83)
<223> OTHER INFORMATION: M as defined in Table 6
<220> FEATURE:
<221> NAME/KEY: misc_feature
<222> LOCATION: (84)..(84)
<223> OTHER INFORMATION: K as defined in Table 6
<220> FEATURE:
<221> NAME/KEY: misc_feature
<222> LOCATION: (85)..(85)
<223> OTHER INFORMATION: S as defined in Table 6
<220> FEATURE:
<221> NAME/KEY: misc_feature
<222> LOCATION: (86)..(86)
<223> OTHER INFORMATION: W as defined in Table 6
<220> FEATURE:
<221> NAME/KEY: misc_feature
<222> LOCATION: (87)..(87)
<223> OTHER INFORMATION: K as defined in Table 6
<220> FEATURE:
<221> NAME/KEY: misc_feature
<222> LOCATION: (88)..(88)
<223> OTHER INFORMATION: S as defined in Table 6
<220> FEATURE:
<221> NAME/KEY: misc_feature
<222> LOCATION: (89)..(89)
<223> OTHER INFORMATION: W as defined in Table 6
<220> FEATURE:
<221> NAME/KEY: misc_feature
<222> LOCATION: (90)..(90)
<223> OTHER INFORMATION: R as defined in Table 6
<220> FEATURE:
<221> NAME/KEY: misc_feature
<222> LOCATION: (91)..(92)
<223> OTHER INFORMATION: Y as defined in Table 6
<220> FEATURE:
<221> NAME/KEY: misc_feature
<222> LOCATION: (92)..(92)
<223> OTHER INFORMATION: M as defined in Table 6
<220> FEATURE:
<221> NAME/KEY: misc_feature
<222> LOCATION: (93)..(93)
<223> OTHER INFORMATION: R as defined in Table 6
<220> FEATURE:
<221> NAME/KEY: misc_feature
<222> LOCATION: (94)..(94)
<223> OTHER INFORMATION: Y as defined in Table 6
<220> FEATURE:
<221> NAME/KEY: misc_feature
<222> LOCATION: (95)..(95)
<223> OTHER INFORMATION: M as defined in Table 6
<220> FEATURE:
<221> NAME/KEY: misc_feature
<222> LOCATION: (96)..(06)
<223> OTHER INFORMATION: K as defined in Table 6
<220> FEATURE:
<221> NAME/KEY: misc_feature
<222> LOCATION: (96)..(96)
<223> OTHER INFORMATION: n is a, c, g, or t
<220> FEATURE:
<221> NAME/KEY: misc_feature
<222> LOCATION: (97)..(97)
<223> OTHER INFORMATION: S as defined in Table 6
<220> FEATURE:
<221> NAME/KEY: misc_feature
<222> LOCATION: (98)..(98)
<223> OTHER INFORMATION: W as defined in Table 6
<220> FEATURE:
<221> NAME/KEY: misc_feature
<222> LOCATION: (99)..(99)
<223> OTHER INFORMATION: K as defined in Table 6
<220> FEATURE:
```

```
<221> NAME/KEY: misc_feature
<222> LOCATION: (100)..(100)
<223> OTHER INFORMATION: S as defined in Table 6
<220> FEATURE:
<221> NAME/KEY: misc_feature
<222> LOCATION: (100)..(100)
<223> OTHER INFORMATION: S as defined in Table 6
<220> FEATURE:
<221> NAME/KEY: misc_feature
<222> LOCATION: (101)..(101)
<223> OTHER INFORMATION: W as defined in Table 6
<220> FEATURE:
<221> NAME/KEY: misc_feature
<222> LOCATION: (102)..(102)
<223> OTHER INFORMATION: R as defined in Table 6
<220> FEATURE:
<221> NAME/KEY: misc_feature
<222> LOCATION: (103)..(103)
<223> OTHER INFORMATION: Y as defined in Table 6
<220> FEATURE:
<221> NAME/KEY: misc_feature
<222> LOCATION: (104)..(104)
<223> OTHER INFORMATION: M as defined in Table 6
<220> FEATURE:
<221> NAME/KEY: misc_feature
<222> LOCATION: (105)..(105)
<223> OTHER INFORMATION: K as defined in Table 6
<220> FEATURE:
<221> NAME/KEY: misc_feature
<222> LOCATION: (106)..(106)
<223> OTHER INFORMATION: S as defined in Table 6
<220> FEATURE:
<221> NAME/KEY: misc_feature
<222> LOCATION: (107)..(107)
<223> OTHER INFORMATION: W as defined in Table 6
<220> FEATURE:
<221> NAME/KEY: misc_feature
<222> LOCATION: (108)..(108)
<223> OTHER INFORMATION: K as defined in Table 6
<220> FEATURE:
<221> NAME/KEY: misc_feature
<222> LOCATION: (109)..(109)
<223> OTHER INFORMATION: n is a, c, g, or t
<220> FEATURE:
<221> NAME/KEY: misc_feature
<222> LOCATION: (110)..(110)
<223> OTHER INFORMATION: W as defined in Table 6
<220> FEATURE:
<221> NAME/KEY: misc_feature
<222> LOCATION: (111)..(111)
<223> OTHER INFORMATION: R as defined in Table 6
<220> FEATURE:
<221> NAME/KEY: misc_feature
<222> LOCATION: (112)..(112)
<223> OTHER INFORMATION: Y as defined in Table 6
<220> FEATURE:
<221> NAME/KEY: misc_feature
<222> LOCATION: (113)..(113)
<223> OTHER INFORMATION: M as defined in Table 6
<220> FEATURE:
<221> NAME/KEY: misc_feature
<222> LOCATION: (114)..(114)
<223> OTHER INFORMATION: R as defined in Table 6
<220> FEATURE:
<221> NAME/KEY: misc_feature
<222> LOCATION: (115)..(115)
<223> OTHER INFORMATION: Y as defined in Table 6
<220> FEATURE:
<221> NAME/KEY: misc_feature
<222> LOCATION: (116)..(116)
<223> OTHER INFORMATION: M as defined in Table 6
<220> FEATURE:
<221> NAME/KEY: misc_feature
<222> LOCATION: (117)..(117)
<223> OTHER INFORMATION: K as defined in Table 6
<220> FEATURE:
<221> NAME/KEY: misc_feature
<222> LOCATION: (118)..(118)
<223> OTHER INFORMATION: S as defined in Table 6
```

```
<220> FEATURE:
<221> NAME/KEY: misc_feature
<222> LOCATION: (119)..(119)
<223> OTHER INFORMATION: W as defined in Table 6
<220> FEATURE:
<221> NAME/KEY: misc_feature
<222> LOCATION: (120)..(120)
<223> OTHER INFORMATION: B as defined in Table 6
<220> FEATURE:
<221> NAME/KEY: misc_feature
<222> LOCATION: (121)..(121)
<223> OTHER INFORMATION: D as defined in Table 6
<220> FEATURE:
<221> NAME/KEY: misc_feature
<222> LOCATION: (122)..(122)
<223> OTHER INFORMATION: B as defined in Table 6

<400> SEQUENCE: 3
attccaccat gggcggtnnn nnnnnnnnnn nnnnnnnnnn nnnnnnnnnn nnnnnnnnnn    60
nnnnnnnnnn nnnnnnnnnn nnnnnnnnnn nnnnnnnnnn nnnnnnnnnn nnnnnnnnnn   120 nnggggagg cagcca                                                      136

<210> SEQ ID NO 4
<211> LENGTH: 37
<212> TYPE: DNA
<213> ORGANISM: Artificial Sequence
<220> FEATURE:
<223> OTHER INFORMATION: R-Ytag
<220> FEATURE:
<221> NAME/KEY: misc_feature
<222> LOCATION: (1)..(37)

<400> SEQUENCE: 4
tttccccgcc gcccccgtc ctatggctgc ctccccc                              37

<210> SEQ ID NO 5
<211> LENGTH: 101
<212> TYPE: DNA
<213> ORGANISM: Artificial Sequence
<220> FEATURE:
<223> OTHER INFORMATION: T7-PRO-SD
<220> FEATURE:
<221> NAME/KEY: misc_feature
<222> LOCATION: (1)..(101)

<400> SEQUENCE: 5
gatcccgcga aattaatacg actcactata gggagaccac aacggtttcc ctctagaaat    60
aattttgttt aactttaaga aggagattcc accatgggcg g                       101

<210> SEQ ID NO 6
<211> LENGTH: 51
<212> TYPE: DNA
<213> ORGANISM: Artificial Sequence
<220> FEATURE:
<223> OTHER INFORMATION: Fw Rrimer
<220> FEATURE:
<221> NAME/KEY: primer_bind
<222> LOCATION: (1)..(51)

<400> SEQUENCE: 6
gatcccgcga aattaatacg actcactata gggagaccac aacggtttcc c             51

<210> SEQ ID NO 7
<211> LENGTH: 22
<212> TYPE: DNA
<213> ORGANISM: Artificial Sequence
<220> FEATURE:
<223> OTHER INFORMATION: Rv Primer
```

<220> FEATURE:
<221> NAME/KEY: primer_bind
<222> LOCATION: (1)..(22)

<400> SEQUENCE: 7
tttccccgcc gccccccgtc ct                                                   22

<210> SEQ ID NO 8
<211> LENGTH: 35
<212> TYPE: PRT
<213> ORGANISM: Artificial Sequence
<220> FEATURE:
<223> OTHER INFORMATION: designed peptide
<220> FEATURE:
<221> NAME/KEY: PEPTIDE
<222> LOCATION: (1)..(35)

<400> SEQUENCE: 8

Thr Asp Gln Phe Lys Arg Cys Ala Arg Thr Met Glu Lys Val Thr Gln
1               5                   10                  15

Cys Pro Met Ile Glu Thr Lys Glu Gly Ala Thr Lys Ile Glu Ser Pro
            20                  25                  30

Pro Gln Arg
        35

<210> SEQ ID NO 9
<211> LENGTH: 31
<212> TYPE: PRT
<213> ORGANISM: Artificial Sequence
<220> FEATURE:
<223> OTHER INFORMATION: Result peptide
<220> FEATURE:
<221> NAME/KEY: PEPTIDE
<222> LOCATION: (1)..(31)

<400> SEQUENCE: 9

Arg His Ser Lys Ser Leu Pro Ser Arg Val Ile Pro Arg Ala Asp Pro
1               5                   10                  15

Arg Thr Lys Thr Arg Arg Arg Arg Arg Lys Arg Thr Leu Cys
            20                  25                  30

<210> SEQ ID NO 10
<211> LENGTH: 103
<212> TYPE: DNA
<213> ORGANISM: Artificial Sequence
<220> FEATURE:
<223> OTHER INFORMATION: 5' primer
<220> FEATURE:
<221> NAME/KEY: misc_feature
<222> LOCATION: (1)..(103)

<400> SEQUENCE: 10
agtaatacga ctcactatag ggagtcgacc gaccagaatc atgcaagtgc gtaagatagt        60
cgcgggccgg gggcgtatta tgtgcgtcta catctagact cat                         103

<210> SEQ ID NO 11
<211> LENGTH: 25
<212> TYPE: DNA
<213> ORGANISM: Artificial Sequence
<220> FEATURE:
<223> OTHER INFORMATION: 3' primer
<220> FEATURE:
<221> NAME/KEY: misc_feature
<222> LOCATION: (1)..(25)

<400> SEQUENCE: 11
atgagtctag atgtagacgc acata                                          25

<210> SEQ ID NO 12
<211> LENGTH: 93
<212> TYPE: DNA
<213> ORGANISM: Artificial Sequence
<220> FEATURE:
<223> OTHER INFORMATION: 5' primer
<220> FEATURE:
<221> NAME/KEY: misc_feature
<222> LOCATION: (1)..(93)

<400> SEQUENCE: 12
agtaatacga ctcactatag ggagtcgacc gaccagaaat ggataacaaa ttcaacaaag    60
aacaacaata tgtgcgtcta catctagact cat                                 93

<210> SEQ ID NO 13
<211> LENGTH: 38
<212> TYPE: DNA
<213> ORGANISM: Artificial Sequence
<220> FEATURE:
<223> OTHER INFORMATION: T7 primer
<220> FEATURE:
<221> NAME/KEY: misc_feature
<222> LOCATION: (1)..(38)

<400> SEQUENCE: 13
agtaatacga ctcactatag ggagtcgacc gaccagaa                            38

<210> SEQ ID NO 14
<211> LENGTH: 27
<212> TYPE: DNA
<213> ORGANISM: Artificial Sequence
<220> FEATURE:
<223> OTHER INFORMATION: Main chain of SBS linker
<220> FEATURE:
<221> NAME/KEY: misc_feature
<222> LOCATION: (3)..(3)
<223> OTHER INFORMATION: riboguanosine (rG)
<220> FEATURE:
<221> NAME/KEY: misc_feature
<222> LOCATION: (5)..(5)
<223> OTHER INFORMATION: biotin-dT (Biotin-modified thymidine residue)
<220> FEATURE:
<221> NAME/KEY: misc_feature
<222> LOCATION: (7)..(7)
<223> OTHER INFORMATION: riboguanosine (rG)
<220> FEATURE:
<221> NAME/KEY: misc_feature
<222> LOCATION: (24)..(24)
<223> OTHER INFORMATION: amino modifier C6 dT

<400> SEQUENCE: 14
ccncncnacc ccgccgcccc ccgncct                                        27

<210> SEQ ID NO 15
<211> LENGTH: 42
<212> TYPE: DNA
<213> ORGANISM: Artificial Sequence
<220> FEATURE:
<223> OTHER INFORMATION: Sequence of linker backbone
<220> FEATURE:
<221> NAME/KEY: misc_feature
<222> LOCATION: (21)..(21)
<223> OTHER INFORMATION: Inosine
<220> FEATURE:
<221> NAME/KEY: misc_feature
<222> LOCATION: (27)..(27)
<223> OTHER INFORMATION: 3-cyano vinylcarbazole (cvnK)

<400> SEQUENCE: 15
aaaaaaaaaa aaaaaaaaaa nttccangcc gcccccgtc ct                42

<210> SEQ ID NO 16
<211> LENGTH: 117
<212> TYPE: DNA
<213> ORGANISM: Artificial Sequence
<220> FEATURE:
<223> OTHER INFORMATION: VHH-specific 5' primer
<220> FEATURE:
<221> NAME/KEY: primer_bind
<222> LOCATION: (1)..(117)

<400> SEQUENCE: 16
gatcccgcga aattaatacg actcactata ggggaagtat ttttacaaca attaccaaca    60
acaacaacaa acaacaacaa cattacattt tacattctac aactacaagc caccatg     117

<210> SEQ ID NO 17
<211> LENGTH: 61
<212> TYPE: DNA
<213> ORGANISM: Artificial Sequence
<220> FEATURE:
<223> OTHER INFORMATION: VHH-specific 3' primer
<220> FEATURE:
<221> NAME/KEY: primer_bind
<222> LOCATION: (1)..(61)

<400> SEQUENCE: 17
tttccacgcc gcccccgtc ctgcttccgc cgtgatgatg atgatgatgg ctgcctcccc    60
c                                                                   61

<210> SEQ ID NO 18
<211> LENGTH: 117
<212> TYPE: DNA
<213> ORGANISM: Artificial Sequence
<220> FEATURE:
<223> OTHER INFORMATION: 5' primer for overlap PCR
<220> FEATURE:
<221> NAME/KEY: primer_bind
<222> LOCATION: (1)..(117)

<400> SEQUENCE: 18
gatcccgcga aattaatacg actcactata ggggaagtat ttttacaaca attaccaaca    60
acaacaacaa acaacaacaa cattacattt tacattctac aactacaagc caccatg     117

<210> SEQ ID NO 19
<211> LENGTH: 61
<212> TYPE: DNA
<213> ORGANISM: Artificial Sequence
<220> FEATURE:
<223> OTHER INFORMATION: 3' primer for overlap PCR
<220> FEATURE:
<221> NAME/KEY: primer_bind
<222> LOCATION: (1)..(61)

<400> SEQUENCE: 19
tttccacgcc gcccccgtc ctgcttccgc cgtgatgatg atgatgatgg ctgcctcccc    60
c                                                                   61

<210> SEQ ID NO 20
<211> LENGTH: 60
<212> TYPE: DNA
<213> ORGANISM: Artificial Sequence
<220> FEATURE:
<223> OTHER INFORMATION: T7 omega_New primer
<220> FEATURE:

```
<221> NAME/KEY: primer_bind
<222> LOCATION: (1)..(60)

<400> SEQUENCE: 20
gatcccgcga aattaatacg actcactata ggggaagtat ttttacaaca attaccaaca      60

<210> SEQ ID NO 21
<211> LENGTH: 22
<212> TYPE: DNA
<213> ORGANISM: Artificial Sequence
<220> FEATURE:
<223> OTHER INFORMATION: NewYtag for polyA cnvK primer
<220> FEATURE:
<221> NAME/KEY: primer_bind
<222> LOCATION: (1)..(22)

<400> SEQUENCE: 21
tttccacgcc gccccccgtc ct                                               22

<210> SEQ ID NO 22
<211> LENGTH: 58
<212> TYPE: DNA
<213> ORGANISM: Artificial Sequence
<220> FEATURE:
<223> OTHER INFORMATION: Amplicon PCR Forward Primer
<220> FEATURE:
<221> NAME/KEY: primer_bind
<222> LOCATION: (1)..(58)
<220> FEATURE:
<221> NAME/KEY: misc_feature
<222> LOCATION: (34)..(37)
<223> OTHER INFORMATION: n is a, c, g, or t

<400> SEQUENCE: 22
tcgtcggcag cgtcagatgt gtataagaga cagnnnnatg gctgaggtgc agctcgtg       58

<210> SEQ ID NO 23
<211> LENGTH: 63
<212> TYPE: DNA
<213> ORGANISM: Artificial Sequence
<220> FEATURE:
<223> OTHER INFORMATION: Amplicon PCR Reverse Primer
<220> FEATURE:
<221> NAME/KEY: primer_bind
<222> LOCATION: (1)..(63)
<220> FEATURE:
<221> NAME/KEY: misc_feature
<222> LOCATION: (35)..(38)
<223> OTHER INFORMATION: n is a, c, g, or t

<400> SEQUENCE: 23
gtctcgtggg ctcggagatg tgtataagag acagnnnntg atgatgatgg ctaccacctc      60
ccg                                                                    63

<210> SEQ ID NO 24
<211> LENGTH: 7
<212> TYPE: PRT
<213> ORGANISM: Artificial Sequence
<220> FEATURE:
<223> OTHER INFORMATION: Peptide sequence obtained in FACS samples (Top
      10 sequence frequently appeared)
<220> FEATURE:
<221> NAME/KEY: PEPTIDE
<222> LOCATION: (1)..(7)

<400> SEQUENCE: 24

Leu Ser Gly Gly Arg Gln Tyr
1               5
```

<210> SEQ ID NO 25
<211> LENGTH: 6
<212> TYPE: PRT
<213> ORGANISM: Artificial Sequence
<220> FEATURE:
<223> OTHER INFORMATION: Peptide sequence obtained in FACS samples (Top
      10 sequence frequently appeared)
<220> FEATURE:
<221> NAME/KEY: PEPTIDE
<222> LOCATION: (1)..(6)

<400> SEQUENCE: 25

Asp Pro Pro Leu Asp Tyr
1               5

<210> SEQ ID NO 26
<211> LENGTH: 10
<212> TYPE: PRT
<213> ORGANISM: Artificial Sequence
<220> FEATURE:
<223> OTHER INFORMATION: Peptide sequence obtained in FACS samples (Top
      10 sequence frequently appeared)
<220> FEATURE:
<221> NAME/KEY: PEPTIDE
<222> LOCATION: (1)..(10)

<400> SEQUENCE: 26

Asp Thr Asp Trp Gly Thr Glu Gly Gly Tyr
1               5                   10

<210> SEQ ID NO 27
<211> LENGTH: 14
<212> TYPE: PRT
<213> ORGANISM: Artificial Sequence
<220> FEATURE:
<223> OTHER INFORMATION: Peptide sequence obtained in FACS samples (Top
      10 sequence frequently appeared)
<220> FEATURE:
<221> NAME/KEY: PEPTIDE
<222> LOCATION: (1)..(14)

<400> SEQUENCE: 27

Asn Leu Leu His Asp Asp Cys Asp Leu Gly Asp Met Val Phe
1               5                   10

<210> SEQ ID NO 28
<211> LENGTH: 14
<212> TYPE: PRT
<213> ORGANISM: Artificial Sequence
<220> FEATURE:
<223> OTHER INFORMATION: Peptide sequence obtained in FACS samples (Top
      10 sequence frequently appeared)
<220> FEATURE:
<221> NAME/KEY: PEPTIDE
<222> LOCATION: (1)..(14)

<400> SEQUENCE: 28

Asp Asp Ser Leu Cys Arg Asp Tyr Gly Arg Gly Met Asp Ser
1               5                   10

<210> SEQ ID NO 29
<211> LENGTH: 5
<212> TYPE: PRT
<213> ORGANISM: Artificial Sequence
<220> FEATURE:
<223> OTHER INFORMATION: Peptide sequence obtained in FACS samples (Top
      10 sequence frequently appeared)
<220> FEATURE:
<221> NAME/KEY: PEPTIDE
<222> LOCATION: (1)..(5)

-continued

<400> SEQUENCE: 29

Leu Pro Asn Arg Ser
1               5

<210> SEQ ID NO 30
<211> LENGTH: 16
<212> TYPE: PRT
<213> ORGANISM: Artificial Sequence
<220> FEATURE:
<223> OTHER INFORMATION: Peptide sequence obtained in FACS samples (Top
      10 sequence frequently appeared)
<220> FEATURE:
<221> NAME/KEY: PEPTIDE
<222> LOCATION: (1)..(16)

<400> SEQUENCE: 30

Ser Pro Asp Tyr Arg Gly Gly Tyr Tyr Tyr Thr Asp Glu Tyr Asp Tyr
1               5                   10                  15

<210> SEQ ID NO 31
<211> LENGTH: 7
<212> TYPE: PRT
<213> ORGANISM: Artificial Sequence
<220> FEATURE:
<223> OTHER INFORMATION: Peptide sequence obtained in FACS samples (Top
      10 sequence frequently appeared)
<220> FEATURE:
<221> NAME/KEY: PEPTIDE
<222> LOCATION: (1)..(7)

<400> SEQUENCE: 31

Leu Leu Gly Thr Arg Leu Tyr
1               5

<210> SEQ ID NO 32
<211> LENGTH: 8
<212> TYPE: PRT
<213> ORGANISM: Artificial Sequence
<220> FEATURE:
<223> OTHER INFORMATION: Peptide sequence obtained in FACS samples (Top
      10 sequence frequently appeared)
<220> FEATURE:
<221> NAME/KEY: PEPTIDE
<222> LOCATION: (1)..(8)

<400> SEQUENCE: 32

Asp Thr His Trp Gly Tyr Asp Ser
1               5

<210> SEQ ID NO 33
<211> LENGTH: 19
<212> TYPE: PRT
<213> ORGANISM: Artificial Sequence
<220> FEATURE:
<223> OTHER INFORMATION: Peptide sequence obtained in FACS samples (Top
      10 sequence frequently appeared)
<220> FEATURE:
<221> NAME/KEY: PEPTIDE
<222> LOCATION: (1)..(19)

<400> SEQUENCE: 33

Arg Ala Arg Tyr Leu Pro Ala Asp Val Ile Leu Ser Pro Glu Thr Ala
1               5                   10                  15

Tyr Asp Tyr

<210> SEQ ID NO 34
<211> LENGTH: 11

```
<212> TYPE: PRT
<213> ORGANISM: Artificial Sequence
<220> FEATURE:
<223> OTHER INFORMATION: Peptide sequence obtained in (R5) sample
<220> FEATURE:
<221> NAME/KEY: PEPTIDE
<222> LOCATION: (1)..(11)

<400> SEQUENCE: 34

Glu Asn Gly Gly Phe Gly Tyr Gly Gln Asn Phe
1               5                   10

<210> SEQ ID NO 35
<211> LENGTH: 9
<212> TYPE: PRT
<213> ORGANISM: Artificial Sequence
<220> FEATURE:
<223> OTHER INFORMATION: Peptide sequence obtained in (R5) sample
<220> FEATURE:
<221> NAME/KEY: PEPTIDE
<222> LOCATION: (1)..(9)

<400> SEQUENCE: 35

Arg His Ile Val Ala Arg Tyr Glu Tyr
1               5

<210> SEQ ID NO 36
<211> LENGTH: 9
<212> TYPE: PRT
<213> ORGANISM: Artificial Sequence
<220> FEATURE:
<223> OTHER INFORMATION: Peptide sequence obtained in (R5) sample
<220> FEATURE:
<221> NAME/KEY: PEPTIDE
<222> LOCATION: (1)..(9)

<400> SEQUENCE: 36

Ile Arg Trp Gly Thr Ser Pro Asp Glu
1               5

<210> SEQ ID NO 37
<211> LENGTH: 15
<212> TYPE: PRT
<213> ORGANISM: Artificial Sequence
<220> FEATURE:
<223> OTHER INFORMATION: Amino acid sequence of CD3 in clone A
<220> FEATURE:
<221> NAME/KEY: MISC_FEATURE
<222> LOCATION: (1)..(15)

<400> SEQUENCE: 37

Arg Gly Asp Ser Gly Ser Asn Phe Asp Pro Ser Gly Tyr Arg Tyr
1               5                   10                  15

<210> SEQ ID NO 38
<211> LENGTH: 10
<212> TYPE: PRT
<213> ORGANISM: Artificial Sequence
<220> FEATURE:
<223> OTHER INFORMATION: Amino acid sequence of CD3 in clone B
<220> FEATURE:
<221> NAME/KEY: MISC_FEATURE
<222> LOCATION: (1)..(10)

<400> SEQUENCE: 38

Phe Trp Leu Pro Leu Arg Leu Asn Asp Tyr
1               5                   10

<210> SEQ ID NO 39
```

```
<211> LENGTH: 27
<212> TYPE: RNA
<213> ORGANISM: Artificial Sequence
<220> FEATURE:
<223> OTHER INFORMATION: mRNA sequence

<400> SEQUENCE: 39
gaagcaggac gggggcggc guggaaa                                          27

<210> SEQ ID NO 40
<211> LENGTH: 27
<212> TYPE: RNA
<213> ORGANISM: Artificial Sequence
<220> FEATURE:
<223> OTHER INFORMATION: mRNA sequence

<400> SEQUENCE: 40
gaagcaggac gggggcggc ggggaaa                                          27
```

HIGH-SPEED IN VITRO SCREENING METHOD

CROSS-REFERENCE TO RELATED APPLICATIONS

This application is a Continuation-In-Part of U.S. application Ser. No. 16/145,292 filed Sep. 28, 2018 (allowed), which is a Continuation Application of International Application No. PCT/JP2017/013076, filed Mar. 29, 2017, and which claims benefit of Japanese Patent Application No. 2016-069064 filed Mar. 30, 2016, the full contents of all of which are hereby incorporated by reference in their entirely.

REFERENCE TO A SEQUENCE LISTING

The instant application contains a sequence listing which has been submitted electronically in ASCII format named 219792_0001_01_605611_SL.txt, created on Mar. 9, 2021, and is 21,859 bytes in size, which is hereby incorporated by reference.

FIELD OF THE INVENTION

The present invention relates to a high-speed in vitro screening method for a cDNA display or a nucleic acid aptamer.

BACKGROUND ART

At present, intension of research for functional molecules is shifting from the conventional style, wherein they are screened from natural products including creatures, to another style, wherein new functional molecules such as proteins or peptides are created on the basis of artificially synthesized DNA. For example, there is a problem that an antibody has large lot difference because of a mutation which is introduced into them during their passages, even if they are a monoclonal antibody in the field of diagnostic or research reagents.

In contrast, a next generation antibody or the peptide aptamer has following advantages: the mutation is hardly introduced into it, because it is synthesized by using E. coli on the basis of the DNA sequence or artificially synthesized; such synthesis is conducted in low cost; and it has high heat stability. As a molecular evolution engineering for obtaining such next generation antibodies, a variety of display methods are developed, and phage display method is a typical example.

In the phage display method, a desired protein is fused with a coat protein localized on the most outer shell of a bacteriophage to be presented, and then is screened by binding to biotinylated ligand. The method is used for the screening of the antibody, DNA binding protein, a protease inhibitor and the like, and it gives the protein or the peptide, which functions as a physiologically active ligand or a pharmaceutical agent. Also, a display method wherein the protein is displayed on microbes is developed.

Among such display methods, yeast display method, on which peptides having particular activity or peptides are displayed on a surface of yeast, eukaryote has been established. Therefore, a method which enables to display the protein of the eukaryote is proposed to enable to apply them in yeast display method, has been proposed (Non-patent document 1).

In the method, a DNA sequence including a protein of the object is displayed in the following procedure. Firstly, a secretion signal sequence which transfer post translation protein to a cell membrane, code sequence of the protein of the object, a code sequence of the protein localized on the cell wall or the cell membrane, and a code sequence of an anchor protein of the cell membrane is synthesized to manufacture a construct. Next, a yeast cell is transformed by using the construct to express a fused protein, which is exposed to endoplasmic reticulum lumen, is transferred to the cell membrane via Goldi body by using exocytosis through secretory vesicle. After that, the anchor protein is fused with the cell membrane, and the protein of the object is displayed on the cell membrane. When the cell has the cell wall, for example, yeast, the anchor protein is cleaved with an enzyme, and both of the protein of the object and that localized on the cell wall are transferred to the cell wall to display the protein of the object on the cell wall.

By applying the yeast display, Feldhaus et al., developed a method to choose the transformed yeast cell so as to display scFv on the cell surface (See the patent document 1 and non-patent document 2, hereinbelow, it is referred to as the "prior art 1".). Also, the highly efficient and rapid method for yeast transformation to manufacture a library with $2 \times 10^{10}$ size in maximal by using electroporation method is proposed (See the patent document 2: hereinbelow, it is sometimes referred to as the "prior art 2".).

On the other hand, in vitro virus, which mimics a retroviral cycle used in a larger size of the library, and maintains the higher diversity thereof compared with a phage display, was proposed. After that, cDNA display, which is improved one by replacing its nucleic acid portion from mRNA to cDNA, was proposed (Non-patent document 3: hereinbelow, it is sometimes referred to as "Prior art 3".).

Also, other that cDNA display described above, research and development of pharmaceutical preparations or diagnostic reagents utilizing nucleic acid aptamers are progressed. The nucleic acid aptamer has properties that it is manufactured without any living thing; it is manufactured by using chemical synthesis in low cost, and the like. At present, the nucleic acid aptamer corresponding to a desirable target molecule is prepared by using SELEX (systematic evolution of ligand by exponential enrichment) methods and the like.

In SELEX method, the initial library composed of a mixture including from $10^{10}$ to $10^{14}$ of single strand oligo DNA having different sequence is subjected to an affinity column on which target molecules are immobilized to separate the oligo DNA with the binding activity to the target molecule and those without the binding activity. After that, the DNA showed the affinity with the target molecule was amplified by using PCR; and then double strand obtained after amplification was changed to the single strand by using the method utilizing λ exonuclease and the like. After that, the single strand is subjected to the selection by using the column and the like and then amplified with PCR. By repeating the selection and the amplification, the DNA sequence (DNA library) showing the affinity to the target molecule is condensed. Then, DNA aptamer is isolated from the condensed DNA library by using the cloning method.

Recently, the SELEX method is improved. Both of the target molecule immobilized on the solid phase and the nucleic acid library in the liquid phase have different binding affinities, which is utilized to separate the active sequence, however, sometimes nonspecific binding occurs. In the improved method, such non-specific absorption is decreased (See, the non-patent document 4: hereinbelow, it is sometimes referred to as "Prior art 4".).

Further, the screening method for the nucleic acid aptamer which neither use the affinity column nor the capillary zone electrophoresis, but use an atomic force microscope is disclosed (See the patent document 3: hereinbelow, it is sometimes referred to as "Prior art 5".).

Other than these, streptavidin binding RNA aptamer, which may be used as an affinity tag by using biotin as a competitive elution agent, when streptavidin biding RNA aptamer is selected from RNA library is known (See the non-patent document 5: hereinbelow, it is sometimes referred to as "Prior art 6".).

PRIOR ART DOCUMENT

Patent Document

[Patent document 1] U.S. Pat. No. 6,699,658 B1
[Patent document 2] JP 2011-512841
[Patent document 3] JP 2011-055770 A Non-Patent Document

[Non-patent document 1] Bioscience, Biotechnology, and Biochemistry, vol. 40, No. 4 (2002)
[Non-patent document 2] Nature Biotech, vol. 21, 163-170 (2003)
[Non-patent document 3] Nucleic Acid Research, vol. 37, No. 16, e108 (2009)
[Non-patent document 4]
http://www.nedo.go.jp/news/press/AA5_100222.html
[Non-patent document 5] RNA, vol. 7, 632-641 (2001)

SUMMARY OF THE INVENTION

Problems to be Solved by the Invention

Prior art 1 is good technique from the viewpoints that it brings the library the size with $1 \times 10^{10}$ through the screening method by using Fluorescence Activated Cell Sorting (FACS) device in yeast display, and it enables simultaneous screening of a plural antibodies against plural antigens within a couple of weeks. However, it has problems that only 40 to 80% of scFv introduced for the transformation is expressed on the cell surface, and impossible to obtain molecules having high specificity because the expressed scFv binds to different peptides having the same amino acid sequence.

Prior art 2 is the good technique from the view point that is enables to manufacture the library having $2 \times 10^{10}$ size at maximal, which is larger than that disclosed in Prior art 1, by using electroporation to enhance the transformation efficiency itself of yeast. However, there is the problem that the library size is still limited to $10^{10}$ order in either yeast display method.

Furthermore, there is another problem that the display is not quickly constructed, because yeast to which the gene sequences for the protein or peptides were introduced must be cultured; and it must be labeled by using such as antibody and the like, when cell sorting by using FACS is conducted.

Prior art 3 is good technique in the view point from that it enables the screening in a short time compared to those disclosed in both of Prior art 1 and 2. However, in the screening process using the conventional cDNA display method, there are problems that it takes time for half day to several days caused by the manual operation of the condensation or selection of the binding proteins; and it gives varied results caused by the manual operations.

In Prior art 3, the library having $10^{14}$ size, which is almost 1,000 times larger compared to that treated by yeast display method, is constructed. However, the screening process becomes a rate determining step in the operation processes of cDNA display method, and it becomes an obstacle for rapid screening of the molecules having new functions.

Therefore, there is a strong social need for high speed screening of cDNA display by using large size library to obtain the molecule having high specificity.

Prior art 4 is the good technique in the view point from that it enables to highly separate a conjugate of the target molecule and active sequences and inactive ones which do not bind to the target, wherein both of the target molecule and the library are existing in the liquid phase. On the other hand, it may separate the target molecule and the conjugate including the active sequence, however, the inactive sequence does not contaminate in the active sequence fraction in principal. Namely, there is the problem whether the accurate screening is possible or not.

Prior art 5 is the good technique in the view point from that it efficiently screens the nucleic acid aptamer having highly specific binding ability against the low molecular weight compound such as the amino acids and the like. On the other hand, it has the problems that it takes time and labor, for example, the target material should be immobilized on a cantilever in the atomic force microscope, and the nucleic acid should be immobilized on a plate surface which is scanned by using a probe. Therefore, the rapid and convenient screening is still remained as an issue.

Prior art 6 is the good technique in the view point from that it may chose streptavidin binding RNA aptamer from RNA library with $10^{16}$ size by conducting selection cycles for 9 time. However, since the selection conducted here is the purifications by cutting out and using the column, it keeps the condensation efficiency low such as 60 times.

Therefore, there is a strong social need for obtaining the highly specific molecule in the screening of the nucleic acid aptamer.

Means for Solving the Problem

Under such conditions, the inventors of the present invention continue the research to complete the present invention.

Namely, one aspect of the present invention is a method for identifying antibody CDR3 clusters using high speed in vitro screening a library selected from the group consisting of cDNA library and nucleic acid aptamer library comprising steps of:

(i) preparing both of a positive spherical shaped structure or a negative spherical shaped structure, wherein a target molecule is stabilized on the positive spherical shaped structure but it is not stabilized on the negative spherical shaped structure; (ii) forming the positive spherical shaped conjugate or the negative spherical shaped conjugate by binding a target detecting molecule capable of binding to the target molecule, which is selected from the library having the size equal to or more than $10^{10}$ or equal to or less than $10^{14}$ to form the positive spherical shaped structure or the negative spherical shaped structure; (iii) separating the positive and negative spherical shaped conjugates by using a cell sorter with fluorescence; (iv) selecting the separated positive and negative spherical shaped conjugates at least 1 time and then to elute a selected conjugate as an eluted sample; (v) amplifying a nucleic acid in the eluted sample to obtain PCR products; (vi) separating the PCR products by using the cell sorter with fluorescence; and (vii) conducting an amplicon sequencing for cluster analysis to identify the antibody CDR3 clusters.

It is preferable that the spherical shaped structure is any one of selected from the group consisting of liposome, Sepharose bead, silica bead and latex bead, or any one of selected from the group consisting of a liposome-coated Sepharose bead, a liposome-coated silica bead, and a liposome-coated latex bead, from the view point of the immobilization of the target molecule. Also, it is preferable that the spherical shaped structure has a diameter of 0.5 µm to 20 µm, because the sorting by using FACS is conducted accurately.

The target molecule is preferably a nucleic acid-linker conjugate obtained from the cDNA library by using cDNA display method (FIG. 1A) or a nucleic acid aptamer obtained from the nucleic acid-linker conjugate. The target detection molecule is preferably directly bound to the spherical shaped structure via a substitute on their surfaces, or bound to it via the target molecule immobilized on the surface for chose the molecule specifically binding to the spherical structure.

The target molecule is preferably any one of selected from the group consisting of biotin, streptavidin, azide obtained by using click chemistry, and N-hydroxy succinimide ester (NHS), because it gives strong interaction between the target molecule and the target detection molecule. The substitute is preferably any one of selected from the group consisting of carboxyl, amino, hydroxyl, and thiol, because it gives strong interaction between the spherical structure and the target detection molecule.

The target detection molecule is preferably obtained by using cDNA display method comprising the following steps: (a) preparing a desirable mRNA; (b) binding the mRNA to the linker to obtain mRNA-linker-conjugate; (c) forming mRNA-linker-protein conjugate by translating the mRNA-linker-conjugate; and (d) conducting reverse transcription by conducting revers transcription of the mRNA-linker-protein conjugate to obtain mRNA/cDNA-protein conjugate; because the high speed careening of the cDNA display library is performed.

It is preferable to obtain CDR3 cluster of VHH that contains at least 10 different peptide sequences. Here, it is preferable that the CDR3 cluster of VHH having at least 10 different peptide sequences is selected from the group consisting of SEQ ID NO. 24 to 33.

The linker has a backbone and a side chain; wherein the background comprises (p1) a solid phase binding site at which the linker is bound to a solid phase, (p2) a cleavage site at which the linker is cleaved from the solid phase, (p3) mRNA binding site being composed of 3-cyano-vinylcarbazole closed to 3' terminal or near thereof; the side chain comprises (s1) a backbone binding site, (s2) a spacer having a fluorescence label binding site for the backbone, (s3) a fluorescent label for the backbone binding to the fluorescent label binding site for the backbone, and (s4) puromycin as a peptide binding site. It is preferable that the cleavage site is arranged in said solid phase binding site, because mRNA is ligated to the linker without enzyme by using photocrosslinking, and it shorten synthesis period of the linker.

The spherical shape structure preferably comprises the following combination, because the sorting is carried out by using the fluorescent labels matching to purposes: (1) the positive spherical shape conjugate with a fluorescent label, the negative spherical shape conjugate without the label, and the target detecting molecule without the label; (2) the positive spherical shape conjugate with the fluorescent label, the negative spherical shape conjugate with the label having different fluorescence from that of the positive spherical shape conjugate, and the target detecting molecule without the label; (3) the positive spherical shape conjugate without the fluorescent label, the negative spherical shape conjugate with the label, and the target detecting molecule with the label having different fluorescence from that of the label; and (4) the positive spherical shape conjugate without the fluorescent label, the negative spherical shape conjugate without the label, and the target detecting molecule with the label having different fluorescence from that of the label.

For example, when the concentration of the mRNA/cDNA-protein conjugate chosen by the screening is low, (1) may be selected. When the concentration thereof is high, (2) may be chosen. Further, positive spherical shaped conjugate with the fluorescent label preferably comprises the mRNA-protein conjugate or the target molecule to be bound thereto on the surface thereof, and encapsulate the fluorescent label; because it gives high accuracy to the sorting and makes possible to conduct efficient screening of the cDNA display molecule or nucleic acid aptamer.

Further, the fluorescent label is preferably any one of selected from the group consisting of Alexa Fluor 594, Fluorescein Amine, FITC, Rhodamine, mCherry2 and Quantum Dot, because they may be used for gene expression and multiple labelling. Furthermore, as the label expresses different fluorescence from these fluorescent labels, it preferable any one of the fluorescent intercalator selected from the group consisting of SYBR Gold, SYBR Green and Quantum Do, because they may conveniently label the target detection molecule, and they are suitable for cell sorting.

The separation is preferably conducted by using, for example, 2 fluorescent labels excited by using 2 different wavelengths; and the special shape conjugate on which the fluorescent label excited with both of 2 different wave length is only separated by using the cell sorter, because of improving the accuracy of the screening. Also, the separation is preferably further conducted by co-existing with a particular polypeptide to apply selection pressure, because of improving the accuracy of the screening higher.

The term "antibody," as used herein, comprises: immuneglobulins such as IgA, IgD, IgE, IgG, and IgM, which are produced by an antibody-producing cell, responsible for humoral immunity; a heavy-chain antibody; a single-chain antibody; a ScFv; a single domain antibody comprising CDR3 in the heavy-chain antibody, which is sometimes referred to as a "VHH" or a "VHH antibody"; an aptamer which is capable to bind a foreign body such as a pathogen invaded to human body; and partially modified or altered thereof. The term "CDR3 cluster," as used herein, is defined as at least 80% sequence identity in the population using the sequence clustering program CD-HIT (Cluster Database at High Identity with Tolerance).

Advantageous Effect

Conventionally, it takes time and labor for screening the cDNA display library or the nucleic acid aptamer library to condense and select them by using the column, the capillary zone electrophoresis, and the atomic force microscope. According to the high-speed in vitro screening method of the present invention, cDNA display molecule or the nucleic acid aptamer of the object is conveniently screened from a cDNA display library or a nucleic aptamer library having a size equal to or more than $10^{10}$, preferably having a size equal to or more than $10^{10}$ or equal to or less than $10^{14}$, by binding the fluorescent label to the spherical structure to conduct the high-speed selection.

BRIEF DESCRIPTION OF THE DRAWINGS

FIG. 2C is the drawing showing the procedures of the high-speed screening by using both of the spherical shaped structure P and N (1).

FIG. 2D is the drawing showing the procedures of the high-speed screening by using both of the spherical shaped structure P and N (2).

EMBODIMENT FOR CARRYING OUT THE INVENTION

Figure 1A:
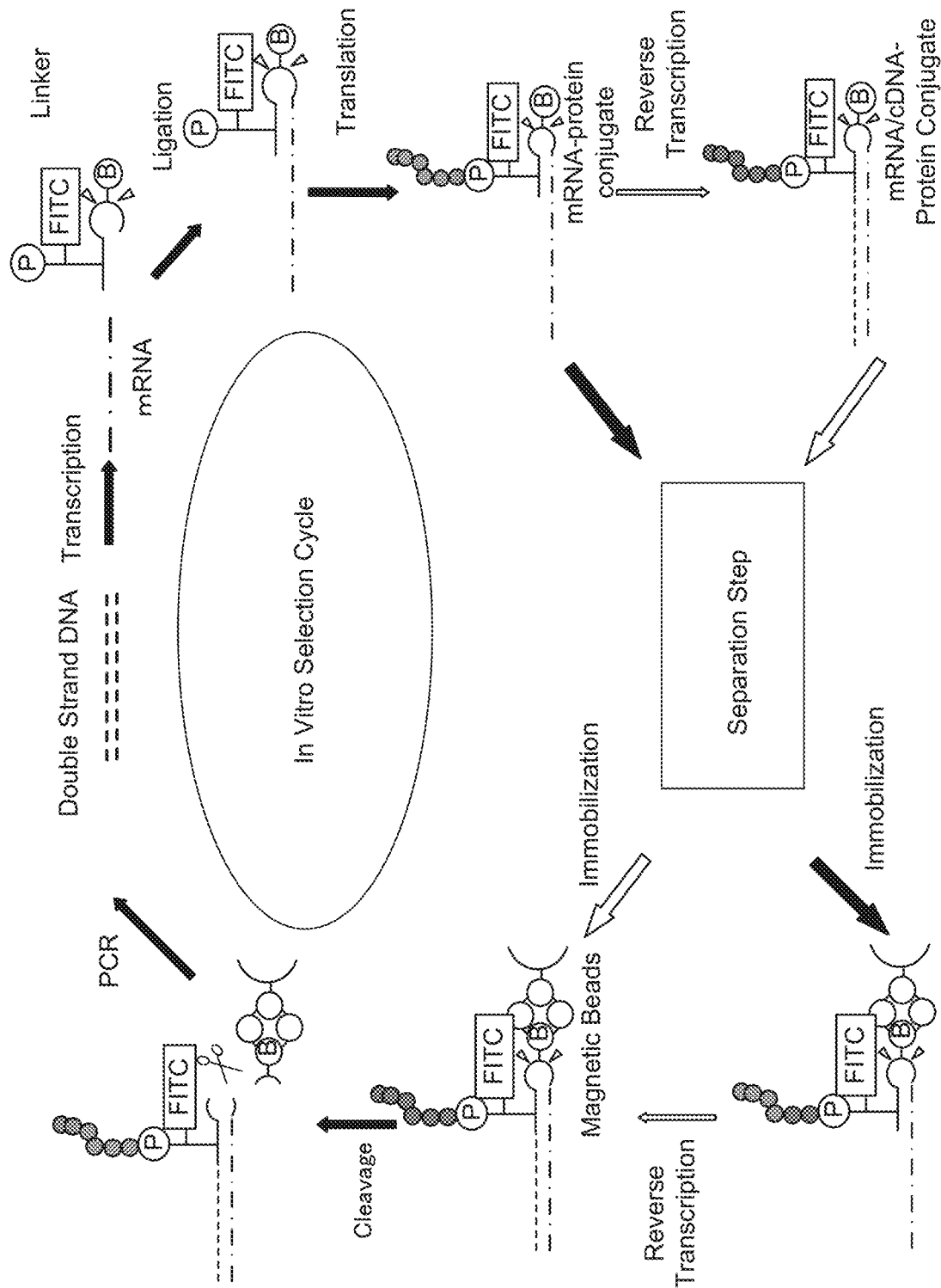
FIG. 1A is a drawing showing the screening procedure of cDNA display method in vitro.

Hereinbelow, the present invention is explained in detail, referring to FIGS. 1A to 2D, and 6 to 9.

As described above, the present invention is a method of identifying antibody CDR3 clusters using a high-speed screening method of either cDNA display library or the aptamer library, both of which compose the library for the present invention. The method comprises the following steps (i) preparing a spherical shaped structure P or N from a spherical shaped molecule;

(ii) preparing the spherical shaped conjugate P to which the target detecting molecule is bound or the spherical shaped conjugate N from the spherical shaped structure P obtained in the step described above;

(iii) separating the spherical shaped conjugates obtained in the step described above using a fluorescence cell sorter;

(iv) selecting the separated positive and negative spherical shaped conjugates at least 1 time and then eluting the selected conjugates to obtain an eluted sample;

(v) amplifying a nucleic acid in the eluted sample to obtain PCR products;

(vi) separating the PCR products using the fluorescence cell sorter; and (vii) conducting amplicon sequencing for CDR3 cluster analysis to identify the antibody CDR3 clusters.

As the spherical shaped molecules employed in the step, it may be used those as long as they are acceptable for the separation by using the cell sorter and is not limited. For example, there are mentions such as the liposomes being composed of lipid bilayer, the Sepharose beads, the silica beads, then latex beads, dextran beads, chitosan beads, polystyrene beads and the like. The liposomes, the Sepharose beads, the silica beads, the latex beads may be preferably employed.

The diameters of the beads are preferably between 0.5 μm to 20 μm for accurate determination. Control of the liposome diameter is difficult. However, the spherical shaped beads having even diameter distribution are prepared by coating the beads surface with the liposome in the conventional method. Such beads improve the accuracy of the separation by using the cell sorter.

Also, the spherical shaped molecule may include the labels such as Alexa Fluor 594, Fluorescein Amine, FITC, Rhodamine, mCherry2, Quantum Dot and the like in their inside. They may include magnetized material such as magnetite and the like. Further, such beads may have colored outside such as blue, red, green, black and the like. The spherical shaped molecule is usually not porous, however, they may be porous. Their surfaces are preferably modified with functional groups such as carboxyl, amino, hydroxyl, thiol and the like, because it makes them to bind the protein on the mRNA-protein conjugate or the mRNA/cDNA-protein conjugate easy.

As such spherical shaped molecule, commercially available ones may be purchased, or, for example, the liposome may be prepared as follows.

The liposome (hereinbelow, it is sometimes referred to as, "vesicle".) is mainly prepared by suing W/O emulsion method, and it is prepared as follows. Firstly, phospholipid as the raw material for the liposome is solved in organic solvent such as alcohols, chloroform and the like to prepare lipid solution. Then, it is poured into glass wears such as test tubes and the like, subsequently, thin film is formed on the inner surface of them, volatizing such organic solvents.

Next, oil is added into the glass wear to solve the thin film of phospholipid formed on the inner surface of them. Then, aqueous solution that becomes internal fluid of the liposome is added into the wear and mixed well to prepare oil-water mixture. The oil water mixture is gently poured into the aqueous solution, which becomes the outer fluid of the vesicle; and then the mixture is stood for a while, and subject to the centrifugation. By the operation described above, droplets coated with phospholipid single layer are passed through the phospholipid single layer formed at interface of the oil and the solution to obtain the liposome. In general, the size of the substances such as cell or others to be separated by using the cell sorter is knows as those from about 0.5 μm to 20 μm. Therefore, it is preferable to for preparing the liposome having such sizes.

When the liposome is manufactured, as the internal fluid of the liposome, it is preferable to employ the solution including the fluorescence label molecule, because the objective liposome is accurately separated in the separation step by using the cell sorter explained in later. Such fluorescence label is not particularly limited, as long as they are employed in the cell sorter. It is more preferable to employ that selecting from the group consisting of Alexa Fluor 594, FITC, Rhodamine, mCherry2 and Quantum Dot, because they make the confirmation of the gene expression easy, and they may be used for multi-labeling.

When the liposome is labeled with the fluorescence label included therein, the liposome membrane is preferably modified by using the following proteins or peptides; because the objective liposome is accurately separated in the separation step by using the cell sorter explained in later. As the modification peptides, there are mentioned, for example, peptide molecule to be anchored onto the liposome membrane, the fluorescent protein, a variety of antibodies, the fused protein having the coding sequence for other biomolecules such as the marker protein of the disease and the like.

Also, since the liposome is not labeled with the fluorescent label, it is preferable for the labeled target molecule, which is capable of binding to the mRNA/cDNA-protein conjugate, on the liposome surface; because the objective liposome is accurately separated in the separation step by using the cell sorter explained in later. In this case, the liposome may be labeled with the fluorescence label as described above or intercalator. Such intercalators are not particularly as long as they are commonly used. It is preferable to use any one of the fluorescent molecules selected from the group consisting of SYBR Gold, SYBR Green and Quantum Dot, because they are obtained easily and their fluorescent intensity.

Figure 2A:
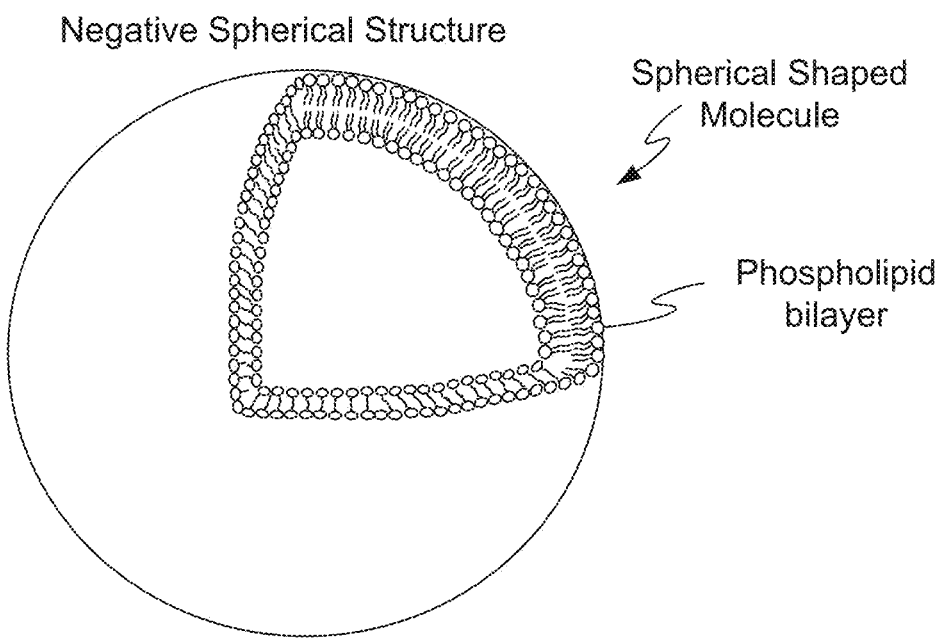
FIG. 2A is the drawing showing the negative spherical structure (hereinbelow, it is sometimes referred to as the "spherical shaped structure N".).
Figure 2B:
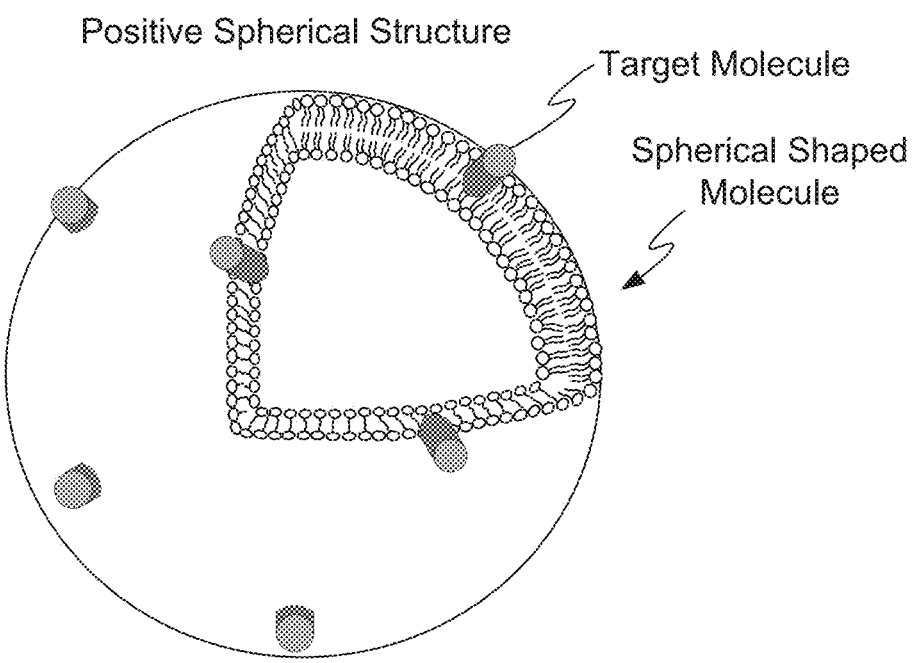
FIG. 2B is the drawing showing the positive spherical structure (hereinbelow, it is sometimes referred to as the "spherical shaped structure P".).

The target molecule to be immobilized on the spherical shaped molecule is chosen considering the combination with the target detection molecule bind thereto and prepared. Here, the target detection molecule is defined as the molecule that capable of binding to the target molecule immobilized on the spherical shaped molecule. The spherical shaped molecule with the bound target molecule is referred to as the positive spherical structure (spherical shaped structure P; FIG. 2A), and that without the bound target molecule is referred to as the negative spherical structure (spherical shaped structure N; FIG. 2B).

For example, when the target detection molecule is the RNA aptamer to bind streptavidin, or biotin is bound to the target detection molecule, streptavidin is chosen as the target molecule to prepare the spherical shaped conjugate P or the conjugate N. As the spherical shaped molecule to which the target molecule is bound, if the spherical shaped molecule of which surface is modified with the carboxyl group is used, the carboxyl group is activated with N-hydroxy succinimide (NHS) to form NHS ester. After that, it is reacted with streptavidin to form amide binding between the NHS ester and amino group in streptavidin to immobilized streptavidin on the spherical shaped structure. Other than that, commercially available spherical shaped molecule such as the silica beads or latex beads surface-modified streptavidin may be used. The spherical shaped structure P and the spherical shaped structure N thus obtained are subjected to the next step.

Next, in the spherical shaped conjugate formation step (ii), the spherical shaped structure P or the spherical shaped structure N obtained in the spherical shaped structure preparation step is reacted with the target detection molecule (FIG. 2C).

In the present specification, the target detection molecule is defined as the nucleic acid obtained by using cDNA display method, nucleic acid derivative peptide and those to which the linker is bound, or the nucleic acid aptamer manufactured on the basis them (FIG. 1A). The nucleic acid contains a single strand oligo DNA, double strand DNA and RNA. Also, the nucleic acid derivative contains the target molecule, for example, RNA aptamer binding to streptavidin and the like. The conjugate of the nucleic acid and the linker contains, for example, the mRNA-protein conjugate explained later, the mRNA/cDNA-protein conjugate, and the like.

When the cDNA library is used, it is preferable to comprise the steps of (a) preparing mRNA to be used in cDNA display method, (b) binding mRNA to the linker by photo-crosslinking, (c) binding the protein translated from mRNA to the mRNA-linker to form the mRNA-linker-protein conjugate formation step, (d) conducting the reverse transcription of mRNA of the mRNA-linker-protein conjugate to from the mRNA/cDNA-linker-protein conjugate; because the desirable mRNA, cDNA and the like are obtained by using cDNA display method.

Both of the spherical shaped molecule and the target detection molecule are prepared so as to become the predetermined concentration in the predetermined binding buffer to bind them. For example, they are reacted in the buffer between about 4° C. to about 30° C. for about 0.5 hour to about 3 hours.

In the spherical shaped conjugate separation step of (iii), firstly, both of the spherical shaped conjugate P and N obtained in the above-mentioned step are prepares so as to be the predetermined concentration in the predetermined solution. Next, they are sorted by using the commercially available cell sorter according to the instruction attached thereto to separate the objective spherical shaped conjugate (FIG. 2D). For example, when the liposome is used as the spherical shaped molecule, the fluorescent liposome (hereinbelow, it is sometimes referred to as "fluorescent liposome") with the fluorescence label is selectively obtained on the basis of the fluorescent intensity from the fluorescent label in the liposome, or the fluorescent label, which is, for example, intercalator, bounds to the target detection molecule, which is, for example, mRNA/cDNA-protein conjugate.

By using the fluorescence label for the liposome and that emitting the fluorescence of the different wavelength for the target detection molecule, the spherical shaped conjugate having the fluorescent labels excited with the different two exciting wavelengths are solely separated. Then, such separation enables to improve the sorting efficiency, and to obtain the fraction containing the spherical shaped conjugate with the desirable target molecule in higher content.

Also, the target binding molecule and the molecule causes competitive inhibition to them are coexisting together in the solution to apply selection pressure. By this, the fraction containing the spherical shaped conjugate, which has higher amount of the desirable target molecule on it, is obtained.

Table 1 shows the combination of the spherical shaped structure and the target detection molecule. In the figure, "the spherical shaped structure P" and the "spherical shaped structure N" are as described above. Label 1 and 2 shows different ones respectively. The target detection molecule is the linker-nucleic acid molecule (C) selected by using the cDNA display method from the cDNA library, or the aptamer molecule included in the nucleic acid aptamer library (A).

TABLE 1

| Group | Spherical structure Type | Target molecule | Label 1 | Label 2 | C/A | Target detection molecule Label 1 | Label 2 |
|---|---|---|---|---|---|---|---|
| P11 | Spherical shaped structure P | ○ | ○ | x | ○ | x | ○ |
| P12 | Spherical shaped structure P | ○ | x | ○ | ○ | ○ | x |
| P13 | Spherical shaped structure P | ○ | ○ | x | ○ | x | ○ |
| P14 | Spherical shaped structure P | ○ | x | ○ | ○ | ○ | x |
| P15 | Spherical shaped structure P | ○ | ○ | x | ○ | x | ○ |
| P16 | Spherical shaped structure P | ○ | x | ○ | ○ | ○ | x |
| P17 | Spherical shaped structure P | ○ | ○ | x | ○ | x | x |
| P18 | Spherical shaped structure P | ○ | x | ○ | ○ | x | x |
| P19 | Spherical shaped structure P | ○ | x | x | ○ | ○ | x |
| P20 | Spherical shaped structure P | ○ | x | x | ○ | x | ○ |
| N11 | Spherical shaped structure N | x | ○ | x | ○ | x | ○ |
| N12 | Spherical shaped structure N | x | x | ○ | ○ | ○ | x |
| N13 | Spherical shaped structure N | x | ○ | x | ○ | x | ○ |
| N14 | Spherical shaped structure N | x | x | ○ | ○ | ○ | x |
| N15 | Spherical shaped structure N | x | ○ | x | ○ | x | ○ |
| N16 | Spherical shaped structure N | x | x | ○ | ○ | ○ | x |
| N17 | Spherical shaped structure N | x | ○ | x | ○ | x | x |
| N18 | Spherical shaped structure N | x | x | ○ | ○ | x | x |
| N19 | Spherical shaped structure N | x | x | x | ○ | ○ | x |
| N20 | Spherical shaped structure N | x | x | x | ○ | x | ○ |

In Table 1, "○" means "bound", and "x" means "not bound".

When the liposome is employed, the liposome including the fluorescent substance is purified by removing the aggregates of the phospholipid, which is not used to form the liposome, from the fluorescent liposome fraction manufactured and fractionated according to the conventional method, for example, by using the centrifugation.

By using the purified liposome, the positive liposome conjugate which is bound to the target molecule (hereinbelow, it is sometimes referred to as LiBP), and the negative liposome conjugate which is not bound to the target molecule (hereinbelow, it is sometimes referred to as LiBN) are respectively prepared. Then, they are reacted with the target detection molecule by using the method described above. Subsequently, they are separated by using a cell sorter. The separation of the liposome is finished from about 0.1 to about 6 hours, although it is slightly different depending on the cell sorter apparatus to be used.

Also, after the separation step, depending on the conventional method, mRNA in the mRNA-protein conjugate is reverse-transcribed to obtain mRNA/cDNA-protein conjugate. Concretely, for example, mRNA-protein conjugate as described above is immobilized on the magnetic beads such as styrene beads; and then they are subjected to the reverse transcription. It is preferable to conduct such reverse transcription before the amplification step described below, because it enables to purify mRNA/cDNA-protein conjugate effectively.

After that, the magnetic beads are washed with the desirable washing buffer, and then, the releasing agent of the mRNA/cDNA-protein conjugate such as an enzyme is added and incubated to obtain the released mRNA/cDNA-protein conjugate at the cleavage site in the linker. Then, it is preferable to purify the released mRNA/cDNA-protein conjugate by using the tag for protein purification such as His-tag and the like.

In the amplification step (iv), DNA contained in the mRNA/cDNA-protein conjugate (the target detection molecule) on the spherical shaped conjugate obtained as described above is amplified by using PCR according to the conventional method. When the target detection molecule is RNA, it is subjected to the reverse transcription to prepare cDNA. For example, firstly, the mRNA/cDNA-protein conjugate is precipitated by using a co-precipitating agent such as ethanol to obtain cDNA. The obtained cDNA is added to the desirable PCR reaction mixture to be amplified according to the desirable PCR program. The steps (i) to (iv) are repeated by using the amplified DNA to obtain the DNA having the desirable sequence from the initial DNA library by using the high-speed screening. For the high-speed screening of DNA, it is preferable to repeat the steps (i) to (iv) not more than 10 times; because it makes possible to converge DNAs contained in the library having $10^{11}$ order to several tens order. It is more preferable to set the repeat numbers not over than 5, furthermore preferable to set it not over than 3 from the view point of cost performance.

Figure 6:
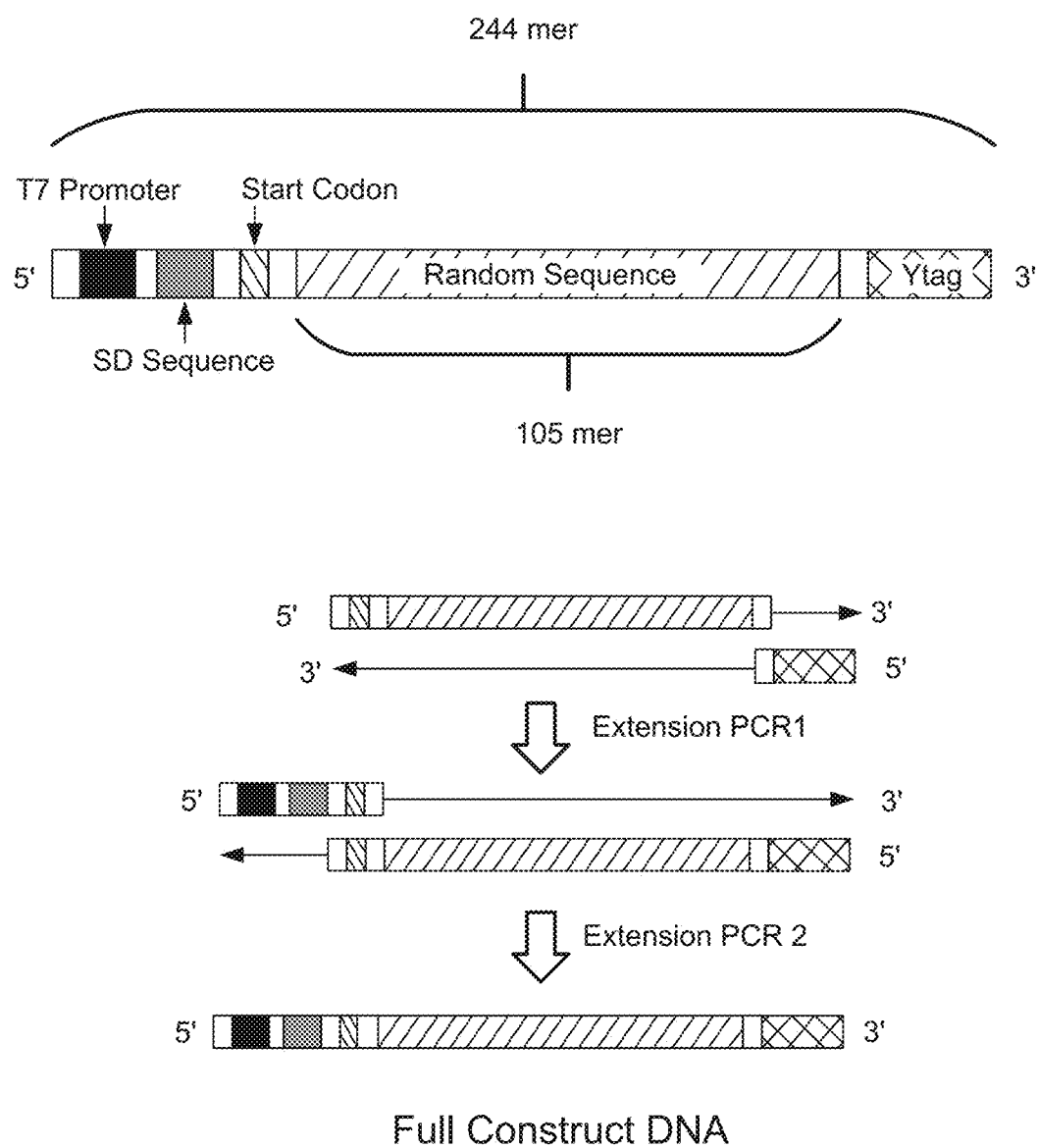
FIG. 6 is the schematic figure showing the extension PCR to manufacture the conjugate of promoter-DNA (244 mer).

Also, among the cDNA display method comprising the steps (a) to (d), in the mRNA preparation step (a), the promoter and other necessary sequences for constructing a full construct are bound to a certain number of the selected DNA to construct a full construct DNA to prepare mRNA of the full construct DNA (FIG. 6). Here, as the "promoter", there are mentioned, for example, such as T7 promoter, SP6, T3 promoter, and the like. It is preferable to employ T7 promoter from the view point of versatility. Also, as the term, "other necessary sequences for constructing a full construct", there are mentioned such as the liposome binding sequence, tag sequence for purification such as His-tag, Strep-tag and the like, when liposome is employed as the spherical structure. The double strand full construct DNA (hereinbelow, it is sometimes referred to as "promoter-DNA conjugate".) is obtained by preparing DNA fragment containing the sequence described above, and extending thereof with extension PCR to amplify them.

Also, the obtained promoter-DNA conjugate is subjected to the transcription according to the conventional method. Here, by using the kit for transcription such as Scrip TMAX (R) Thermo T7 Transcription Kit (TOYOBO Co. Ltd.), RiboMAX™ Large Scale RNA Production System-T7 (Promega), T7 Transcription Kit (Cosmo Bio Co., Ltd.) and other commercially available transcription kit, mRNA is quickly and conveniently prepared with high accuracy.

In the subsequent linker binding step (b), mRNA obtained as described above is bound to the cDNA display linker to prepare a linker-mRNA conjugate. Since the high-speed screening needs shorten ligation time between the linker and mRNA, it is preferable to employ the linker that enables short time ligation of them. Since such short time ligation is preferably conducted by using photo-crosslinking, photo-crosslinking type linker is preferably used. As the photo-crosslinking type linker, a linker comprises the photo-crosslinking type artificial nucleic acid (3-cyano-vinyl carbazole) (hereinbelow, it is sometimes referred to as "cnvK") in its backbone is preferable, because it enables to obtain the linker-mRNA conjugate quickly and conveniently.

Concretely, the backbone of the linker comprises (p1) a solid phase binding site at which the linker is bound to the solid phase, (p2) a side chain binding site for binding the side chain, (p3) the backbone having the mRNA binding site, (p4) a cleavage site at which the linker is cleaved from the solid phase. The side chain comprises (s1) a backbone binding site at which it is bound to the backbone, (s2) a label binding site for binding a detection label for the mRNA-linker-conjugate, (s3) a peptide binding site to which a peptide having a sequence corresponding to that of mRNA. Then, cnvK is located between the cleavage site on the backbone and the side chain binding site. Also, the label binding site of the side chain may be composed of at least one spacer sequence, and fluorescence label is bound thereto. Further, the peptide binding site may be composed of puromycin or its derivatives.

Since the linker has the structure described above, it ligates to mRNA and in a short time not over than $\frac{1}{30}$, comparing to that T4 RNA ligase is employed. Such short time ligation greatly reduces a risk that RNase degrades mRNA. Also, by utilizing the label bound to the side chain of the linker, the linker-mRNA conjugate is easily separated.

Note that the linker-mRNA conjugate as described above may be prepared by using enzyme ligation procedure, which employs both of the conventionally using the linker and mRNA obtained as described above, and they are ligated with an enzyme such as T4 RNA ligase and the like.

Next, in the mRNA-protein conjugate formation step (c), the linker-mRNA conjugate obtained as described above is translated by using cell free translation system to display the peptide having the sequence corresponding to mRNA on peptide binding site of the linker to from mRNA-linker-protein conjugate. As the cell free translation system, commercially available lysate of reticulocytes such as those of rabbit is preferable, because it gives speedy translation and stable results.

The peptide bounds to the peptide binding site in the linker, included in the mRNA-protein conjugate (the target detection molecule) obtained in the step (c) or the mRNA/cDNA-protein conjugate obtained in the step (d) described later, binds to the target molecule on the spherical structure or directly binds to the functional group on it. By this, the spherical shaped conjugate is obtained.

The step for conducting reverse transcription of the mRNA-protein conjugate to obtain mRNA/cDNA-protein conjugate may be conducted prior to the separation step (iii) or after it. It is preferable to conduct the step for conducting reverse transcription is conducted prior to the separation step (iii), because it makes mRNA bound to the linker stable. Concretely, in the reverse transcription step (d), the reverse transcription of the mRNA-protein conjugate in the spherical shaped conjugate is conducted under the predetermined conditions. Namely, the condition of the reverse transcription may be set optionally. For example, according to the conventional method, dNTP mixture, DTT, reverse transcriptase, and RNase deleted water (hereinbelow, it is sometimes referred to as "RNase free water".) are mixed to prepare the predetermined reaction system. Then, the reverse transcription may be conducted at the predetermined temperature and time. The reverse transcription may be conducted according to the protocol attached to the commercially available kit such as PrimeScript RT-PCR Kit (Takara Bio Inc.), ReverTra Ase (TOYOBO Co. Ltd.) and the like. When the reverse transcription step is conducted after the separation step (iii) is explained later.

Hereinbelow, the present invention is explained in detail, illustrating the liposome as the spherical structure, T7 promoter, Cap sequence, Q sequence, Kozak sequence, His-tag sequence, and the DNA sequence coding the desirable peptide are used.

(1) Preparation of the Promoter-DNA Conjugate

DNA fragment having the desirable sequence may be synthesized according to the conventional method. For example, firstly, the PCR reaction mixture containing the sequence coding the peptide sequence and the DNA fragment having His-tag is prepared, and then extension PCR is conducted under the desirable conditions. After that, PCR reaction mixture containing T7 promoter sequence-Cap sequence-Ω sequence-Kozak sequence is added into the PCR product, and then the extension PCR is conducted under the desirable conditions to obtain the DNA having the objective sequence.

For example, 25 to 75 µL of the PCR reaction mixture (1× PrimeSTAR buffer ($Mg^{2+}$), 0.1 to 0.4 mM dNTPs, 0.01 to 0.04 U/µL PrimeSTAR HS DNA polymerase (Takara Bio Inc.)) containing both of the sequence coding the desirable peptide and that having His-tag is prepared, and then overlap extension PCR 1 is conducted by using the following PCR program. The PCR contains, for example, (a) at 92 to 96° C. (1 to 3 minute), (b) at 92 to 96° C. (5 to 45 second), (c) at 50 to 70° C. (2 to 30 second), (d) at 65 to 80° C. (20 to 40 second), and (e) at 65 to 80° C. (1 to 3 minute); it preferable to repeat the steps (b) to (d) for 6 to 10 times, because the sufficient amount of the amplification products are obtained.

Next, the PCR products obtained in the overlap extension PCR 1 is added into 25 to 75 µL of PCR reaction mixture (It contains the sequence consisting of T7 promoter sequence-Cap sequence-Q sequence-Kozak sequence. It is the same as that used in the overlap extension PCR 1 except it further contains 0.6 µM F1) to set the total amount to 50 to 150 µL. Then, the overlap extension PCR 2 is conducted by using the following PCR program. It is preferable to use the same PCR grogram as that described above, because sufficient amount of the amplification products is obtained.

Double strand full construct DNA obtained from the overlap extension PCR 2 is, for example, precipitated by using a co-precipitant (Quick-Precip Plus Solution, EdgeBio), and then it is preferable to purify by using, for example, FavorPrep PCR Clean-Up Mini Kit (Favogen).

Similar to this, extension PCR is conducted by using a random sequence containing DNA designed so as to be coded the desirable peptide, the sequence containing both of T7 promoter and SD sequence, and Ytag sequence to obtain the double strand full construct DNA. In this case, firstly, the PCR reaction mixture comprising the random sequence and Y tag sequence is prepared, and then extension PCR is conducted under the desirable conditions. It is preferable to use the same PCR program except the steps (b) to (d) are conducted 4 to 10 cycles, because the sufficient amount of the amplification products is obtained.

After that, the PCR reaction mixture comprising the T7 promoter-SD sequence is added to the obtained PCR products to conduct extension PCR under the desirable conditions to obtain the DNA having the objective sequence. It is preferable to use the same PCR program except the steps (b) to (d) are conducted 4 to 10 cycles.

(2) Preparation of mRNA

DNA as described above is used as a template DNA, transcription is conducted according to the conventional method. For example, the reaction mixture comprising the predetermined concentration of the T7 transcription buffer, rNTPs (mixture of 25 mM ATP, CTP, UTP, and GTP each), an enzyme mixture, and the template DNA is reacted at about 37° C. for about 2 to 6 hours. Then, RQ-1 RNase-Free DNase (Promega) is added to the reaction mixture, and further reacted at about 37° C. for about 15 to 30 minutes. After the termination of the reaction, the purification is conducted by using, for example, Rneasy minElute Cleanup kit (QIAGEN) to obtain purified mRNA.

Such transcription may be conducted by using the commercially available transcription kit. For example, it is preferable to use RiboMAX Large Scale RNA Production Systems-T7 (Promega), because the transcription is conducted quickly, conveniently and accurately. When such kit is employed, transcription is conducted by using 0.5 to 5 µg of dsDNA in the scale of 10 to 30 µL according to the protocol attached to the kit. Transcription is conducted under the desirable conditions by incubating the reaction mixture, and the desirable amount of DNase is added into it and again incubated in the constant temperature water bath to obtain mRNA.

Also, for example, it is preferable for obtaining mRNA by using aluminum block for the constant temperature water bath (Anatech, Cool Stat 5200), the reaction mixture is incubated at about 35 to 40° C., for 1 to 3 hours, and then, 0.5 to 2 µL of RQ1 DNase attached to the kit is asses into the sample and incubated are about 35 to 40° C. for 5 to 30 minutes, because of the synthesis efficiency. The obtained mRNA may be purified by using the desirable kit. As the purification lit, for example, After Tri-Reagent RNA Clean-Up Kit (Favogen) may be used.

(3) Preparation of mRNA-Linker-Conjugate (3-1) Preparation of the Linker

In the present specification, the term, "linker", is defined as the liker which is employed for generating any one of the linker-mRNA conjugate, the linker-mRNA-protein conjugate, or the linker-mRNA/cDNA-protein conjugate (hereinbelow, it is sometimes referred to as "IVV".) used in the cDNA display. Also, the term, "mRNA-protein conjugate", is defined as the linker-mRNA-peptide conjugate. The linker-mRNA conjugate is translated, to which the peptide having the sequence corresponding to that of mRNA is bound at the peptide binding site on the linker. Further, the term, "mRNA/cDNA-protein conjugate", is defined as the linker-mRNA/cDNA-peptide complex, which is formed by the reverse transcription of the mRNA-protein conjugate, and cDNA is bound on the backbone of the linker.

The linker is mainly composed of DNAs; however, it is preferable for containing cnvK, because it forms cross-link with mRNA in short time. Also, it may contain DNA analogue such as deoxy inosine, biotin-modified deoxy thymine, Fluorescein-modified doxy thymine and the like. It is preferable for the linker to be designed having flexibility and hydrophilic property.

As the molecule forms the binding to the solid phase, for example, it is preferable biotin or its derivatives when avidin, streptavidin and the like are bound on the solid phase; maltose when the maltose binding protein is bound thereto; guanine nucleotide when G protein is bound thereto; metal such as Ni, Co, and the like when poly histidine peptide is bound thereto; glutathione when glutathione S-transferase is bound thereto.

There are mentioned such as DNA or RNA having specific sequence when the sequence-specific DNA or RNA binding protein is bound thereto; the antigen or the epitope when the antibody or the aptamer is bound; calmodulin binding peptide when calmodulin is bound thereto; ATP when the ATP binding protein is bound thereto; estradiol and the like when estradiol receptor protein is bound thereto. Among them, it is preferable to use biotin, maltose, metals such as Ni and Co, glutathione, antigen molecule. From the view point of easy synthesis of the linker, it is preferable to use biotin or derivatives thereof.

The solid phase binding site (p1) is defined as the site for binding at which either of the mRNA-protein conjugate or mRNA/cDNA-protein conjugate described is attached through the linker. The solid linker binding site (p1) is composed of at least 1 to 10 nucleotides. For example, it is preferably composed of any one of the compound selected from the group consisting of the biotin-modified deoxy thymidine (dT), biotin, streptavidin, alkynes, azide compounds obtained through click chemistry, amino group, N-hydroxy succinimide ester (NHS), SH group, and Au; and poly A bound to thereof. It is preferable for the poly A, which is composed of at least 10 adenines are bound, because such structure enables to maintain the distance from the solid phase properly to release the linker smoothly. It is more preferable for it being composed of about 20 of adenine is bound.

The side chain binding site (ps), which is located close to 3' terminal of the linker, it the site to which the side chain explained later is bound. Also, for example, when the side chain binding site (p2) of the linker is composed of Amino-Modifier C6 dT, the side chain and the backbone is cross-linked by using EMCS as the 5' terminal of the side chain is 5'-Thiol-Modifier C6.

The primer region (PR) is located at 3' terminal side of the linker adjacent to the 3' side of the side chain binding site, and it functions as a primer for reverse transcription, when reverse transcription is conducted on the linker. Here, the primer region (PR) functions as the primer for reverse transcription, when reverse transcription is conducted on the linker. The region is preferably composed of about 1 to 15 nucleotides, and more preferably composed of 3 to 5 nucleotides. Since the nucleotide number is more than 15, the binding efficiency as the linker is reduced, the region is preferably composed of the nucleotide number as described above, from the viewpoints both of the binding efficiency with the linker and reaction efficiency as the primer.

The peptide binding site is preferably composed of puromycin or its derivative. As the puromycin derivatives, 3'-N-aminoacyl puromycin (PANS-amino acid), or nucleoside such as 3'-N-aminoacyl adenosine amino acid (AANS-amino acid) may be used. It is more preferable to use a compound selected from the group consisting of PANS-Gly having glycine as the amino acid portion of PANS, PANS-Val having valine as that of PANS, PANS-Ala having alanine as that of PANS, a mixture of PANS amino acids, AANS-Gly having glycine as the amino acid portion of AANS, AANS-Val having valine as that of AANS, AANS-Ala having alanine as that of AANS, and the mixture of AANS amino acids.

As PANS-amino acids, there are mentioned, for example, PANS-Gly, PANS-Val, PANS-Ala and the like, and as AANS-amino acids, there are mentioned, for example, AANS-Gly, AANS-Val, AANS-Ala and the like. Also, the compounds composed of the nucleoside and the amino acid via ester bonding may be used. However, it is most preferable to use puromycin, because it gives high stability to the peptide bonding at the peptide binding site.

The side chain has the fluorescent group between the peptide binding site and the side chain binding site. By this, it becomes easier to detect the binding with or without the linker in each step of cDNA display explained later. It is preferable for fluorescent group to employ the fluorescent compound, for example, which has a free functional group such as carboxyl group being change to active ester, hydroxyl group being changed to phosphoramidite, or amino group, and enables to bind to the linker as the labeled nucleotide. As such fluorescent compound, there are mentioned, for example, such as fluorescein thiocyanate (FITC), rhodamine, Cy dye, Alexa Fluor and the like. It is preferable to use FITC, because of the lower cost.

Figure 7:
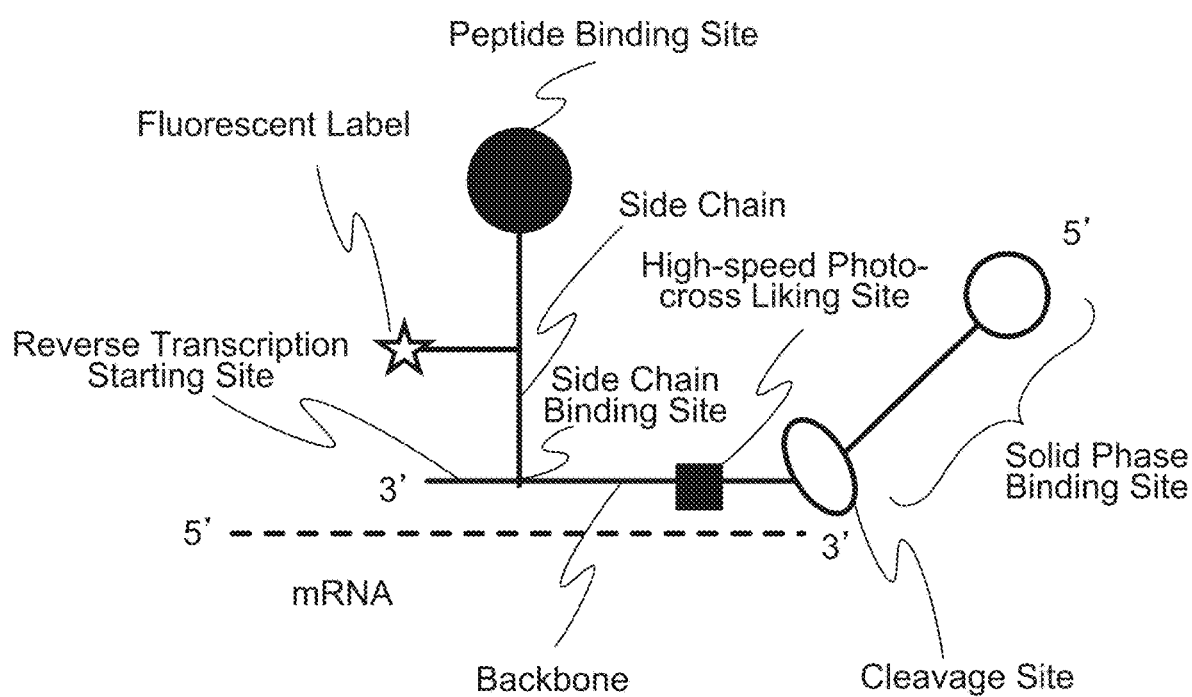
FIG. 7 is the schematic figure showing a photo-crosslinking type linker.

The present invention preferably uses the photo-crosslinking type linker (FIG. 7). When the enzyme such as T4 RNA ligase is used to bind the backbone and mRNA, mRNA is often degraded, because complete removal of RNase is impossible, and it takes long time to bind them. However, since the present invention does not use the enzyme for binding of the linker, it makes the degradation of mRNA avoidable. Further, since the linker of the present invention contains cnvK, mRNA and the linker are cross-linked in water, not buffer, in very short time by using UV radiation. Also, the structure of the cross-linked linker is as described above.

It is preferable for the solid phase cleavage site (p2) being composed of deoxy inosine because of the following reasons. In order to cleave the two conjugates from the solid phase, endonuclease V is used, wherein namely, the conjugate of the present linker-mRNA and cDNA, or that of the present linker-mRNA/cDNA and peptide (hereinbelow, it is sometimes correctively referred to as "fusant".) explained later. The solid phase cleavage site being composed of deoxy inosine gives specific cleavage the solid phase with the solid phase binding site.

The photo-crosslinking linker may be prepared as follows.

Firstly, the backbone of the linker of the preset invention, poly A+cnvK segment, is designed so as to have cnvK at the desirable position between the solid phase binding site and the side chain binding site on the backbone, DNA is chemically synthesized according to the conventional method. Such chemical synthesis of the DNA chain may be entrusting to companies conducting these syntheses.

The backbone is designed so as to comprise the reverse transcription starting site as shown in FIG. 7, the reverse transcription starting site, the side chain binding site, the high-speed photo-crosslinking site being composed of 3-cyano-vinylcarbazole, and the solid phase binding site. In the backbone shown in FIG. 7, the nucleotide sequence other than modified site is shown as the following sequence (SEQ. ID NO. 1). To the following backbone, BioTEG is attached at the 5' terminal. Also, in the following nucleotide sequence, R represents inosine and Y represents amino C6-dT.

[SEQ. ID NO. 1]
5'AAAAAAAAAAAAAAAAAAAANTTCCAGCCGCCCCCCGNCCT 3'

The side chain of the linker (hereinbelow, it is sometimes referred to as "puromycin segment".) is also designed so as to have a desirable sequence, DNA is chemically synthesized according to the conventional method as the same as to conduct that of Poly A+cnvK segment. Such a chemical synthesis of the DNA chain may be entrusting to companies conducting these syntheses.

It is preferable for such a side chain to be designed so as to comprise the side chain binding site, the fluorescence label, and the peptide binding site as shown in FIG. 7. In the side chain, the nucleotide sequence (SEQ. ID NO. 2) without the modified site is as follows. In the following side chain, P (K in the following sequence), the free terminal, is puromycin as the peptide binding site. Also, in the following nucleotide sequence, R represents 5' Thiol C6, Y represents FITC-dT, and M represents Spacer 18, respectively.

[SEQ. ID NO. 2]
5' RTCTYMMCCK

For example, EMCS (Dojindo Laboratories) is added into 0.1 to 0.3 M sodium phosphate buffer (pH 7.0 to 7.4), which contains 10 to 20 nmol (final conc. 100 to 200 µM) of the backbone having the above-mentioned sequence, so as to be 15 to 18 mM at final concentration. The buffer is incubated and then it is subjected to ethanol precipitation. Preferably, EMCS (Dojindo Laboratories) is added at about 16.7 mM into 0.1 to 0.3 M sodium phosphate buffer (pH about 7.2), which contains 15 nmol (final conc. 150 µM) of the backbone having the above-mentioned sequence. The buffer is incubated at about 37° C. for about 30 minutes, and then it is subjected to ethanol precipitation by using, for example, Quick-Precip Plus Solution (Edge BioSystems) and the like for modification.

Next, 30 to 45 nmol of the side chain is dissolved in 0.8 to 1.5 M sodium hydrogen phosphate buffer containing 40 to 60 mM DTT at final concentration between 400 to 430 µM and stirred about 0.75 to 1.5 hour by using a shaker. Subsequently, buffer exchange is conducted for the solution. Preferably, about 7.5 nmol of the side chain is dissolved so as to be about 417 µM at final concentration in about 1 M sodium hydrogen phosphate buffer containing about 50 mM DTT. The buffer is stirred at ambient for about 1 hour by using the shaker. Subsequently, the buffer exchange is conducted for the solution. For example, the buffer is exchanged to about 0.1 M sodium phosphate (pH about 7.0) containing about 0.15 M NaCl by using NAP5 column to obtain reduced side chain.

Figure 8:
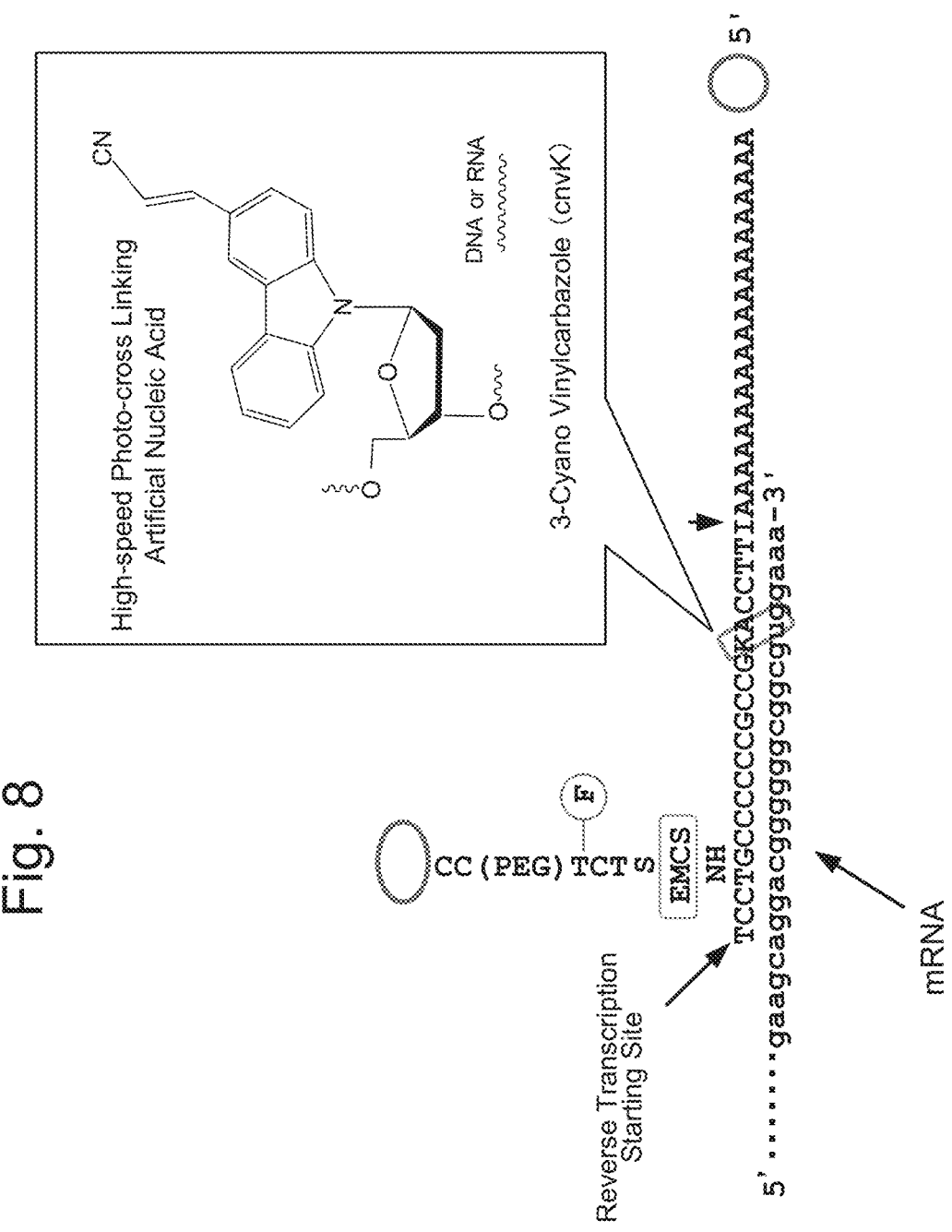
FIG. 8 is the schematic figure showing the photo-crosslinking type linker and mRNA bound thereto by using photo-crosslinking (SEQ ID NOS: 15 and 39, respectively, in order of appearance)
Figure 9:
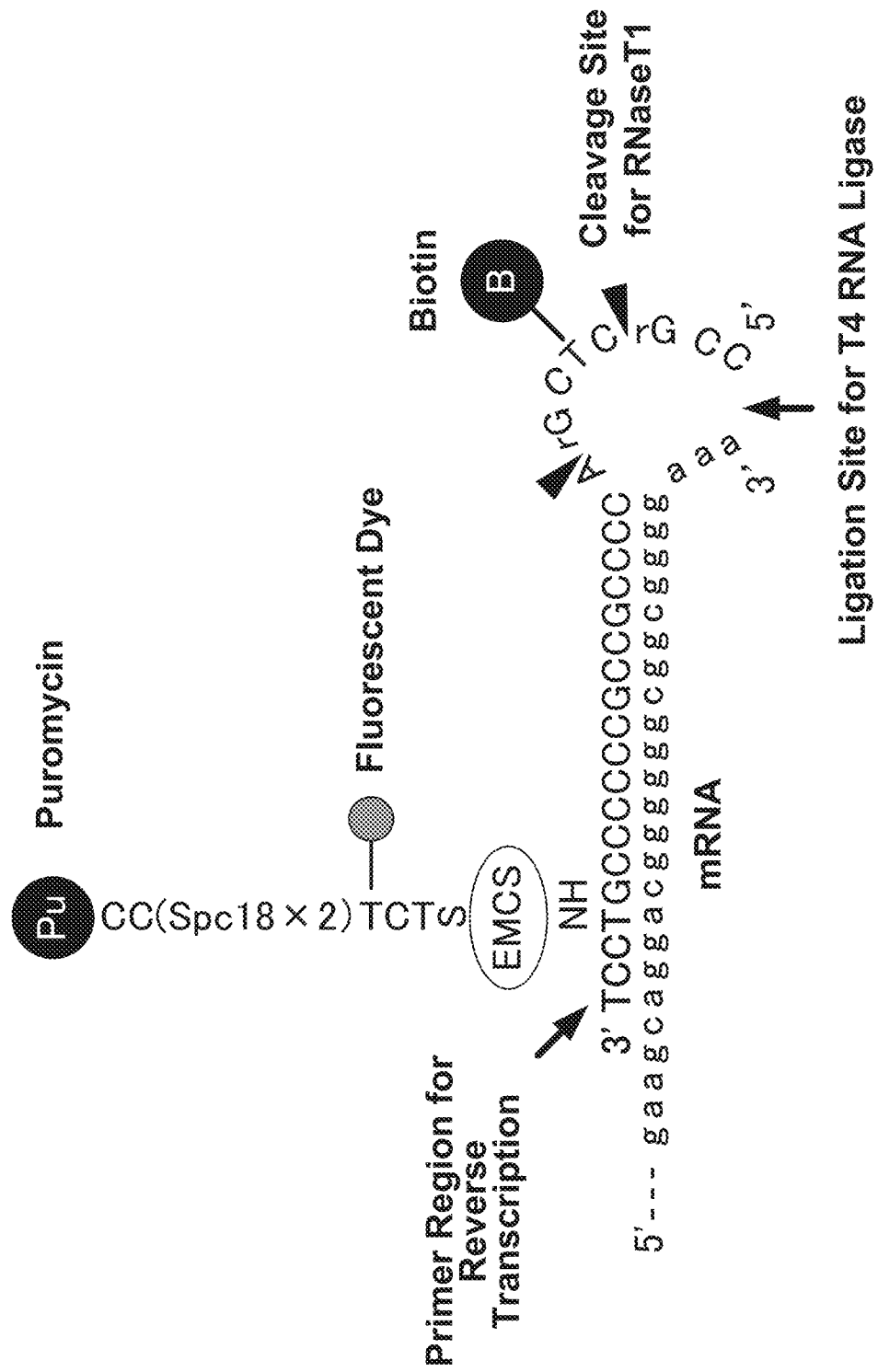
FIG. 9 is the schematic figure showing a conventional type linker and mRNA enzymatically bound thereto by using T4 RNA ligase (SEQ ID NOS: 14 and 40, respectively, in order of appearance).

Next, the solution containing the reduced side chain of which buffer is exchanged as described above was mixed with the ethanol precipitate of the backbone modified with EMCS, left to stand at 2 to 6° C. for overnight. After that, DTT was added into the reaction mixture so as to be 40 to 60 mM, and stirred at ambient for 15 to 60 minutes. After that, the mixture is subjected to ethanol precipitation, which is dissolved in 50 to 200 µL of nuclease free water for the purification thereof. Preferably, the solution containing the reduced buffer of which buffer is exchanged is mixed with the ethanol precipitates of the backbone modified with EMCS and leave to stand at about 4° C. for overnight. Then, DTT is added to the reaction mixture so as to be about 50 mM in final concentration and stirred at ambient for about 30 minutes. After that, ethanol precipitation is conducted by using, for example, Quick-Precip Plus Solution (Edge BioSystems). Obtained ethanol precipitation product is dissolved in about 100 µL of the nuclease free water and subjected to HPLC purification under the following conditions by using, for example, C18 column with gradient elution to obtain the photo-crosslinking type linker (FIG. 8).

Elution buffer for the gradient elution may contains, for example, 0.05 to 0.2 M of trimethyl ammonium acetate (in Ultra pure water) as A solution, and 75 to 85% acetonitrile as B solution; the ratio of A solution in the elution buffer at the start may be decreased about 20% within 40 to 50 minutes. Flow rate may be 0.5 to 1.5 ml/min, and the fraction volume may be 0.5 to 1.5 mL. Preferably, A solution is about 0.1 M trimethyl ammonium acetate (in Ultra pure water), B solution is about 80% acetonitrile; the ratio of A solution (about 85%) in the elution buffer at the starting point is decreased to about 65% in 40 to 50 minutes. The flow rate is about 1.0 ml/minute, the fraction volume is about 1.0 mL.

The components in the fraction are confirmed with both of fluorescence and UV absorption (about 280 nm). The fractions showing the peaks by both detection means are collected, and then the solvent in the collected fractions are evaporated by using vacuum evaporator. Then, it is subjected to ethanol precipitation, and the precipitate is dissolved in the nuclease free water to manufacture the linker of the present invention. For example, when the fractions from 30 to 32 minutes show the peaks in both of fluorescence and UV, those fractions are collected, and the solvent is evaporated by using the vacuum evaporator. Then, ethanol precipitation is conducted by using, for example, Quick-Precip Plus Solution, to obtain the photo-crosslinking linker. The obtained photo-crosslinking linker may be dissolved in the nuclease free water to store at about −20° C.

Note that the conventional enzyme type linker may be used in the present invention. Firstly, DNA is synthesized so as to have the desired sequence according to the conventional method to manufacture a single strand oligomer used as the backbone. As described above, the synthesized single strand oligomer comprises the solid phase binding site, at least two cleavage sites, mRNA binding site, side chain binding site, and primer region. Depending on the length and the location in the backbone of the at least 2 cleavage sites, the length of the single strand oligomer to be the backbone is properly determined. Next, the side chain having the desirable length is synthesized to be bound at the side chain binding site in the backbone. At the free terminal of the side chain, for example, puromycin is introduced, Fluorescein-dT as described above is introduced to the fluorescence label site. By these, the linker for manufacturing the mRNA/cDNA-peptide conjugate of the present invention may be obtained.

When the backbone is designed, a variety of the mRNA coding sequence may be referred. For example, there are mentioned mRNA such as those coding receptor proteins of which sequences are known, those coding antibodies or fragments thereof and the like. 3' terminal analogue of aminoacyl tRNA such as puromycin or its derivatives are incorporated at the C terminal of the poly peptide chain generated by translation from mRNA coding sequence. In order to bind the poly peptide chain and the linker-mRNA conjugate, the sequence without stop codon is chosen. Such mRNA may be obtained by using in vitro transcription, chemical synthesis, and other method such as extraction from living body, cells, microorganisms and the like. However, it gives high efficiency of the binding to the linker and cell free system translation, when it is manufactured by using in vitro transcription.

It is preferable to comprise at least one of 7-methylated guanosine cap structure at 5' terminal, or poly A tail structure at 3' terminal, because of the protein synthesis efficiency. It is more preferable to comprise Kozak sequence, or Shine-Dalgarno sequence, because it promotes the start of translation. In principal, the length of mRNA used here depends on that of coding region, which is defined on the basis of the length of the protein or poly peptide for their molecular evolution by utilizing the present invention. It is preferable for the length from 50 to 1,000 nucleotides, because of the reaction efficiency, and it is more preferable for the length from 200 to 500 nucleotides, because the highest reaction efficiency is achieved.

(3-2) Ligation of mRNA and the Linker

The photo-crosslinking of the obtained mRNA and the linker of the present invention is conducted by irradiating UV with long wave length, 300 to 400 nm, for 0.5 to 5 minutes. It has the advantages for obtaining the desirable peptide having the corresponding sequence to that of the used mRNA without the problem that the thymine dimer is generated in the synthesized cDNA, because the employed UV has long wave length and short irradiation time.

(3-3) Preparation of mRNA/cDNA-Protein Conjugate Through Cell Free Translation of the mRNA-Linker-Conjugate It is preferable for the cell free translation of the mRNA-linker-conjugate to utilize mammalian reticulocyte lysate, and more preferable to utilize that from rabbit blood. In order to induce the anemia, acetyl phenyl hydrazine is administrated in advance to the mammal, and their blood is collected several days later from the administration. By this, the ratio of the reticulocyte in the blood is increased. For example, the lysate treated with the micrococcal nuclease to degrade cell-derived mRNA and inactivated by addition of glycol ether diamine tetra acetic acid (EGTA) to chelate calcium (hereinbelow, it is sometimes referred to as "micrococcal nuclease treated".) is used.

For example, the rabbit reticulocyte lysate treated with micrococcal nuclease and the conjugate are added into 10 to 100 µL of the reaction mixture containing about 16 to about 400 mM potassium acetate, about 0.1 to about 2.5 mM magnesium acetate, about 0.2 to about 50 mM creatine phosphate, 0 to about 0.25 mM amino acids (these are final concentrations) to conduct the translation.

From the view point of the reaction efficiency, the volume of the rabbit reticulocyte is about 8.5 to about 17 µL, that of the conjugate is about 1.2 to about 2 pmol, and the size of the reaction system is about 12.5 to about 25 µL. Then, the translation is conducted at the range from about 20 to about 40° C., for about 10 to about 30 minutes. The reaction mixture used here contains about 80 mM potassium acetate, about 0.5 mM magnesium acetate, about 10 mM creatine phosphate, each about 0.025 mM methionine and leucine, about 0.05 mM amino acids other than methionine and leucine. When the translation is conducted about 30° C. for about 20 minutes, both of the efficiencies of the generation efficiency and the working efficiencies are high.

After the translation step, a peptide which is a translation product and a linker-mRNA conjugate are reacted, for example, in the presence of about 0.3 to about 1.6 M sodium chloride and about 40 to about 170 mM sodium magnesium (either is final concentration), at about 27 to about 47° C. for about 30 minutes to about 1.5 hour, so that the peptide and the conjugate can efficiently bind.

(4) Preparation of the Spherical Shaped Structure (4-1) Preparation of the Spherical Shaped Molecule In this embodiment liposome is used as the spherical shaped molecule. Huge liposomes which are confirmed by using an optical microscope and usable in the cell sorter are prepared by using W/O emulsion method. Firstly, 5 to 15 mM phospholipid in chloroform is prepared. The solution is poured into a glass test tube, and chloroform is removed by blowing nitrogen gas to the solution to from thin film made of the phospholipid on the inner surface of the test tube. Here, it is used as the phospholipid such as dioleoyl phosphatidylcholine (DOPC), dioleoyl phosphatidyl glycerol (DOPG), dipalmitoyl phosphatidylcholine (DPPC), egg phosphatidylcholine (egg PC) and the like.

Next, 200 to 400 µL of liquid paraffin is added into the test tube and sonicated at 55° C. to 65° C. for more than 1 hour. By this, the phospholipid is dissolved in liquid paraffin. After the sonication, desirable amount of inner membrane solution for the liposome is added into the solution and vigorously mixed more than 30 seconds by using sonication. As the inner solution of the liposome, 0.1 to 0.4 M glucose solution containing 25 to 75 mM NaCl and 27 to 75 mM tris buffer (pH 7.5) may be used.

The liposome may be labeled by adding the fluorescent label to be used for the flow cytometry in the liposome intermembrane solution. As the fluorescent labels, there are mentioned such as AMCA, Pacific Blur, Alex Flour 405, Pacific Orange, Krome Orange, Brilliant Violet 421, Brilliant Violet 510, Brilliant Violet 605, Brilliant Violet 650, Brilliant Violet 711, Brilliant Violet 785, Alex Flour 488, Quantum Dot, FITC, PE/RD1, ECD, PE-Texas Red, PC5, SPRD, PE-Cy5, PC5.5, PE-Cy5.5, PerCP, PerCP-5.5, PE-Alex Fluor 700, PE-Alex Fluor 750, PC7, PE-Cy7, TRITC, Cy3, Alex Fluor 594, Texas Red, Alex Flour 594, Alex Flour 700, Cy5, Cy5.5, APC, APC7, APC-Cy7, APC Alexa Fluor 700, APC Alexa Fluor 750, Hoechst 33342, DAPI, Dye Cycle Violet, Chromomycin A3, PI, YOYO-1, CPO, Pyronin Y, 7-AAD, Ethidium homodimer-1, SYTO9, SYBR Green I, LDS751, DRAQ5, DRAQ 7, TO-PRO3, Indo-1 (AM), Fluo-3(AM), Fluo-4(AM), Fura Red (AM), BCECF (AM), SNARF-1(AM), Fluorescein, R110, EBFP, ECFP, Keima-Red, AmCyan, EGFP, ZsGreen, EYFP, mBanana, mOrange, DsRed, tdTomato, mCherry, mCherry2, E2-Crimson, Kusabira-Orange, JC-1, Rhodamine, mCIB, CMFDA, CFSE, DiOC2(3), DiBAC4(3), PKH26, DCFH-DA, DHR, FDA, Calein AM, Nile Red, Fluorescein Amine, and the like.

Also, it is preferable to label the liposome by using the plurality of the fluorescence labels having the different fluorescent wavelength chosen from the fluorescence labels, because it enables to choose the objective fluorescent liposome accurately. For example, either Fluorescein Amine generating green fluorescence and Alexa Fluora 594 generating red fluorescence, or FITC generating green fluorescence and mCherry2 generating red fluorescence are chosen for double labeling of the liposome, the fluorescence labeled liposome (hereinbelow, it is sometimes referred to as "fluorescent liposome".) is accurately chosen.

After that, for example, Tris buffer (pH 7.5) or 0.1 to 0.5 M glucose solution containing NaCl is used as the outer solution of the liposome membrane, the inner solution of the liposome membrane is left to stand on the outer solution; and the solution is centrifuged at ambient temperature. By this, since the droplet in the liposome membrane mixture coated by the phospholipid single layer, which is formed at the interface between the oil and the outer solution of the liposome, the liposome is formed. Then, the liquid paraffin is existing in the upper portion, the solution containing the liposome is obtained.

The membrane of the obtained liposome may be labeled with fluorescence label according to the conventional method. Alternatively, the liposome membrane may be labeled by using the commercially available kit, for example, Green-fluorescent Cytoplasmic Membrane Staining Kit (Takara Bio Inc.), which contains carbocyanine dye with green fluorescence. Besides, the liposome may be labeled with orange fluorescence by using Orange-fluorescent Cytoplasmic Membrane Staining Kit (Takara Bio Inc.), red fluorescence by using Red-fluorescent Cytoplasmic Membrane Staining Kit (Takara Bio Inc.), or blue fluorescence by using Blue-fluorescent Cytoplasmic Membrane Staining Kit (Takara Bio Inc.). By using such labels, the fluorescent labeled liposomes are distinguished.

Furthermore, by using the fusion protein composed of the protein bounds to the liposome membrane and the label molecule, the liposome membrane may be modified with the label molecule. For example, the following sequences are synthesized: that coding LB-1 peptide which functions as the anchor to the liposome membrane, that coding biomolecule such as fluorescent protein, mCherry2, GFP and the like as the label molecule, a variety of antibodies, proteins to be disease markers, and His-tag and the like. Subsequently, these sequences are induced into a multi-cloning site of a vector for expressing the fusion protein composed of such as LB-1 and the fluorescent protein in *E. coli* according to the conventional method. After that, the fusion protein may be obtained, for example, by His-tag purification The obtained fusion protein is added to the liposome solution at the predetermined concentration and sufficiently stirred. By this, LB-1 protein is bound to the liposome membrane, and the labeled molecules are expressed on the liposome membrane surface. If the target molecules are the fluorescent protein, images of the liposome membrane labeled with the fluorescent label are obtained by using the microscope.

(4-2) Binding of the mRNA-Protein Conjugate or the mRNA/cDNA-Protein Conjugate to the Liposome The mRNA-protein conjugate or the mRNA/cDNA-protein conjugate obtained as described is bound to the liposome through the binding of the target molecule on the liposome membrane and peptide binding to the peptide binding site of the linker, or direct binding of the peptide on the linker with the functional group on the liposome. For example, anti-bacterial peptides such as Magainin 2, PGLa, Melittin and the like are bound to the cell membrane of the bacteria. Since these peptides includes 15 to 40 amino acid residue and are amphiphilic cluster composed of basic amino acids with hydrophobic amino acids, most of them have the property that they form α-helix structure when they bind to the bacteria cell membrane surface. By using the property, DNA coding the liposome membrane binding protein is designed, and either the mRNA-protein conjugate or mRNA/cDNA-protein conjugate is bound to the liposome to obtain the liposome conjugate as the spherical shaped conjugate.

(5) Reverse Transcription

Reverse transcription may be conducted before the separation step using the cell sorter or after the separation step. cDNA chain is synthesized by using the mRNA as the template and 3' terminal of the backbone on the linker contained in the mRNA-protein conjugate as the starting point under the predetermined conditions according to the conventional method to obtain the mRNA/cDNA-protein conjugate. Reverse transcription system is optionally chosen and not limited. However, it is preferable to prepare the reaction system containing the linker-mRNA conjugate, dNTP mixture, DTT, reverse transcriptase, standard solution, and water from which RNase is removed (hereinbelow, it is sometimes referred to as "RNase free water".) and conduct reverse transcription in the system under the conditions such as or 5 to 20 minutes at the temperature range from 30 to 50° C. Reverse transcription may be conducted by using the commercially available kit, for example, PrimeScript RT-PCR Kit (Takara Bio Inc.) or ReverTra Ase (TOYOBO Co. Ltd.) according to the protocols attached to them.

(6) Sorting

By using the cell sorter for general use, the fluorescent liposome is solely sorted according to the manual. When the fluorescence dyes are used, compensation of fluorescence is appropriately conducted, and the objective liposome area is specified from the distribution of the fluorescent intensity. Concretely, it is reacted the control sample which has the similar function to the objective peptide, and then the fluorescent area is specified on a histogram, the fluorescent liposome is selectively fractionated from the same area with the objective sample.

For example, DNA coding antibacterial peptide-like peptides to be bound with the cell membrane such as Magainin 2, PGLa, Melittin and the like are designed. Previously, these antibacterial peptide and fluorescent labeled liposome are reacted to specify the fluorescence area by using the cell sorter. Then, referring to the properties of the antibacterial peptide, the DNA coding the peptide binding to the liposome is designed. According to the analysis diagram of the cell sorter, an area similar to the specified one is surrounded to fractionate the liposome conjugate to which the objective peptide is bound to be fractionated (hereinbelow, it is sometimes referred to as the "fluorescent liposome conjugate".).

The liposome conjugate solution after sorting is stirred by using vortex and the like to release the cDNA displayed molecule (the mRNA-protein conjugate, or the mRNA/cDNA-protein conjugate) from the liposome conjugate. Then, the solution is centrifuged to separate an organic phase containing lipid, and an aqueous phase containing the cDNA display molecule. The mRNA-protein conjugate or the mRNA/cDNA-protein conjugate may be purified by using either of ethanol precipitation or nucleic acid column purification from the cDNA display molecule dissolved in the aqueous phase.

(7) Preparation of PCR Sample

The mRNA-protein conjugate obtained through the above-mentioned purification may be immobilized on the desirable solid phase when reverse transcription is conducted. As the solid phase, for example, there are mentioned, for example, beads such as styrene beads, glass beads, agarose beads, Sepharose beads, and the like; substrate such as glass substrate, silicone (quartz) substrate, plastic substrate, metal substrate (for example, beaten gold substrate); wears such as glass were, plastic and the like; membrane made of the material such as nitrocellulose, poly vinylidene fluoride (PVDF) and the like.

When the solid phase is made of plastic materials such as styrene beads, styrene substrate and the like, the linker or a part thereof may be directly bound covalently by using the conventional method (Qiagen, see LiquiChip Applications Handbook and the like). When biotin or its derivative is bound to the mRNA/cDNA-protein conjugate, the conjugate is easily bound to the solid phase by binding avidin on the solid phase.

The beads were removed from mRNA/cDNA-protein conjugate obtained by immobilization to recover the linker-mRNA/cDNA conjugate. Firstly, the magnetic beads are washed with the desirable washing buffer, and subsequently, the releasing agent is incubated into it and incubated, to release the linker-mRNA/cDNA conjugate cleaved at the cleaving site. As such the washing buffers, for example, 1×

His-tag washing buffer (containing 10 to 30 mM sodium phosphate (pH 7.4), 0.25 to 0.75 M NaCl, 10 to 30 mM imidazole, 0.025 to 0.1% Tween-20), or 1×NEB 4 buffer may be used. Also, as the releasing agent, RNA degradation enzyme with the desirable concentration, for example, 1× His-tag washing buffer containing 500 to 1,500 U RNase T1, or 1× NE buffer containing 10 U Endonuclease V (New England Biolabs) and the like may be used.

The linker-mRNA/cDNA conjugate may be purified by using His-tag protein purification beads, His Mag Sepharose Ni (GE healthcare) and the like. His-tag protein purification beads are washed with His-tag washing buffer in advance. Next, the collected linker-mRNA/cDNA conjugates are added into the washed His-tag protein purification beads and incubated under the desirable conditions. Then, the beads are washed with His-tag washing buffer, and His-tag protein elution buffer is added and stirred under the desirable conditions to obtain purified linker-mRNA/cDNA conjugate.

The purified linker-mRNA/cDNA conjugate is amplified by using PCR method with the desirable primers, and DNA library comprising the desirable coding sequences may be prepared. For example, the purified linker-mRNA/cDNA conjugate contained in the solution is precipitated by using, for example, the co-precipitant (Quick-Precip Plus Solution, EdgeBio), and then PCR reaction mixture is added to conduct the desirable PCR program.

Also, the present invention is explained when streptavidin is used as the target molecule, and RNA aptamer is used as the target detection molecule as an example.

(1) Preparing DNA and RNA Aptamer

As RNA aptamer that binds to the target molecule, streptavidin, known streptavidin binding RNA aptamer (hereinbelow, it is sometimes referred to as "SAB-RNA aptamer".) may be used. For example, both DNAs of the SAB-RNA aptamer and RNA aptamer to which streptavidin is not bound (hereinbelow, it is sometimes referred to as "SAN-RNA aptamer".) are constructed as the sequence having T7 promoter sequence at the 5' terminal of both of the RNA aptamers so as to prepare the objective RNA after the transcription.

When the DNA of the SAB-RNA aptamer is prepared, the primers having the following sequences shown in the following Table 2 are respectively prepared and used. Among the 5' primer, T7 promoter sequence is the third to $22^{nd}$ DNAs.

Similar to this, when SAN-RNA aptamer DNA is prepared, the primer (shown as SEQ. ID NO. 12) having the following sequence is manufactured and used together with the primer having the sequence shown as SEQ. ID NO. 11. Among these 5' primers, Nos. $3^{rd}$ to $22^{nd}$ of the amino acid sequence shows T7 promoter sequence.

TABLE 2

| primer | Sequence | SEQ. ID NO. |
|---|---|---|
| 5' | AGTAATACGACTCACTATAGGGAGTCGACCGACCA GAATCATGCAAGTGCGTAAGATAGTCGCGGGCCGG GGGCGTATTATGTGCGTCTACATCTAGACTCAT | 10 |
| 3' | ATGAGTCTAGATGTAGACGCACATA | 11 |
| 5' | AGTAATACGACTCACTATAGGGAGTCGACCGACCA GAAATGGATAACAAATTCAACAAAGAACAACAAT ATGTGCGTCTACATCTAGACTCAT | 12 |

DNA synthesis reaction mixture containing a polymerase, for example, Taq DNA polymerase, and dNTP is prepared, and two primers described above are added into it so as to be the predetermined concentration; and then each DNA is synthesized by using overlap extension method. As the DNA synthesis reaction mixture, included in the commercially available kit such as PrimeSTAR (Takara Bio Inc.) may be used. Also, the conditions of overlap extension are as follows: 30 seconds to 90 seconds from at 95 to 98° C., 5 to 10 seconds from at 60 to 62° C., 20 to 40 seconds from at 71 to 73° C., and then cool to 10° C. After that, DNA purification is conducted according to the conventional method. The purification is conducted by using, for example, the commercially available kit such as FavorPrep PCR Clean-Up Mini Kit (Favogen) according to the attached instruction manual.

Next, the transcription reaction mixture containing RNA polymerase, such as T7 RNA polymerase and rNTP are prepared, and the purified DNAs are added into it at the predetermined amount, and then conduct transcription by incubating at 37° C. from 20 minutes to 1 hour. After that, it is subjected to purification, for example, cutting out or the kit such as Rneasy minElute Cleanup kit (QIAGEN) and the like according to the attached instruction manuals. Obtained SA bound RNA aptamer and SA unbound RNA aptamer are subjected to bind with the spherical shaped structure.

(2) Immobilization of the Target Molecule on the Spherical Shaped Structure

In order to bind the streptavidin as the target molecule onto the spherical structure, for example, the spherical structure modified with the functional groups such as carboxy group and the like may be chosen. As these spherical structures, it may be purchased and used for the commercially available one, for example, silica beads such as Sicastar (the registered trademark: Micromod), latex beads such as Micormer (the registered trademark: Micromod) and the like.

When the spherical structure modified with carboxyl group is chosen, the carboxyl group is activated with imide compound to from NHS ester, and then bound to streptavidin as the protein. For example, as the spherical structure, the silica beads modified with carboxyl group are used, firstly, about 10 to about 30 μL of the silica beads are added into the centrifuged tube and centrifuged with about 15,000 rpm (about 20,000×g) for 3 to 7 minutes at ambient; and then supernatant is removed. Subsequently, about 80 to about 120 μL of N, N-dimethyl form amide (hereinbelow, it is sometimes abbreviated as "DMF".) is added to the tube and stirred sufficiently; and then, it is centrifuged with about 15,000 rpm (about 20,000×g) for about 3 to 7 minutes to remove the supernatant (the washing step), The washing step is repeated several times, and then about 40 to about 60 μL of about 100 to about 300 mM NHS solution, and about 40 to about 60 μL of about 100 to about 300 mM 1-(3-dimethylaminopropyl)-3-ethyl carbodiimide hydrochloride (hereinbelow, it is sometimes referred to as "EDC".) are added into it, then it is stirred between the temperature of about 20 to about 30° C. for about 1 to about 3 hours. After stirring, it is centrifuged with about 15,000 rpm (about 20,000×g) for about 3 to 7 minutes to remove the supernatant. Here, the washing step is repeated several times. After washing, about 80 to about 120 μL of about 5 to about 15 μM streptavidin is added into it and stirred overnight at ambient.

After stirring, it is centrifuged with about 15,000 rpm (about 20,000×g) for about 3 to about 7 minutes to remove the supernatant. Next, about 80 to about 120 μL of Ultra pure water is added into it and stirred sufficiently, and then the super natant is removed. The washing step is repeated several times. Lastly, about 10 to about 30 μL of HEPES-Na buffer (pH from about 7.2 to about 7.6) is added into it to disperse the streptavidin-immobilized silica beads (positive spherical structure) to obtain the positive spherical structure containing solution.

For the preparation of the spherical structure, the spherical structure having red, blue or green labels thereon other than that having the functional group thereon may be used, because they may improve sorting efficiency. As the spherical structure having such labels, commercially available ones may be used. Here, the label contains such as fluorescent proteins, fluorescent dyes and the like.

(3) Forming of the Spherical Shape Conjugate and Sorting Thereof

The positive spherical structure (the spherical shaped structure P) with immobilized target molecule (streptavidin), the negative spherical structure (the spherical shaped structure N) without immobilized target molecule, SAB-RNA aptamer and SAN-RNA aptamer are added to the spherical structure as described above in HEPES-Na buffer (pH from about 7.2 to 7.4) containing 30% glycerol so as to be the predetermined concentration. Then the mixture is reacted at ambient from about 30 minutes to about 1.5 hour to obtain the positive spherical shaped conjugate (the spherical shaped conjugate P), wherein SAB-RNA aptamer is mainly bound to the spherical shaped structure P, the negative spherical shaped conjugate (the spherical shaped conjugate N), wherein SAN-RNA aptamer is mainly bound to the negative spherical structure, are obtained.

The predetermined concentration of HEPES-Na buffer (pH from about 7.2 to 7.4) is added to both of the spherical shaped conjugate P and the spherical shaped conjugate N, and then they are subjected to sorting by using FACS. When the sorting, it is set so as to match the labels on the employed spherical structure and sizes and conducted to the instruction manual attached to the employed machine.

EXAMPLE

Hereinbelow, the present invention is explained in detail, illustrating examples. Note that the following Examples show just referenced, and which does not limit the scope of the present invention.

(Example 1) Preparation of the Labeled Spherical Structure

As described above, since the liposome may be used to coat the surface of the beads, it is used as the spherical shaped molecule.

(1) Preparation of Reagents
(1-1) Chloroform Solution Containing Phospholipid

As the phospholipid which forms liposome, both dioleoyl phosphatidyl choline and dioleoyl phosphatidyl glycerol (both from Avanti) were dissolved in chloroform (Wako Pure Chemical industries) so as to their final concentration becomes 10 mM to prepare chloroform solutions containing the phospholipid as shown in the following Table 3.

TABLE 3

| Composition of phospholipid containing | Content amount (μL) | |
| --- | --- | --- |
| chloroform | Solution 1 | Solution 2 |
| dioleoyl phosphatidyl choline | 300 | 100 |
| dioleoyl phosphatidyl glycerol | — | 500 |
| chloroform | 600 | — |
| Total | 900 | 600 |

(1-2) Preparation of the Inner Membrane Solution and Outer Membrane Solution of the Fluorescent Liposome In order to prepare the liposome with the fluorescent label (hereinbelow, it is sometimes referred to as the "fluorescent liposome".), the inner membrane solution of the liposome containing the fluorescence substance with the composition shown in the following Table 4, and the outer membrane solution of the liposome with the composition shown in the following Table 5, respectively. Sucrose, glucose, NaCl, Tris-HCl shown in the table were purchased from Wako Pure Chemical Industries, fluorescein amine is purchased from Sigma-Aldrich, and transferrin Alexa Fluor 594 (hereinbelow, it is sometimes simply referred to as "Alexa".) was purchased from Life Technologies.

TABLE 4

| Composition | Content amount |
| --- | --- |
| Sucrose | 0.2 M |
| NaCl | 50 mM |
| Tris-HCl (pH 7.5) | 50 mM |
| Fluorescein amine | 100 μM |
| Transferrin-Alexa Fluor 594 | 2.5 μM |

TABLE 5

| Composition | Content amount |
| --- | --- |
| Glucose (Wako Pure Chemical Industries) | 0.2 M |
| NaCl (Wako Pure Chemical Industries) | 50 mM |
| Tris-HCl (pH 7.5)(Wako Pure Chemical Industries) | 50 mM |

(2) Preparation of the Liposome

The liposome was prepared by using water/oil Emulsion as follows. Firstly, L of the phospholipid containing chloroform solution prepared above (1) was placed in Durham test tube with the full length 30 mm (Maruemu Corp.); nitrogen gas was blown to the chloroform solution to evaporate chloroform to from thin film of the phospholipid on the inner surface of the Durham test tube. The Durham test tube with the phospholipid thin film was left to stand in a desiccator with a vacuum pump to remove remained chloroform more than 1 hour. The Durham test tube was taken out from the desiccator, and then 150 mL of liquid paraffin (Wako Pure Chemical Industries) was added into the tube, and placed in a sonicator at 60° C. more than 1 hour to dissolve the phospholipid in liquid paraffin to prepare the phospholipid containing paraffin solution.

After that, 20 μL of the inner solution of the liposome membrane containing Alexa, the fluorescent label, was added into the phospholipid containing paraffin solution, and then vigorously mixed by using the sonicator more than 30 seconds. After that, 200 μL of the outer solution of the liposome membrane was gently added into the solution, and the mixture was left to stand more than 30 minutes at ambient. Then, it was centrifuged by using the micro centrifuge for multi-purposes, SWING MAN (Hi-tech Inc.) at ambient with 4,200×g for 10 minutes. After the centrifugation, liquid paraffin located top of the solution was removed by using the pipetman to collect the liposome containing solution encapsulating the fluorescent label.

(3) Purification of the Liposome Encapsulating the Fluorescent Label

The liposome solution encapsulating the fluorescent label collected as described above (hereinbelow, it is sometimes referred to as the "fluorescent liposome".) was centrifuged at ambient with 1,000×g for 10 minutes to remove suspended materials such as aggregated phospholipids not formed liposome and the like to purify the fluorescent liposome.

(4) Observation by Using a Confocal Laser Microscope

The fluorescent liposome prepared as described above was observed by using the microscope as follows. Firstly, a silicon sheet having 200 µm thickness (AS ONE Corporation) was cut into 20×20 mm size pieces (a size of a cover glass), and then an opening of which diameter 5 mm was formed in the center of the pieces by using the commercially available paper punch. The silicon piece having the opening was placed on the cover glass, and then about 5 µL of the fluorescent liposome containing solution was dropped into the hollow form by the opening, and it was covered with other cover glasses to prepare the sample for the observation. The sample was put on the stage of the confocal laser microscope FV-1000D (Olympus Corporation) to observe the purified fluorescent liposome solution (hereinbelow, it is sometimes referred to as the "fluorescent liposome suspension".).

Figure 3:
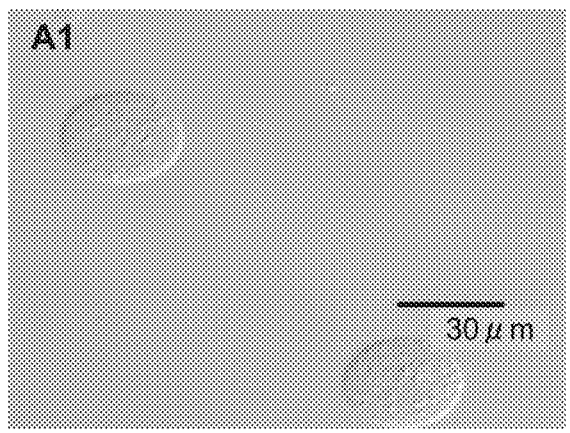
FIG. 3 is a photomicrograph showing the liposome including the fluorescent substance. A1 is a differential interference microscope image, B is a fluorescent image using FITC, and C1 is that using Alexa-Flour 594, respectively. A2 to C2 is the schematic figures of A1 to C1, respectively.
Figure 3:
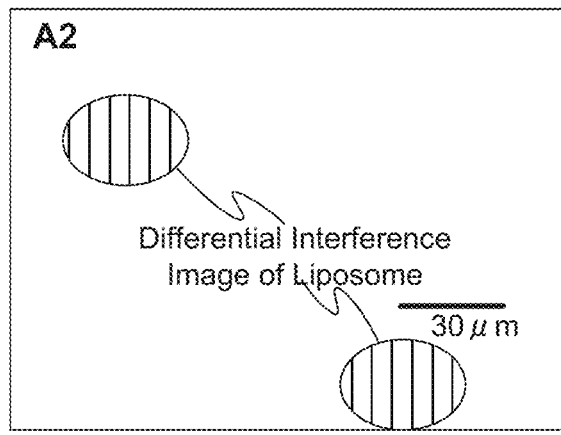
Figure 3:
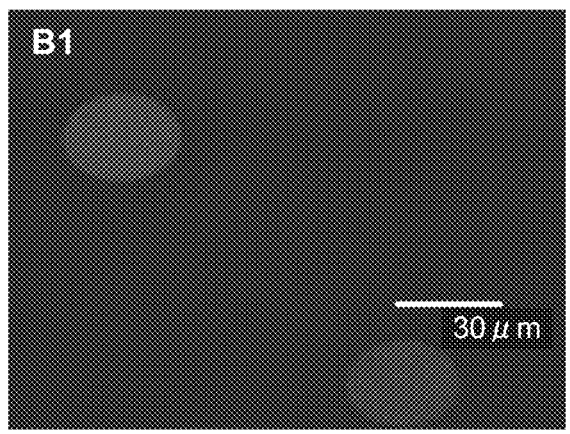
Figure 3:
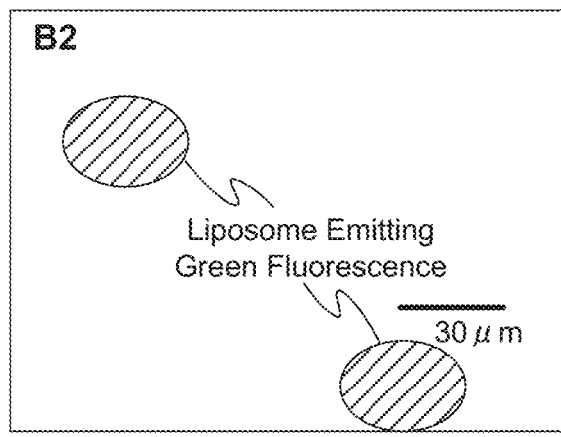
Figure 3:
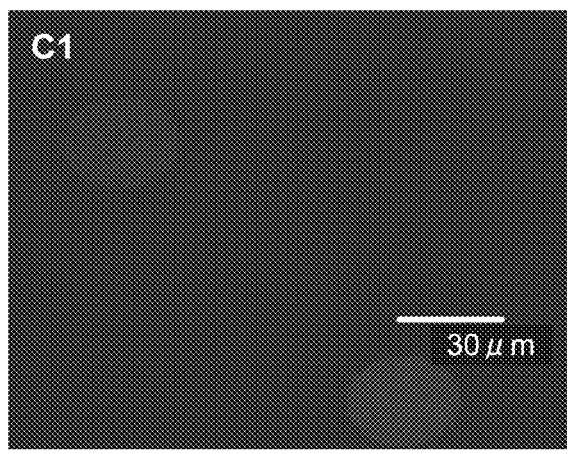
Figure 3:
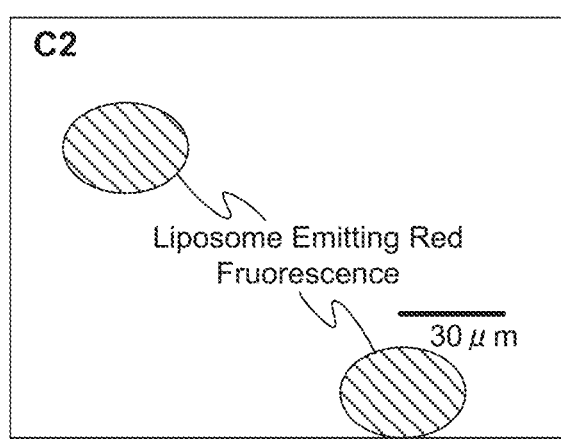

As a result, it was demonstrated that encapsulation of fluorescein amine or transferrin-Alexa Fluor 594 did not affect to liposome formation (FIG. 3A), and the particle size of the formed liposomes were between several m to several tens m. Also, it was confirmed that both of the fluorescent dyes have sufficient fluorescent intensity for the observation by using the confocal microscope (FIGS. 3B and 3C).

(5) Specification of the Fluorescent Liposome Areas by Using FACS

As the cell sorter, FACS was employed. Prior to fractionate the fluorescent liposome suspension by using FACS, the stability of the liposome, which affects the reproducibility of the experiment, was confirmed. In order to confirm it, Magainin 2(Sigma-Aldrich), which has the properties to bind to the phospholipid membrane to destroy it, was used.

Depending on the added amount of Magainin 2, the histogram by FACS was changed. From the results, the liposome to be fractionated was specified. Firstly, the fluorescent liposome suspension was solely analyzed with FACS. Subsequently, both of 400 µL of the fluorescent liposome suspension, and 400 µM Magainin 2 (final conc. 10 µM or 30 µM) were added to the suspension, and reacted at ambient for 1 hour. After that, the suspension was filtrated by using the filter having 40 µm of the pore size, and the fluorescent intensity of the filtrate was analyzed by using FACS (Cell Sorter SH800: SONY Business Solution).

Figure 4A:
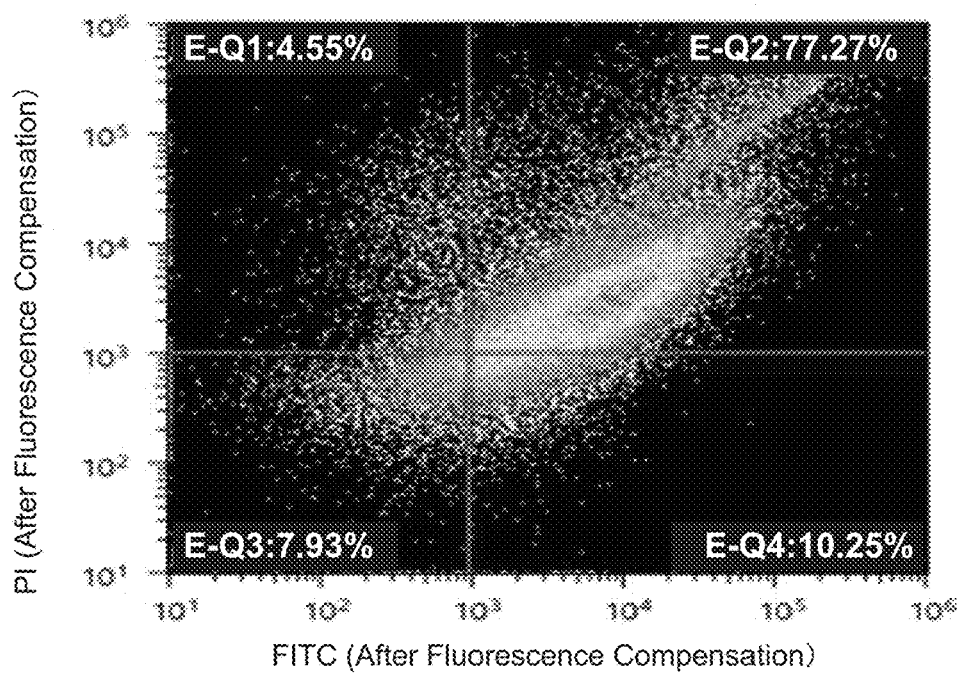
FIG. 4A is the drawing showing the FACS analysis result of the fluorescent liposome without treatment by Magainin 2.
Figure 4B:
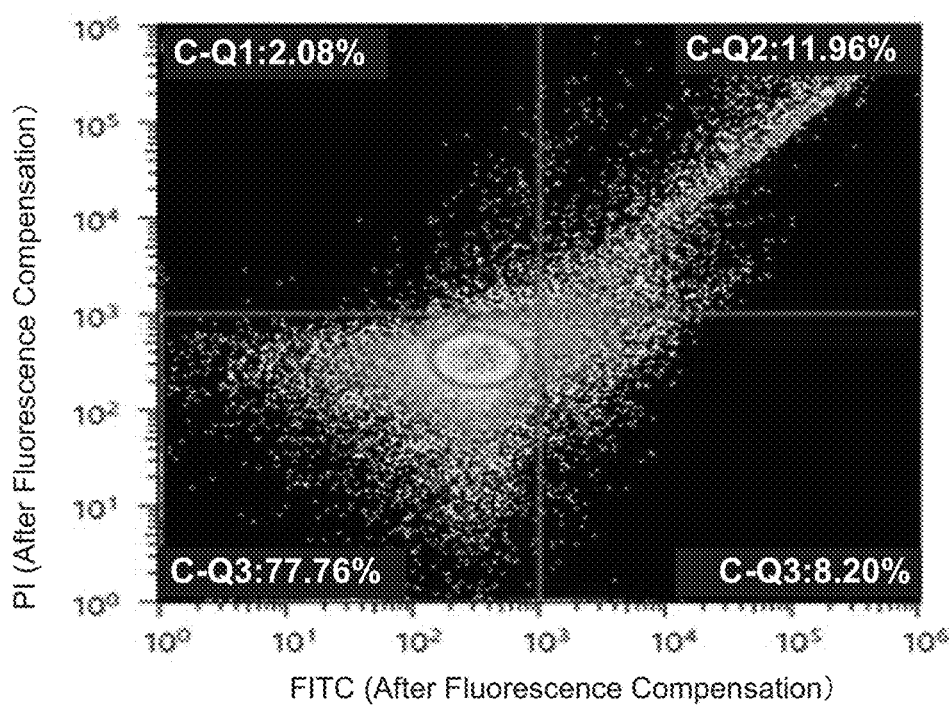
FIG. 4B is the drawing showing the FACS analysis result of the fluorescent liposome with treatment by 10 µM of Magainin 2.
Figure 4C:
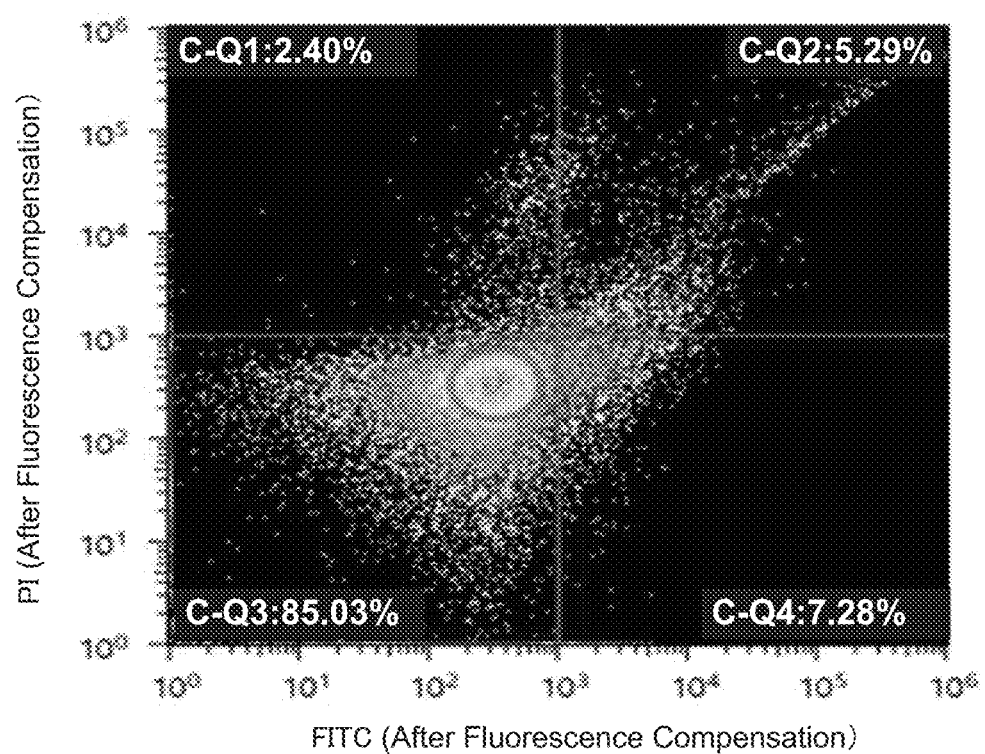
FIG. 4C is the drawing showing the FACS analysis result of the fluorescent liposome with treatment by 30 µM of Magainin 2.

As a result, it was confirmed that the sample without Magainin 2 had two areas, in one of the area, both of 2 fluorescent intensities were high (hereinbelow, it is sometimes referred to as the "high areas".), and both were low (hereinbelow, it is sometimes referred to as the "low area".) (FIG. 4A). On the other hand, in the sample with 10 µM Magainin 2, the low area was disappeared (FIG. 4B); in the sample with 30 µM Magainin, both of high area and low area were disappeared (FIG. 4C). By these, it was confirmed that the fluorescent liposomes were existed in both of the high and low areas. Also, the lower area was broader compared to the high area, the liposome was fractionated from the high area for the careening for the screening of the present invention, considering the reproducibility of the fluorescent.

Figure 5:
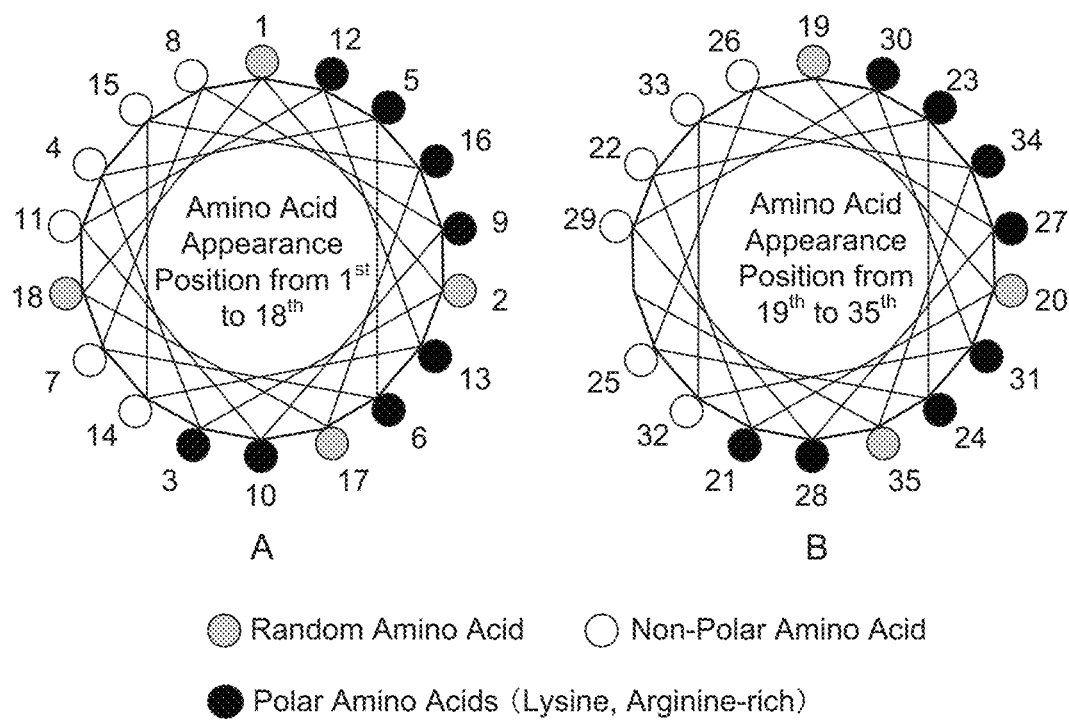
FIG. 5 is the drawing showing the peptide predictable sequence to be translated by a designed DNA library and the sequence as two α-helix wheels, A and B. Wherein, A shows amino acids at the expressing position Nos. 1 to 18 and B shows these at the expression Nos. 19 to 35.

(Example 2) Preparation of the Fluorescent Liposome (1) Preparation of the DNA Library The peptide reacted with the phospholipid membrane should have the sequence which was lysine and arginine rich, and easily forms amphiphilic α-helix structure in the phospholipid membrane. Therefore, DNA library was designed 5'-3' lines shown on A and B in FIG. 5 by using α-helical wheel diagram, so as to arrange the appearance positions of polar amino acids containing lysine and arginine on right half of the wheel diagram (A), and non-polar amino acids on left half of it (B).

The DNA library was prepared as follows. Firstly, a sequence having the full length of 244 mer was prepared as 3 fragments, random region (SEQ. ID NO. 3), R-Ytag region (SEQ. ID NO. 4) and T7-PRO-SD region (SEQ. ID NO. 5) as that each fragment included overlap region respectively. Then, these fragments were extended by using extension PCR to obtain the full-length sequence. The synthesis of all of the random region, R-Ytag region and T7-PRO-SD region were ordered to Tsukuba Oligo Service Co., Ltd. By using these, extension PCR was conducted according to the procedure shown in the schematic figure on FIG. 6 to prepare three DNA fragments having the following sequence described above.

[SEQ. ID NO. 3]
5' ATTCCACCATGGGCGGTBDHBDHKSWRYMKSWKSWRYMRYMKSWKSW

RYMKSWKSWRYMRYMKSWBDHBDHBDHKSWRYMKSWKSWRYMRYMKS

WKSWRYMKSWKSWRYMRYMKSWBDBGGGGGAGGCAGCCA 3'

In the sequence described above, the frequency of the nucleotides other than ATCG instead of ATGC (A: T: G: C) was as shown in following Table 6.

TABLE 6

| | Expression frequency of nucleotides other than ATGC | | | |
|---|---|---|---|---|
| Expressed position | A | T | G | C |
| R | 0.2 | 0.15 | 0.35 | 0.3 |
| Y | 0.1 | 0.4 | 0.15 | 0.35 |
| M | 0.15 | 0.3 | 0.25 | 0.3 |
| K | 0.55 | 0 | 0.25 | 0.2 |
| S | 0.6 | 0.1 | 0.2 | 0.1 |
| W | 0.4 | 0.1 | 0.4 | 0.1 |
| B | 0.33 | 0.07 | 0.35 | 0.25 |
| D | 0.38 | 0.25 | 0.2 | 0.17 |
| H | 0.1 | 0.3 | 0.3 | 0.3 |

[SEQ. ID NO. 4]
5' TTTCCCCGCCGCCCCCGTCCTATGGCTGCCTCCCCC 3'

[SEQ. ID NO. 5]
5' GATCCCGCGAAATTAATACGACTCACTATAGGGAGACCACAACGGTT

TCCCTCTAGAAATAATTTTGTTTAACTTTAAGAAGGAGATTCCACCATGG

GCGG 3'

Figure 1B:
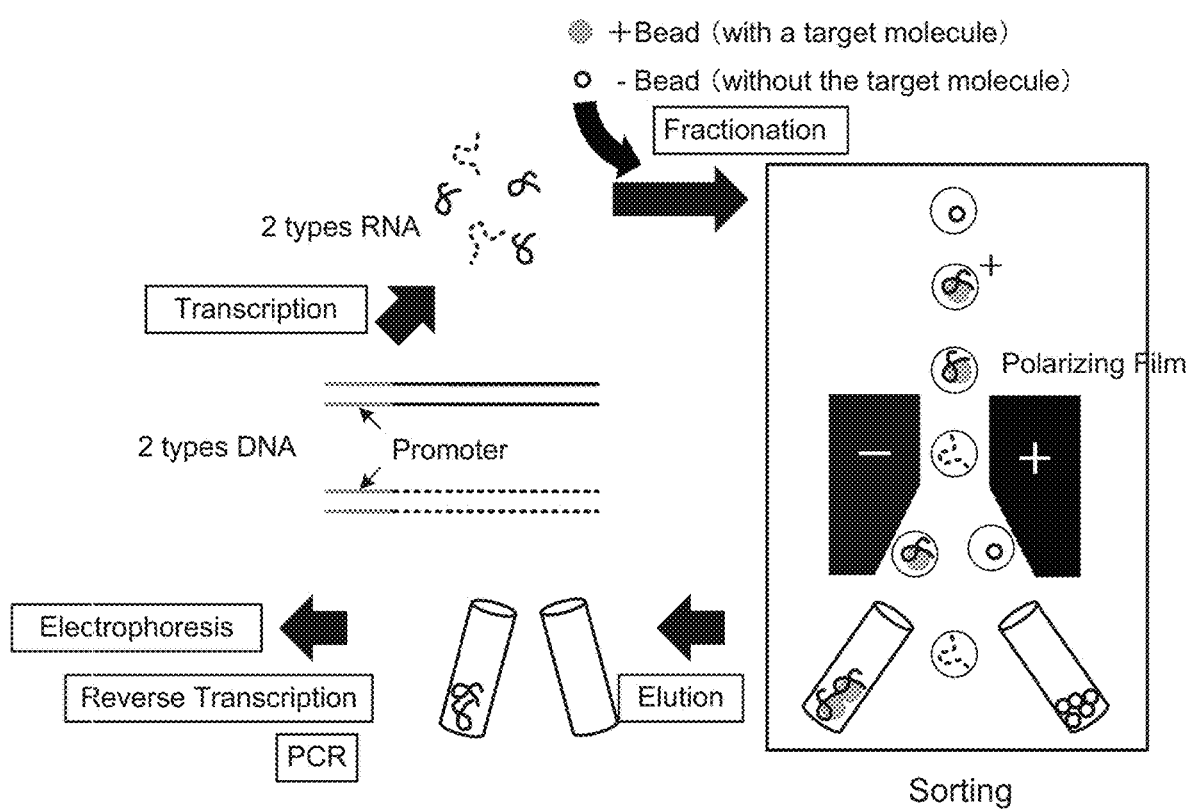
FIG. 1B is the drawing showing the screening procedure, when RNA is used as the target detection molecule.

Extension PCR 1 show in FIG. 1 was conducted by using PrimeSTAR (Registered trademark) HS DNA Polymerase (Takara Bio Inc.). The reaction mixture having the composition shown in the following Table 7 was adjusted to 25 µL with Ultra pure water, its random region was amplified under the following PCR program: (a) at 96° C. (2 minutes), (b) at 94° C. (20 second), (c) at 51° C. (5 second), (d) at 72° C. (30 second), and (e) at 72° C. (2 minutes), and steps (b) to (d) were conducted 5 cycles.

TABLE 7

| Composition of extension PCR2 reaction mixture | Content amount (µL) |
|---|---|
| Random region (10 pmol/µL) | 1 |
| R-Ytag region (100 pmol/µL) | 1 |
| 5 × PrimeSTAR buffer (Takara Bio Inc.) | 5 |
| dNTP mix (25 mM each) (Takara Bio Inc.) | 4 |
| Takara PrimeSTAR buffer (Takara Bio Inc.) | 0.25 |
| Ultra pure water | Remains |
| Total | 25 |

In Extension PCR 2 shown in FIG. 6, the reaction mixture shown in the following Table 8 was adjusted to 25 µL with Ultra pure water, T7-PRO-SD region was amplified under the following PCR program: (a) at 96° C. (2 minutes), (b) at 94° C. (20 second), (c) at 58° C. (5 second), (d) at 72° C. (30 second) and (e) at 72° C. (2 minutes), and the steps (b) to (d) were conducted 5 cycles.

TABLE 8

| Composition of extension PCR2 reaction mixture | Content amount (µL) |
|---|---|
| Extension PCR1 product (10 pmol/µL) | 1 |
| T7-PRO-SD region (10 pmol/µL) | 1 |
| 5 × PrimeSTAR buffer (Takara Bio Inc.) | 5 |
| dNTP mix (25 mM each) (Takara Bio Inc.) | 4 |
| TaKaRa PrimeSTAR buffer (Takara Bio Inc.) | 0.25 |
| Ultra pure water | Remains |
| Total | 25 |

(2) Preparation of the Target Binding Molecule (Ligation of mRNA and the Linker)

(2-1) Preparation of mRNA

Firstly, transcription from the DNA library obtained as described above to mRNA was conducted as follows.

The reaction mixture shown in the following Table 9 was adjusted to 20 µL with Ultra pure water, and reacted at 37° C. for 4 hours. After that, 1 µL of RQ-1 RNase-Free DNase (Promega) was added into the reaction mixture, and then further reacted at 37° C. for 20 minutes. After completion of the reaction, purification was immediately conducted by using Rneasy minElute Cleanup kit (QIAGEN), according to the attached instruction manual.

TABLE 9

| Composition | Content amount |
|---|---|
| T7 transcription 5 × buffer (Promega) | 4 µL |
| rNTPs (25 mM ATP, CTP, UTP, GTP) (Promega) | 4 µL |
| Enzyme mix (Promega) | 2 µL |
| Template DNA | 100 to 500 ng |
| Ultra pure water | remains |
| Total | 20 |

(2-2) Binding of mRNA and the Conventional Linker

Next, the obtained mRNA and the puromycin-linker described below were ligated as follows. Firstly, the reaction mixture shown in the following Table 10 was adjusted to 20 µL with Ultra pure water. The reaction mixture was incubated at 90° C. for 2 minutes and then at 70° C. for 1 minute, and then it was cooled to 4° C. Lastly, it was maintained at 25° C. for 1 hour for annealing. After that, 1 µL of T4 polynucleotide kinase, 1 µL of T4 RNA ligase were added into the reaction mixture, and further incubated at 25° C. for 1 hour.

TABLE 10

| Composition | Content amount |
|---|---|
| puromycin-linker | 22 pmol |
| mRNA | 20 pmol |
| 10 × T4 RNA ligase buffer | 2 µL |
| 0.1% BSA | 1.2 µL |
| Ultra pure water | remains |
| Total | 20 |

The puromycin-linker (FIG. 9) was prepared using the method described in the following reference.

Reference: Mochizuki Y, Biyani M, Tsuji-Ueno S, Suzuki M, Nishigaki K, Husimi Y, and Nemoto N. (2011) One-pot preparation of mRNA/cDNA display by a novel and versatile puromycin-linker DNA. ACS Comb. Sci., 13, 478-485

Namely, the "puromycin segment (PS)", and "short biotin segment (SBS)", which were obtained from GeneWorld Ltd. (Tokyo, Japan), which were modified oligonucleotide to be used for manufacturing hot biotin segment & puromycin-linker—(Short Biotin-segment Puromycin (SBP)-linker). The PS has the following structure.

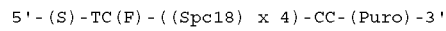

Here, (S) represents 5'-thiol modifier C6, (F) represents fluorescein-dT. (Puro) represents puromycin CPG, and (Spc18) represents the spacer-phosphoramidite 18. The SBS has the following structure.

[SEQ. ID NO. 14]

Here, (T) represents the amino modifier C6 dT, and (T-B) represents the biotin dT.

(rG) represents ribo G. EMCS was purchased from Dojindo laboratories (Kumamoto, Japan). The puromycin-linker was chemically synthesized by crosslinking 2 segments (puromycin segment (PS) and the short biotin segment (SBS)) with EMCS (N-(6-maleimidocaproyloxy) succinimide).

Figure 10:
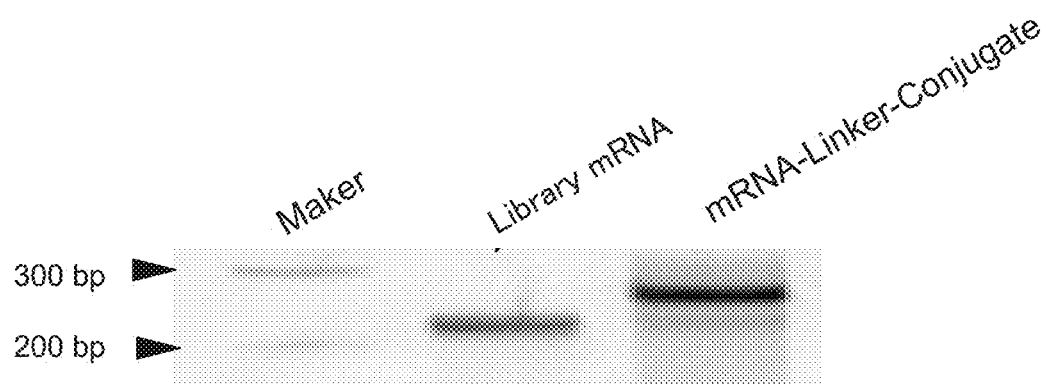
FIG. 10 is a photograph of electrophoresis result for ligation product of mRNA with puromycin-linker.

According to the conventional method, the ligation products were confirmed by using 6% PAGE electrophoresis. The results were shown in FIG. 10. As shown in FIG. 10, on the basis of the band positions of the library mRNA obtained from transcription from DNA library, and mRNA bound to the puromycin-linker, it was demonstrated that both of the transcription from DNA library to mRNA, and the ligation of mRNA and the puromycin-linker were conducted without problems, and then the mRNA-linker-conjugate was obtained.

(3) Formation of the mRNA-Protein Conjugate

The mRNA-linker-conjugate, fractionated by using FACS as described above, was translated by using cell free translation system as follows. The reaction mixture having the composition shown in the following Table 11 was prepared and adjusted to 25 μL with Ultra pure water, and then it was reacted at 37° C. for 15 minutes. After that, 5 μL of 3 M KCl and 1.5 μL of 1 M MgCl$_2$ were added into the reaction mixture. Then, the mixture was further reacted at 37° C. for 40 minutes to obtain the mRNA-protein conjugate (the target binding molecule).

TABLE 11

| Composition | Content amount |
|---|---|
| PURE flex Solution I (GeneFrontier Corp.) | 12.5 μL |
| PURE flex Solution II (GeneFrontier Corp.) | 1.25 μL |
| PURE flex Solution III (GeneFrontier Corp.) | 1.25 μL |
| mRNA-linker ligation product | 4 pmol |
| Ultra pure water | remains |
| Total | 25 μL |

(4) Preparation of the Fluorescent Liposome Conjugate

The fluorescent liposome obtained in the example 1 and the mRNA-protein conjugate obtained as described above were mixed at ambient to obtain the fluorescent liposome conjugate.

(5) Fractionation of the Liposome by Using FACS

Designated tank of FACS (Cell Sorter SH800: SONY Business solutions Corporation) was filled with Ultra pure water up to the predetermined volume, and then the software was launched. After the sorting tip was set, operation was conducted according to the instruction from the software. During the operation, bubbles generated on the filter were removed. Subsequently, set-up of the sample flow path and droplet formation conditions for the fractionation were conducted by using specialized beads for automatic set-up.

When the obtained fluorescent liposome conjugates were analyzed and fractionated by using FACS, prior to them, the liposome suspension was filtrated by using the filter with the pore size, 35 μm, to avoid the stuck of the sample flow path with the liposome. From the results of the histogram analysis, high area was chosen to fractionate the objective fluorescent liposome.

(Example 3) Purification of the mRNA/cDNA-Protein Conjugate and cDNA (1) Removal of the Fluorescent Liposome From the fluorescent liposome conjugated fractionated in the example 2, the fluorescent liposomes were removed by using the centrifugation to obtain the mRNA-linker-protein conjugate.

(2) Purification by Using the Magnetic Beads

The streptavidin (SA) magnetic beads (Dynabeads MyOne Streptavidin C1: Invitrogen) was washed according to the instructions. Then, necessary amount for immobilization of the mRNA-protein conjugate was taken into Eppendorf tube, and left the tube to stand on the magnetic stand for 1 minute. After that, the supernatant was removed, and resuspended with the solution A (100 mM NaOH, 50 mM NaCl). After tapping of the tube for 1 to 2 minutes, the tube was left to stand for 1 minute on the magnetic stand. After that, the same procedure was repeated once by using the solution A, and then the same procedure was repeated once by using the solution B.

Equal volume of the 2× binding buffer (20 mM Tris-HCl containing 2 mM EDTA, 2 M NaCl, 0.2% Tween 20, and 500 mM EDTA (pH 8.0)) was added to the mRNA-protein conjugate from which the fluorescent liposomes were removed, and it was incubated with the streptavidin (SA) magnetic beads at ambient for 60 minutes. Eppendorf tube was left to stand on the magnetic stand for 1 minute, and then the supernatant was removed. 200 μL of 1× binding buffer was added to the tube, it was tapped for 1 to 2 minutes. After that, the tube was left to stand on the magnetic stand for 1 minute to remove the supernatant. The procedure was repeated twice to obtain the mRNA-protein conjugate immobilized on the streptavidin (SA) magnetic beads.

(3) cDNA Synthesis by Using Reverse Transcription

The reaction mixture having the composition shown in the following Table 12 was added to the immobilized mRNA-protein conjugate, and incubated at 42° C. for 30 minutes for reverse transcription. By this, the mRNA/cDNA-protein conjugate which is still immobilized on the streptavidin (SA) magnetic beads were prepared.

TABLE 12

| Composition | Content amount (μL) |
|---|---|
| 2.5 mM dNTP MIX (Takara Bio Inc.) | 6 |
| 5 × first strand buffer (Invitrogen) | 6 |
| nuclease free water | 15 |
| Super Scripy III Reverse Transcriptase (Invitrogen) | 1 |
| 0.1M DTT | 1.5 |

(4) Purification of cDNA

The mRNA/cDNA-protein conjugate immobilized on the streptavidin (SA) magnetic beads were once washed by using 1×NEB 4 buffer. After that, 40 μL of 1×NEB 4 buffer containing 10 U of endonuclease V (New England Biolabs) was added to them, and then incubated at 37° C. for 60 minutes to elute the cDNA display molecule bound to the streptavidin (SA) magnetic beads.

(5) Measurement of Binding Activity According to BioLayer Interferometry

By using Octet 384 (Fortebio), binding activities of human serum albumin (herein below, it is referred to as HSA) against VHH clone A or VHH clone B, both of which are immobilized on Ni-NTA sensor chip. 200 μL of each sample solution is added into the wells of the 96 well plate for the measurement. Prior to measurement, a tip of Dip and Read™ Ni-NTA (NTA) Biosensors (Fortebio) is immersed in 200 μL of PBST containing 0.05% Tween 20 (pH 7.4) for 10 minutes to hydrate the chip.

Order of the measurement per run is as follows: 1) Baseline step: 30 seconds measurement in PBST, 2) Loading step: 120 seconds measurement by using 21 times diluted VHH with PBST, 3) Baseline step: 30 seconds measurement in PBST, 4) Association step: 120 seconds measurement by using 400 nM HSA diluted with PBST, 5) dissociation step: 120 seconds measurement in PBST, 6) Regeneration step: 5 seconds measurement in Glycine-HCl (pH 2.2) and 30 seconds measurement in PBST. Regeneration step is repeated 3 times. After that, HAS is diluted in 2-fold dilution, and the samples are measured 6 times. Then, the binding activities are calculated by using Octet software (Fortebio) for Global Fitting, in this fitting, the reference is the value at the concentration 0 nM of HSA (see FIG. 4). As a result, dissociation equilibrium constant, KD, of the VHH clone A and that of the clone B to HAS are respectively $9.66 \times 10^{-9}$ M, and $2.76 \times 10^{-8}$ M. VHH clone A includes CDR3 sequence shown in SEQ ID NO.37, and VHH clone B includes CDR3 sequence shown in SEQ ID NO.38.

(Example 4) Each Analysis after Screening (1) Analysis by Using FACS

Figure 11A:
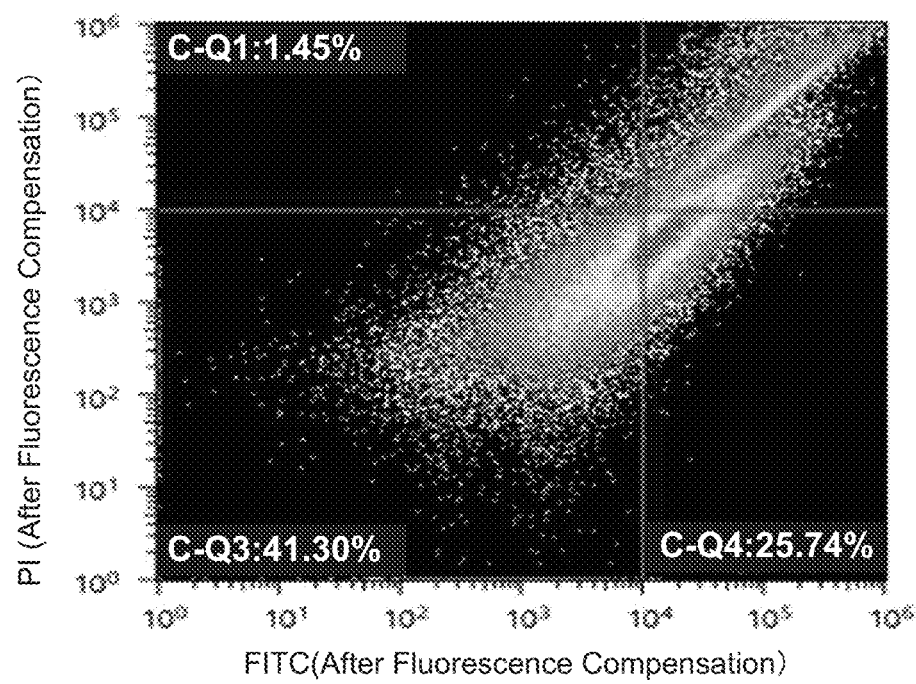
FIG. 11A is the drawing showing the FACS analysis results of the fluorescent liposome at $1^{st}$ high speed screening cycle of the present invention.
Figure 11B:
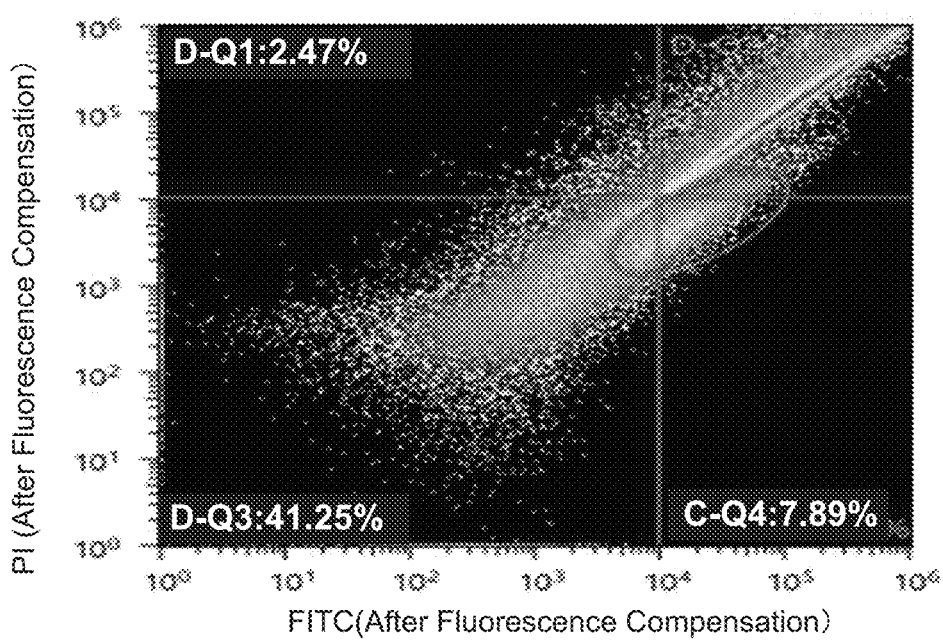
FIG. 11B is the drawing showing the FACS analysis results of the fluorescent liposome at $2^{nd}$ high speed screening cycle of the present invention.
Figure 11C:
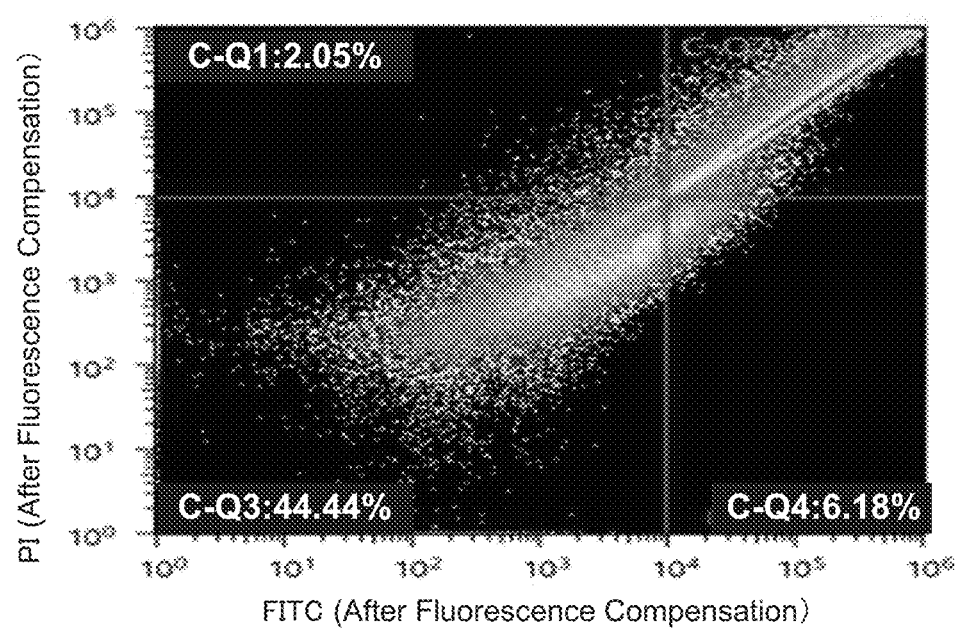
FIG. 11C is the drawing showing the FACS analysis results of the fluorescent liposome at $3^{rd}$ high speed screening cycle of the present invention.

Analysis of the screening results by using FACS of the fluorescent liposome conjugate, which was obtained in the example 1 to 3, in the 1$^{st}$ to 3$^{rd}$ cycles of in vitro selection shown in FIG. 1A, which was shown in FIGS. 11A to 11C. These histograms showed that the size or density of the fluorescent liposome conjugate to be fractionated were varied; however, the properties of regions themselves were not changed; and the fluorescent liposome conjugate was able to be fractionated in the screening with in vitro selection cycles.

(2) Electrophoresis of the PCR Products of the cDNA Display Molecule

Figure 12:
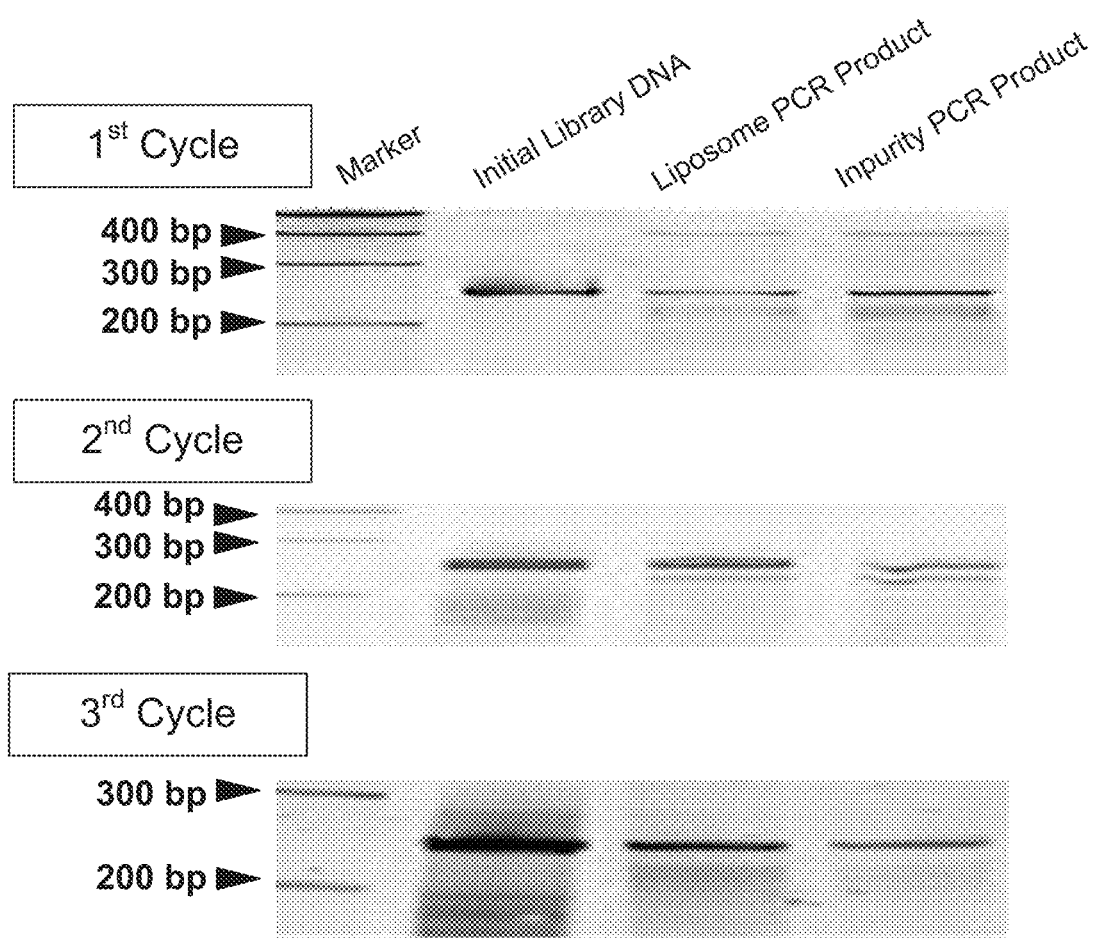
FIG. 12 is the photograph of electrophoresis for PCR product of cDNA display molecule after the $1^{st}$ to $3^{rd}$ screening cycle of the present invention.

The cDNA display molecules obtained in the Example 3 were eluted, and PCR was conducted by using the following primers, according to the conventional method. After that, according to the conventional method, the PCR products were subjected to 6% PAGE electrophoresis. The results of the electrophoresis demonstrated that the band of PCR products became thicker in later screening (cycle numbers of in vitro selection became large). By this, it was shown that the molecule numbers obtained when the area of the liposome was fractionated by using FACS. In contrast, since the bands of the contaminants became thinner, it was shown that the translation products without the properties functions to the liposome were selected in the DNA library (FIG. 12).

```
Forward primer:
                                        (SEQ. ID NO. 6)
GATCCCGCGAAATTAATACGACTCACTATAGGGAGACCACAACGGTTTCCC Reverse primer:
                                        (SEQ. ID NO. 7)
TTTCCCCGCCGCCCCCCGTCCT
```

(2) Analysis of the Cloning Sequence

In order to confirm degree of convergence of the DNA library in detail, cloning sequence analysis by using *E. coli* was conducted. Experiment protocol was as follows.

As liquid medium for *E. coli* culture plate or culture medium, 5 g of Bacto Trypton (Invitrogen), 2.5 g Bacto Yeast extract (Invitrogen), and 5 g NaCl were mixed, and adjusted to 500 mL by using MilliQ water, and then autoclaved for sterilization. After the temperature of the medium became not over than 40° C., 50 mg of ampicillin was added to the medium. For *E. coli* colony culture plate medium, 7.5 g of agar was further added to prepare agar plate. Before the agar plate was solidified, the agar medium was poured into the plate so as to have about 0.5 cm of thickness. Immediately before plating *E. coli*, both 100 μL of 100 mM IPTG and 20 μL of 50 mg/ml X-Gal were soaked in each plate.

In order to express DNA obtained in the cycles of in vitro selection in *E. coli*, the DNAs were ligated to plasmids. The reaction was conducted in the solution having the composition shown in the following Table 13 was prepared by using MilliQ water for 1 hour at ambient.

TABLE 13

| Composition | Content amount (μL) |
| --- | --- |
| 2 × Rapid Ligation buffer | 5 |
| pGEM vector (Promega) | 1 |
| PCR product | 1/3 volume of pGEM vector |

TABLE 13-continued

| Composition | Content amount (μL) |
| --- | --- |
| T4 DNA ligase | 1 |
| MilliQ water | remains |
| Total amount | 10 |

3 μL of the vector-ligation products were added into 40 μL of the competent cell solution, and then reacted for 30 minutes on ice. After the reaction, they were left to stand at 42° C. for 30 seconds in the incubator to give heat shock. Subsequently, they were transferred on ice immediately, again reacted for 2 minutes. After that, 470 μL of SOC culture medium was added to the culture medium at 37° C. for 1 hour for shaking culture to prepare the *E. coli* containing solution. 100 μL of the *E. coli* containing solution was plated on each culture plate and incubated at 37° C. for 12 to 16 hours to form colonies. Colonies were individually picked up, and transferred into the liquid medium and then, cultured at 37° C. for 12 to 16 hours. After the cultivation, the obtained plasmid was purified, according to the instruction manual attached with the purification kit (Qiagen).

Sequencing was ordered to Eurofins. From the sequence results, one of the amino acid sequences among the obtained peptide has the following sequence.

```
                                        [SEQ. ID NO. 8]
Thr Asp Gln Phe Lys Arg Cys Ala Arg Thr Met Glu

Lys Val Thr Gln Cys Pro Met Ile Glu Thr Lys Glu

Gly Ala Thr Lys Ile Glu Ser Pro Gln Arg
```

Figure 13:
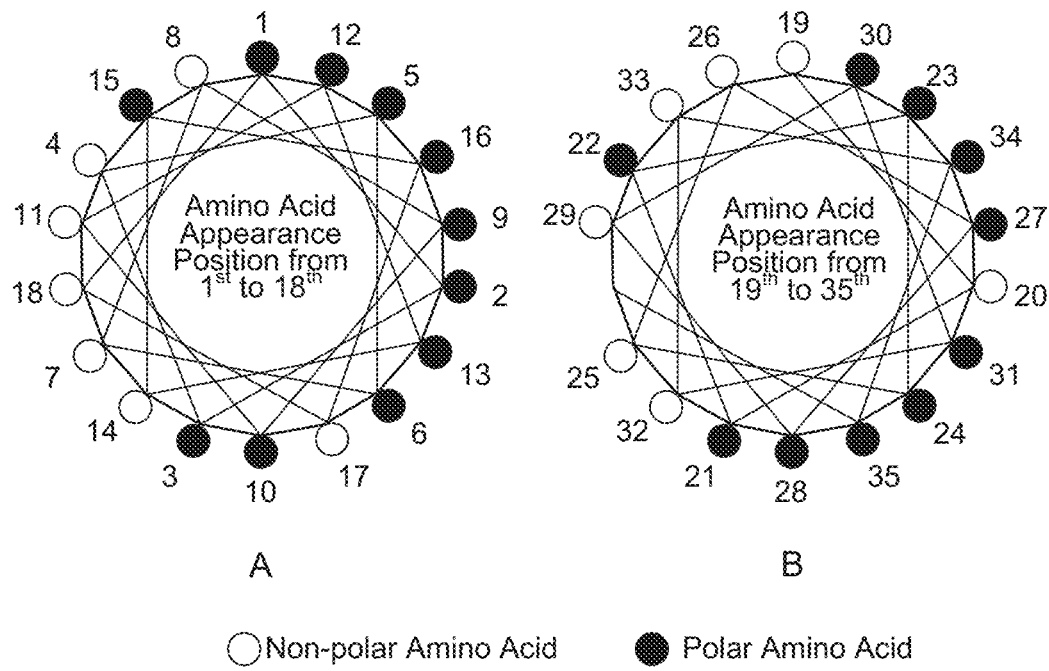
FIG. 13 is the drawing showing the amino acid sequence of the peptide obtained from the cloning sequence and 2 a helix wheels A and B, on which the sequence is arranged. Wherein, A shows appearance positions between Nos. 1 to 18 and B sows those between Nos, and they are shown in parallel.

The sequences were arranged on two α-helix wheels, which were divided with the appearance positions of the amino acids from 1 to 18, and 19 to 35 (FIGS. 13A and B) to confirm the appearance positions both of the polar amino acid and the non-polar amino acid. The amphiphilic helix similar to those as initially designed sequence (FIG. 5), and it showed that the objective screening was conducted.

(Example 5) Modification of the Liposome with the Membrane-Binding Fusion Protein The fusion protein binding to the liposome membrane was prepared, and then the liposome surface was modified by using the target molecules.

Figure 14A:
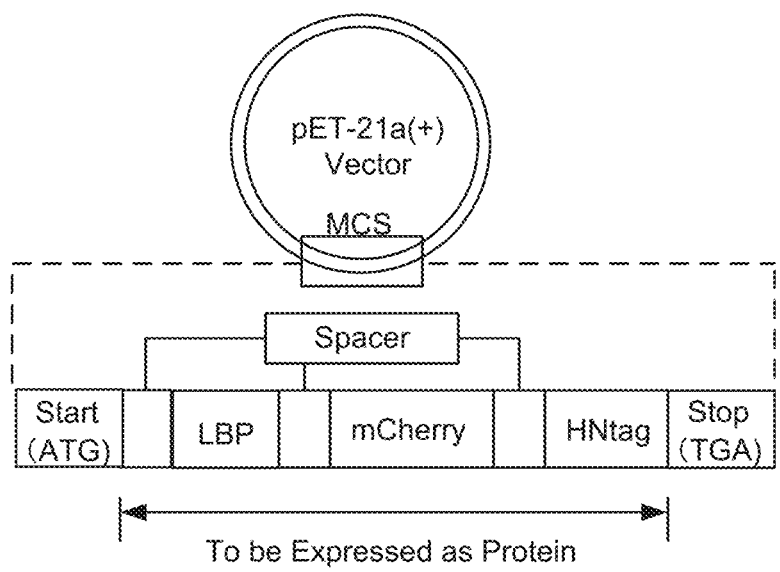
FIG. 14A is the schematic figure showing a gene sequence of the fused protein introduced into a vector.
Figure 14B:
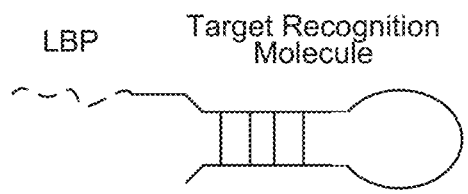
FIG. 14B is the schematic figure showing the structure of the target recognition molecule.

Firstly, the sequence comprising LB-1 peptide (SEQ. ID NO. 9) coding sequence, which functions as the anchor against the liposome membrane, and the sequence coding the red fluorescent dye, mCherry2, as the label molecule, was synthesized by Eurofins. According to the conventional method, the sequence was inserted into the multi-cloning sites of pET-21a (+) vector (FIG. 14A). Next, according to the conventional method, the vector was introduced into *E. coli* to express the fusion protein of LB-1 and mCherry2. Then, according to the conventional method, the purification was conducted with His-tag to obtain the fusion protein solution. The obtained fusion protein was schematically shown in FIG. 14B.

```
                                        [SEQ. ID NO. 9]
Arg His Ser Lys Ser Leu Pro Ser Arg Val Ile Pro

Arg Ala Asp Pro Arg Thr Lys Thr Arg Arg Arg

Arg Arg Lys Arg Thr Leu Cys (F)
```

Figure 15:
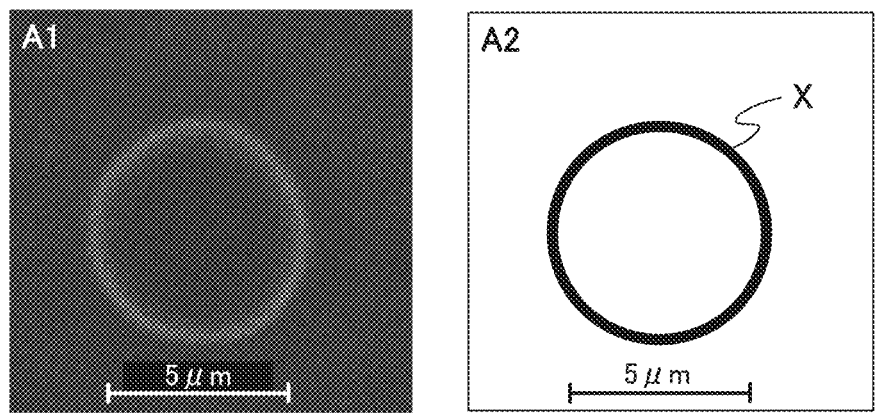
FIG. 15 is a fluorescent microscope image of the liposome reacted with mCherry-LB-1 fusion protein or sole mCherry. A1 is the fluorescent microscope image of the liposome to which 2 µM of mCherry-LB-1 fusion protein is binding on its outer membrane. B1 is the fluorescent microscope image of the liposome to which 2 µM of mCherry is solely binding on its outer membrane. Both of A2 and B2 are the schematic figures of A1 and B1 respectively. X shows the liposome membrane having bright red fluorescence and Y shows the liposome membrane having dark red fluorescence.
Figure 15:
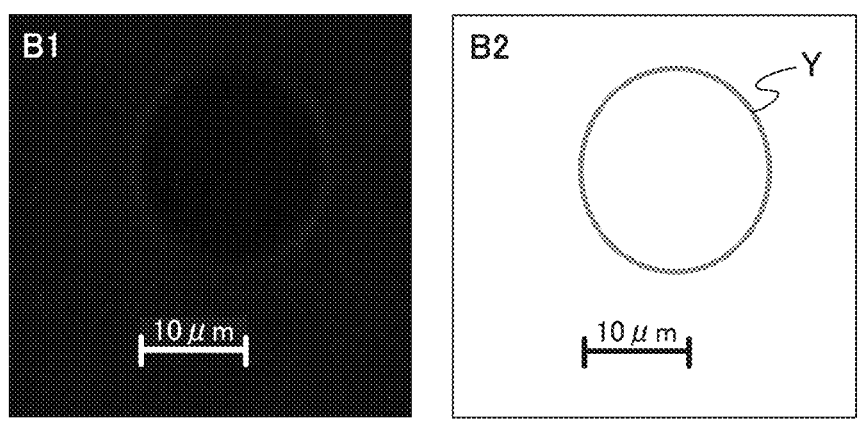

The liposome solution without the fluorescent dye was prepared as the same as that in Example 1, and then the fusion protein solution was added into the liposome solution so as to be the concentration of mCherry2 at 2 μM. The sample was excited with a light of 587 nm to be observes. As a result, it was observed that red fluorescent of mCherry2 was located on the liposome to which the fusion protein was added (FIG. 15A). On the other hand, the liposome to which solely mCherry 2 was added showed low fluorescent intensity, and the surface of the liposome was not sufficiently labeled (FIG. 15B). By this, it was shown that the LB-1 peptide bound to the liposome membrane to modify the labeled molecule, mCherry2.

(Example 6) Screening by Using RNA Aptamer

Screening was conducted by using silica beads (Micromod) as the spherical shape molecule, streptavidin binging RNA aptamer (hereinbelow, it is sometimes referred to as "SAB-RNA aptamer".) or streptavidin unbinding RNA aptamer (hereinbelow, it is sometimes referred to as "SAN-RNA aptamer") as the target detection molecule.
(1) Preparation of DNA and RNA Aptamer In order to prepare DNA for SAB-RNA aptamer preparation, primers (5' primer and 3' primer) having the following sequence were manufactured.

```
5' primer:
                                       (SEQ. ID NO. 10)
AGTAATACGACTCACTATAGGGAGTCGACCGACCAGAATCATGCAAGTGC

GTAAGATAGTCGCGGGCCGGGGGCGTATTATGTGCGTCTACATCTAGACT

CAT

3' primer:
                                       (SEQ. ID NO. 11)
ATGAGTCTAGATGTAGACGCACATA
```

Also, in order to prepare DNA for SAN-RNA aptamer, the primer (5' primer) having the following sequence was manufactured. 3' primer was the same as that used in the manufacture of DNA for SAB-RNA aptamer.

```
5' primer:
                                       (SEQ. ID NO. 12)
AGTAATACGACTCACTATAGGGAGTCGACCGACCAGAAATGGATAACAAA

TTCAACAAAGAACAACAATATGTGCGTCTACATCTAGACTCAT
```

By using the primers described above, the reaction mixture shown in the following Table 14 was prepared; and then, both of DNA for SAB-RNA aptamer and DNA for SAN-RNA aptamer were manufactured by using PrimeSTAR HS DNA Polymerase (Takara Bio Inc.) with overlap extension (overlap extension). Overlap extension was conducted under the following conditions: reaction for 1 minute at 98° C., 5 seconds at 61° C., 30 second at 72° C., and then cooled to 10° C. After the reaction, it was subjected to the purification by using FavorPrep PCR Clean-Up Mini Kit (Favorgen) according to the manual attached thereto.

TABLE 14

| Composition of reaction solution for overlap extension solution | Amount (μL) |
| --- | --- |
| 5 × PrimeSTAR Buffer | 5 |
| dNTP Mixture | 2 |

TABLE 14-continued

| Composition of reaction solution for overlap extension solution | Amount (μL) |
| --- | --- |
| 20 μM 5' primer | 0.5 |
| 20 μM 3' primer | 0.5 |
| 2.5 U/μL PrimeSTAR HS DNA Polymerase | 0.25 |
| Ultra pure water | 16.75 |

Figure 16:
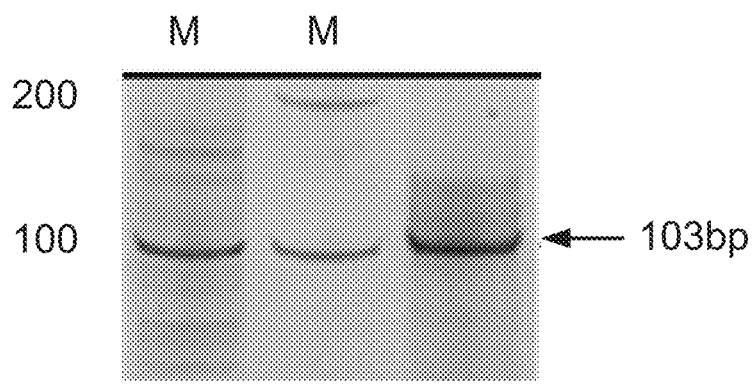
FIG. 16 is the electrophoresis image showing DNA of streptavidin-bound RNA aptamer.

DNA obtained through the purification as described above was subjected to gel electrophoresis under the conditions of 200 V for 30 minutes. As a result, a band of 103 bp DNA for SAB-RNA aptamer the lane at right end was confirmed (FIG. 16). In FIG. 16, M represents a marker.

Figure 17:
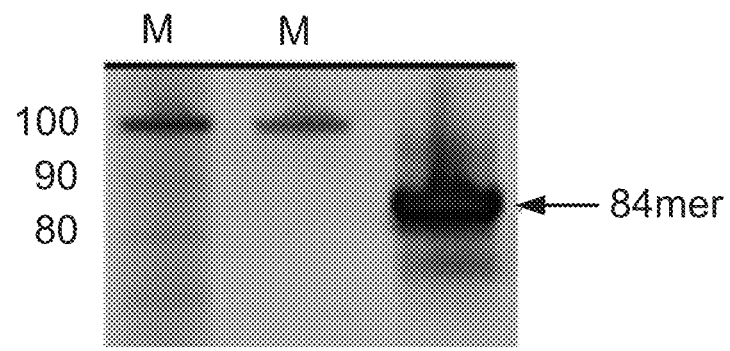
FIG. 17 is the electrophoresis image showing streptavidin-bound RNA aptamer.

By using T7 RiboMAX (registered trademark) Express Large Scale RNA Production System (Promega), the reaction mixture shown in the following Table 15 was prepared and conducted transcription at 37° C. for 3 hours to obtain RNA. After transcription, 4 μL of RQ1 DNase (Promega) was added, and then it was reacted at 37° C. for 30 minutes to degrade the template DNA. Then, the gel was sliced for purification, and then gel electrophoresis was conducted under the conditions of 200 V for 30 minutes. As a result, the band of the objective DNA for SAB-RNA aptamer, 84 mer, was confirmed at the right end lane (see, FIG. 17). In FIG. 17, M represents the marker.

TABLE 15

| Composition for transcription reaction solution | Amount (μL) |
| --- | --- |
| 25 mM rNTP | 12 |
| DNA | 16 |
| T7 Transcription 5 × Buffer | 8 |
| Enzyme Mix (T7) | 4 |

(2) SAB-RNA Aptamer Binding Assay

In order to conduct binding assay for SAB-RNA aptamer obtained above and streptavidin, the binding buffer (pH 7.4) was prepared. HEPES, MgCl$_2$ and NaCl were purchased from Wako Pure Chemical. The composition for the assay buffer was shown in the following Table 16, and the buffer volume was adjusted to 200 mL with Ultra pure water. The solution having the composition shown in Table 16 was adjusted to 800 mL by adding Ultra pure water to prepare 30% glycerol binding buffer (pH7.4).

TABLE 16

| Composition of the solution | Buffer for binding assay Amount | Glycerol binding buffer Amount |
| --- | --- | --- |
| HEPES (Wako Pure Chemical Corporation) | 9.5 g | 9.5 g |
| 1M MgCl$_2$ (Wako Pure Chemical Corporation) | 8 mL | 8 mL |
| NaCl (Wako Pure Chemical Corporation) | 4.7 g | 4.7 g |
| Glycerol | — | 3 mL |
| Ultra pure water | remains | remains |
| Total amount | 200 mL | 800 mL |

Figure 18:
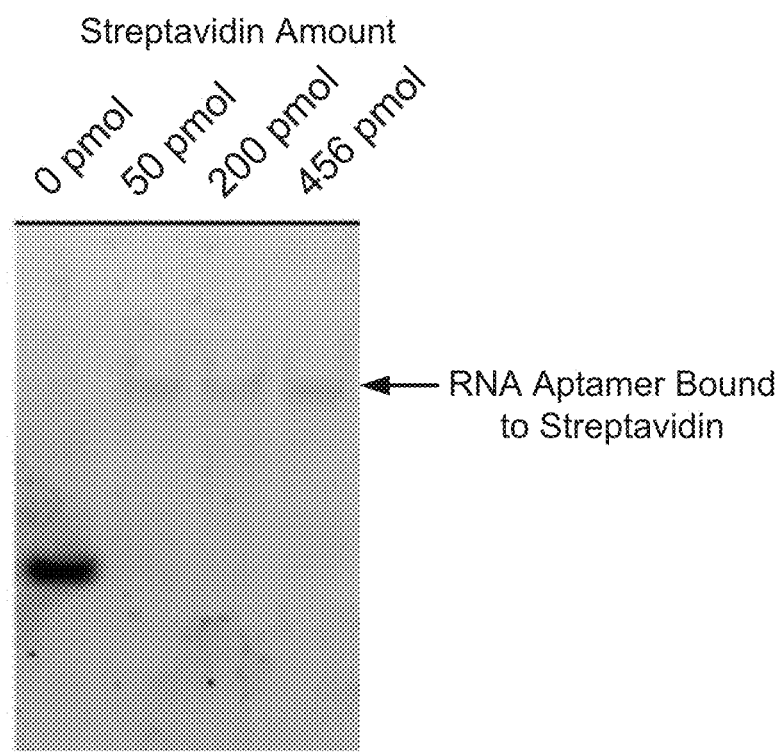
FIG. 18 is the electrophoresis image showing streptavidin-bound RNA aptamer.

0 pmol, 200 pmol or 456 pmol of streptavidin was added into 1.25 μL of the binding buffer, and the volume of the reaction mixture was adjusted with Ultra pure water to adjust final concentration of the SAB-RNA aptamer so as to be 1 μM. The reaction mixture was reacted at 25° C. for 1 hour, and 2 μL of 30% glycerol binding buffer was added, and then the sample was subjected to non-polyacrylamide gel electrophoresis at 200 V for 30 minutes. As a result, it was demonstrated that a band having smaller mobility (pointed with an arrow in the figure) with streptavidin compared that without streptavidin appeared (FIG. 18). The reason for the smaller mobility was binding of streptavidin and the SAB-RNA aptamer. From the results, it was demonstrated that the SAB-RNA aptamer bound to streptavidin.

(3) Immobilization of Streptavidin on the Spherical Structure

As the spherical structure on which the target molecule, streptavidin was immobilized, the silica beads of which surface was modified COOH group having the particle diameter, 1.5 µm, and encapsulating rhodamine B (product name: Sicaster-red F, Micromod) was employed. The COOH groups on the silica beads were turned to NHS ester, and then streptavidin as the target molecule (a protein) was immobilized to the NHS-carboxyl group in the following protocols.

Firstly, 20 µL of the suspension containing the silica beads was added into the centrifuge tube, and the tube was centrifuged at 15,000 rpm for 5 minutes to remove the supernatant. Then, 100 µL of dimethylformamide (DMF) was added to the tube and then stirred. After that, the tube was centrifuged at 15,000 rpm for 5 minutes to remove the supernatant. The procedure to add DMF to the tube and centrifuged at 15,000 rpm for 5 minutes at ambient to remove the supernatant was repeated three times. Subsequently, both of 50 µL of 200 mM NHS solution and 50 µL of 200 mM EDC were added into the tube and stirred at 25° C. for 2 hours.

After finishing stirring, the solution was centrifuged at 15,000 rpm for 5 minutes to remove the supernatant. 100 µL of DMF was added to the tube and well stirred, and then the tube was centrifuged at 15,000 rpm for 5 minutes to remove the supernatant. The procedure to add DMF to the tube and centrifuged to remove the supernatant was repeated three times. Subsequently, 100 µL of 10 µM streptavidin (Funakoshi Co. Ltd.) was added into the tube and then stirred at 25° C. overnight. After stirring, the tube was centrifuged at 15,000 rpm for 5 minutes to remove the supernatant. The procedure that 100 µL of Ultra pure water was added into the tube and then centrifuged at 15,000 rpm for 5 minutes to remove was repeated three times. Then, 20 µL of the 4-hold dilution of the binding buffer was added to the tube to disperse the silica beads (spherical structure) to which streptavidin were bound.

The obtained spherical structure and fluorescein labelled biotin were reacted as follows, and then, the amount of the immobilized streptavidin was determined by using fluorescent intensity of FITC. Firstly, 1 pmol biotin 4-fluorescein (Sigma-Aldrich Co. LLC.) was added to 1 µL of the dispersion, and 20 µL of the binding buffer was further added. After incubation at 25° C. for 1 hour, the tube was centrifuged at 15,000 rpm for 5 minutes to remove the supernatant. Then, the procedure 20 µL of binding buffer was added into the tube and centrifuged at 15,000 rpm for 5 minutes to remove the supernatant was repeated three times. Lastly, 20 µL of the binding buffer was added into the tube to prepare the sample for the fluorescent intensity determination.

Figure 19:
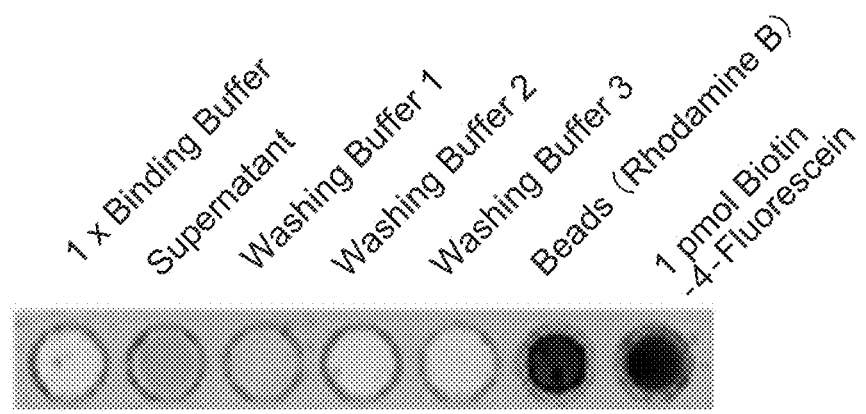
FIG. 19 is the electrophoresis image showing fluorescent intensity of reaction products of silica beads labeled with streptavidin-immobilized rhodamine B and biotin labeled with fluorescein in FITC.

In order to avoid the affection by rhodamine B in the silica beads, the fluorescent intensity of the biotin 4-fluorescein released in the supernatant, obtained from the centrifugation after the incubation with the biotin 4-fluorescein (hereinbelow, it is sometimes referred to as "Sup".), and that in the supernatant washed with the binding buffer (hereinbelow, it is sometimes referred to as "Wash".) were determined to obtain the immobilized amount of streptavidin (FIG. 19).

Sum of the fluorescent intensity of Sup plus Wash (hereinbelow, it is sometimes referred to as "Sup+Wash".), and that of the biotin 4-fluorescein (hereinbelow, it is sometimes referred to as "B4F".) were entirely set as 100. The ratio of Sup+Wash: B4F was 23.82: 76.18. Considering that the measured amount of each sample was 20 µL, and that of the added biotin 4-fluorescein was 1 pmol, total amount of the biotin 4-fluorescein released in Sup and Wash was 0.31 pmol. As a result, the amount of the biotin 4-fluorescein bound to streptavidin immobilized on 1 µL of the silica beads used was 0.69 pmol.

(4) Sorting by Using FACS

Each sorting buffer having the composition shown in the following Table 17 was prepared by using the following 2 types of the silica beads: one was the silica beads with immobilized streptavidin-encapsulated rhodamine B (hereinbelow, it is sometimes referred to as "plus beads".); and another one was those without immobilized streptavidin and fluorescence label, Sicastar (Micromod, hereinbelow, it is sometimes referred to as "minus beads".), SAB-RNA aptamer and SAN-RNA aptamer, and amount the buffer was adjusted with Ultra pure water to 5 µL.

TABLE 17

| Composition of the sorting solution | amount | Final conc. (nM) |
|---|---|---|
| Plus beads | 0.1 µL | — |
| Minus beads | 0.1 µL | — |
| SAB-RNA aptamer | | 7, 0.7, 0.07, 0.007 |
| SAN-RNA aptamer | | 70 |
| Binding buffer (×4 dilution) | 0.75 µL | — |

Figure 20:
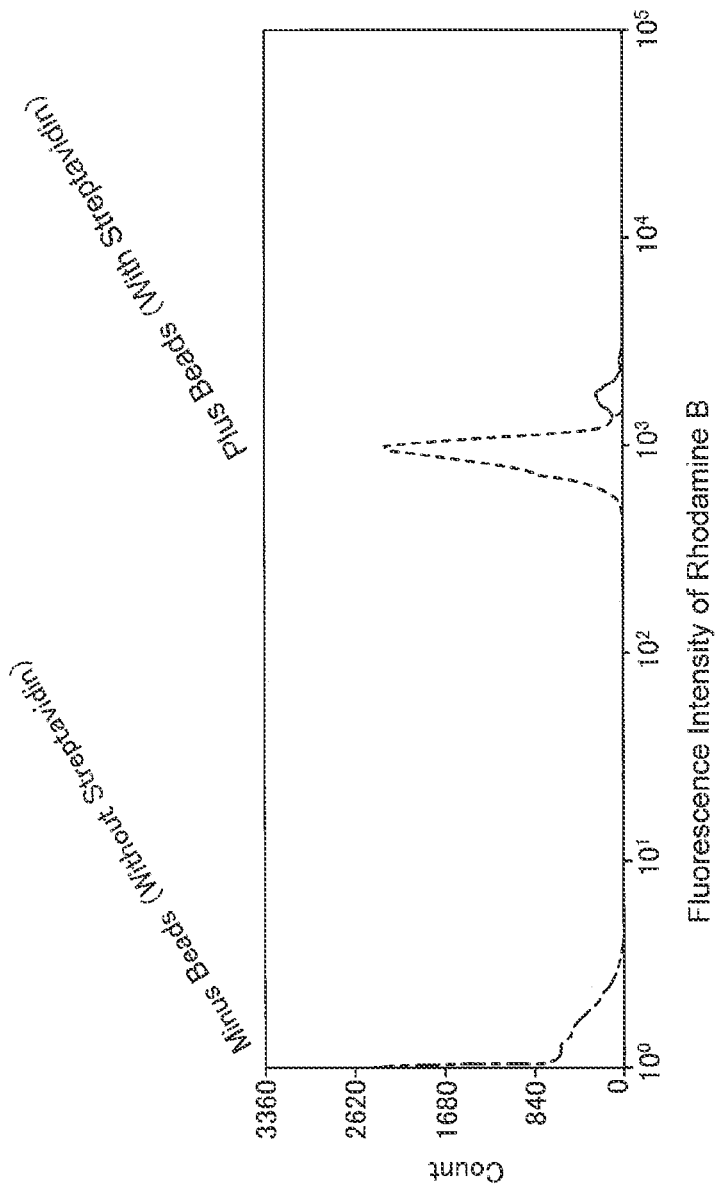
FIG. 20 is a graph showing a sorting area of rhodamine B by using FACS.

The sorting buffer containing the compositions shown in the Table 17 was respectively incubated at 25° C. for 1 hour; and then sorting was conducted by using the diluted solution which was adjusted to 2 mL with the binding buffer, and MoFlo Astrois EQ High Speed Cell Sorter (Beckman coulter). As a result, it was confirmed that the area having rhodamine BB close to around $10^3$ was appeared (FIG. 20). The sorting was conducted under setting the area as the fixed Sicastar-redF, and that closed to $10^0$ to $10^1$ as Sicastar.

(5) Selection

The sorting solution containing either of the plus beads or the minus beads was sorted respectively with the cell sorter. One L of 24 µM biotin 4-fluorescein was added into 200 µL of the sorted solution and incubated at 25° C. for 1 hour. Then, the SAB-RNA aptamer or the SAN-RNA aptamer was released from the plus beads or the minus beads with competitive elution. After that, the tubes contained the solution were centrifuged at 15,000 rpm for 5 minutes, and RNA in the supernatant was collected by using ethanol precipitation.

Both of 6.5 µL of Ultra pure water and 0.5 µL of 10 µM 3'-primer (SEQ. ID NO. 11) were added into the solution containing the collected RNA, and then they were incubated at 65° C. for 5 minutes. The tubes were transferred on ice, and then, 8 µL of 2.5 mM dNTPs mix, 4 µL of the buffer and 1 µL of ReverTra Ace (TOYOBO Co. Ltd.) were added into the tube to conduct reverse transcription at 60° C. for 30 minutes.

After that, the tubes were heated at 99° C. for 5 minutes. PCR reaction mixture having the composition shown in the following Table 18 was prepared and was added into the tubes to conduct PCR. The reaction conditions were as follows: the cycle containing that at 98° C. for 10 second, at 68° C. for 5 second, and at 72° C. for 7 second were repeated 5 to 20 cycles, and then the mixture was incubated at 72° C.

for 1 minute and cooled to 10° C. T7 primer having the sequence shown as SEQ. ID NO. 13, and 3' primer having that shown in SEQ. ID NO. 11 were used.

TABLE 18

| Composition | Amount (µL) |
|---|---|
| 5 × PrimeSTAR buffer | 5 |
| 2.5 mM dNTP Mixture | 2 |
| 20 µL T7 primer | 0.5 |
| 20 µL 3' primer | 0.5 |
| template DNA | 2 |
| 2.5 U/µL PrimeSTAR HS DNA Polymerase | 0.25 |
| Ultra pure water | 14.75 |

Figure 21:
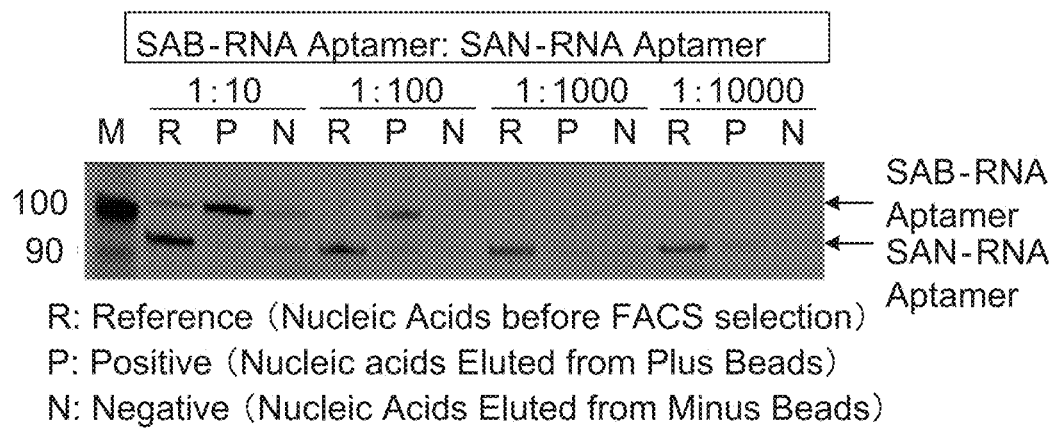
FIG. 21 is the gel electrophoresis image of the FACS sorting results of the PCR products after the streptavidin-bound RNA aptamer and the streptavidin-unbound RNA aptamer were mixed with the ratio of 1:10 to 1:10,000, and then the solution was subjected to 15 cycles of PCR under the predetermined conditions. R shows the nucleic acids before the selection, P shows these eluted from the plus beads, and N shows these eluted from the minus beads, respectively.

By using the obtained PCR products, gel electrophoresis was conducted under the conditions of 8 M urea and 8% acrylamide gel. As a result, when PCR was conducted 15 cycles, it was confirmed that any bands did not appeared at the reference lanes before sorting (shown as R in FIG. 21), but the bands appeared at the positive lanes (shown as P in FIG. 21), when the concentration ratio of SAB-RNA aptamer and SAN-RNA aptamer was 1:10 or 1:100. By these, it was confirmed that the almost all of RNA eluted from the plus beads were SAB-RNA aptamers, and candidate sequences with high affinity were obtained (FIG. 21).

Figure 22:
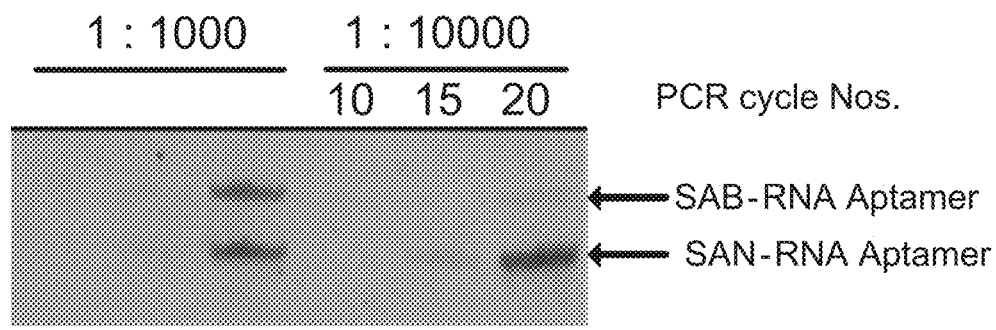
FIG. 22 is the gel electrophoresis image of the FACS sorting results of the PCR products after the streptavidin-bound RNA aptamer and the streptavidin-unbound RNA aptamer were mixed with the ratio of 1:1,000 or 1:10,000, and then the solution was subjected PCR to be conducted 10 cycles, 15 cycles or 20 cycles under the same conditions in FIG. 21. After that, the products were subjected to FACS sorting.
Figure 23:
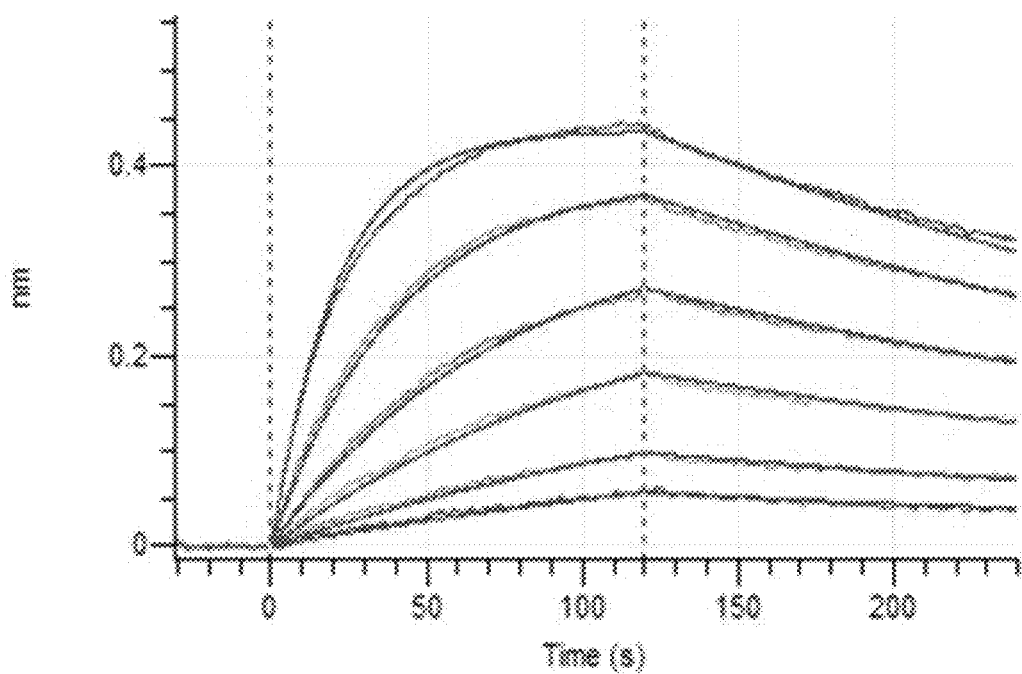
FIG. 23 is the graph showing the binding assay results of Clone A by using Octet384.
Figure 24:
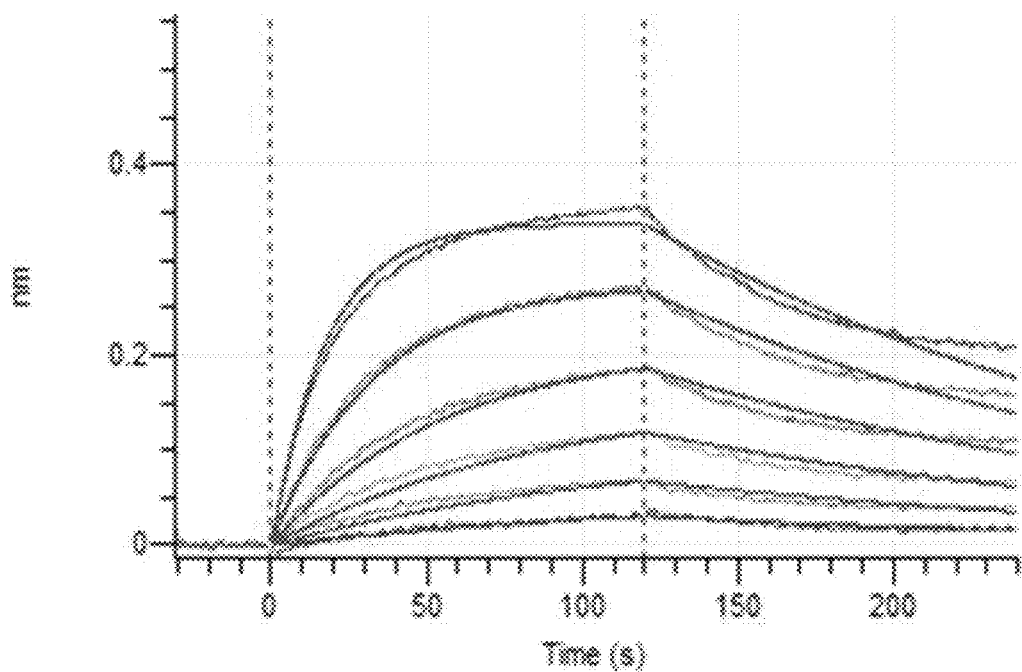
FIG. 24 is the graph showing the binding assay results of Clone B by using Octet384.

When PCR cycle number was 15, SAB-RNA aptamer bands did not appear either the positive lanes or the negative lanes (shown in N in FIG. 21), when the concentration ratio was 1:1,000 or 1:10,000. However, when the concentration ratio was 1:1,000, the bands having the same intensity at the both positions of SAB-RNA aptamer or SAN-RNA aptamer appeared, when the PCR cycle number increased to 20 (FIG. 22).

As described above, the concentration ratio at the screening is estimated 100 to 1,000 times higher. Also, both of the SAB-RNA aptamer and the SAN-RNA aptamer showed the simultaneous band intensity when the concentration ratio was 1:1,000. Therefore, the concentration ratio by using FACS was estimated that it is not less than 600 times. Since the concentration ratio of Prior art 6 was about 60 times, it demonstrated that the concentration ratio reached at least 10 times or higher ratio, compared to that obtained from the conventional method by using the column and the excision as the separation technique. Also, it demonstrated that the present method obtained the molecule having higher specificity in high speed.

(Example 7) Screening of Anti-HER2/ERBB2 Antibody (1) Preparation of DNA Library Encoding Single Variable Domain of Heavy Chain of a Heavy-Chain Antibody (VHH) in the Full-Length Antibody Derived from Alpaca Naive VHH library derived from alpaca provided by RePHAGEN Co. Ltd. is used as a template. Two gene fragments from 1-2 domain of a complementary determining region (hereinbelow, it is referred to as "CDR") or CDR 3 region are amplified by PCR reaction with specific primers; SEQ ID 16 and 17 (Table 19). After that, in order to prepare a fragment comprising T7 promoter, omega (ω) enhancer, kozak consensus sequence, VHH gene, His tag, and liker hybridization region (Ytag), the PCR products are subjected to extension PCR by using primers for overlap PCR, SEQ ID NO: 18 and 19 (Table 19).

TABLE 19

| Primer | Sequences | SEQ ID NO. |
|---|---|---|
| VHH specific | 5'-GAT CCC GCG AAA TTA ATA CGA CTC ACT ATA GGG GAA GTA TTT TTA CAA CAA TTA CCA ACA ACA ACA ACA AAC AAC AAC AAC ATT ACA TTT TAC ATT CTA CAA CTA CAA GCC ACC ATG-3' | 16 |
| | 5'-TTT CCA CGC CGC CCC CCG TCC TGC TTC CGC CGT GAT GAT GAT GAT GGC TGC CTC CCC C-3' | 17 |
| overlap PCR | 5'-GAT CCC GCG AAA TTA ATA CGA CTC ACT ATA GGG GAA GTA TTT TTA CAA CAA TTA CCA ACA ACA ACA ACA AAC AAC AAC AAC ATT ACA TTT TAC ATT CTA CAA CTA CAA GCC ACC ATG-3' | 18 |
| | 5'-TTT CCA CGC CGC CCC CCG TCC TGC TTC CGC CGT GAT GAT GAT GAT GGC TGC CTC CCC C-3' | 19 |

(2) Formation of mRNA-VHH Conjugate

According to the method employed in Example 2, mRNA is transcribed from DNA library obtained above. After that, it is ligated to puromycin linker, and then obtained mRNA-linker conjugate is translated in a cell free system to obtain a translated product, which is shown as follows: the reaction mixture having the composition shown in the following Table 20, the translated products are incubated at 37° C. for 15 minutes, and then, 28.8 µL 3 M KCl and 7.2 µL 1M MgCl$_2$ are added into the mixture. After that, the mixture is further incubated for 20 minutes at 37° C. to obtain the mRNA-VHH conjugate.

TABLE 20

| Composition | Content amount |
|---|---|
| Rabbit Reticulocyte Lysate (Promega) | 52.5 µL |
| 20 × Translation Mix (Promega) | 1.5 µL |
| Ribonuclease inhibitor (40 U/µL) (Promega) | 1.5 µL |
| mRNA/Linker ligation product | 9 pmol |
| Nuclease free water | remains |
| Total | 75 µL |

(3) Preparation of cDNA-VHH Conjugate

The mRNA-VHH conjugate obtained in the above (2) is immobilized on the streptavidin (SA) magnetic beads (Dynabeads MyOne Streptavidin C1: Invitrogen) by using the same method described in the example 3. After that, the reaction mixture having the composition shown in the following Table 21, it is incubated at 42° C. for 30 minutes for reverse transcription to prepare mRNA/cDNA-VHH conjugate, which is referred to as a cDNA display molecule.

TABLE 21

| Composition | Content amount (µL) |
|---|---|
| 25 mM dNTP Mix (Toyobo Life Science) | 3 |
| ReverTra Ace (100 U/µL) (Toyobo Life Science) | 1.5 |
| 5 × ReverTra Ace Buffer (Toyobo Life Science) | 15 |
| Nuclease free water | 55.5 |

(4) Cutting Out from cDNA-VHH Conjugate from the Bead

The immobilized cDNA-VHH conjugate on the streptavidin (SA) magnetic beads obtained in the above (3) is once washed by using 1× His-Tag wash buffer containing 20 mM Sodium phosphate, 0.5M NaCl, 10 mM Imidazole, and 0.05% Tween 20 (pH7.4). After that, 30 µL 1× His-Tag wash buffer containing 10 U RNase T1 (Thermo Fisher Scientific) is added, and then incubated for 15 minutes at 37° C. to elute cDNA display molecules bound to the streptavidin (SA) magnetic beads.

(5) Purification of cDNA-VHH Conjugate

30 µL His Mag Sepharose Ni Beads (GE Health Care) is added into Eppendorf tube. The tube is stood for 1 minute on a magnetic plate, and the supernatant is removed to resuspend by using 1× His-Tag wash buffer. After pipetting for 1 minute, the tube is stood for 1 minute on the magnetic plate. This operation is repeated twice. The elution buffer containing cDNA-VHH conjugate is mixed with His Mag Sepharose Ni Beads, and then the mixture is incubated at room temperature for 30 minutes. After that, the mixture is stood for 1 minute on the magnetic plate to remove the supernatant. 200 µL of 1× His-Tag wash buffer is added to the mixture, and it is pipetted for 1 minute. Then, it is stood for 1 minute on the magnetic plate to remove the supernatant. This operation is repeated twice. 10 µL of 1× His-Tag elution buffer containing 20 mM Sodium phosphate, 0.5M NaCl, 0.25M Imidazole, and 0.05% Tween 20 (pH7.4) is added to the mixture to incubate for 15 minutes at room temperature to elute the cDNA-VHH conjugate, cDNA display molecule.

(6) Immobilization of HER2/ERBB2 to the Spherical Shaped Structure

As a spherical shaped structure for immobilizing the target molecule, HER2/ERBB2 recombinant protein (Sino Biological), Dynabeads MyOne Streptavidin C1, super magnetic polymer beads having a diameter 1.0 µm on which streptavidin is bound are used. The immobilizing procedure is as follows:

Firstly, 50 µL of 1×PBS buffer is added to 25 µg of HER2/ERBB2 recombinant protein, and 7 µL of 1 mM EZ-Link™ Sulfo-NHS-SS-Biotin solution is further added, and then the mixture is incubated at room temperature for 30 minutes. The mixture is purified by using Zeba™ Spin Desalting Column (Thermo Fisher) to recover 85 µL of Biotinylated HER2/ERBB2 recombinant protein.

100 µL of Dynabeads MyOne Streptavidin C1 is added into the Eppendorf tube, and stood on the magnetic plate for 1 minute; and then, the supernatant is removed. After that, 100 µL of 1× Binding buffer containing 10 mM Tris-HCl, 1 M NaCl, 0.1% Tween 20, and 1 mM EDTA (pH 8) is added into the tube to resuspend the beads. After 1-minute pipetting of the suspension, the tube is stood on the magnetic plate for 1 minute, and then, the supernatant is removed. 21 µL of Biotinylated HER2/ERBB2 solution is added into the tube, and the solution is stirred at room temperature for 30 minutes. After that, the tube is stood on the magnetic plate for 1 minute. Then, the beads are sequentially washed with 100 µL of 1× Binding buffer and 100 µL of PBST. Subsequently, 100 µL of PBST is added into the tube to obtain HER2/ERBB2-immobilized beads solution. The protein concentrations of the solutions before and after the immobilization reaction are determined by using NanoDrop™ (Thermo Scientific), and their band intensity ratios on SDS-PAGE are compared to estimate yield of the immobilization reaction.

(7) In Vitro Selection

The cDNA-VHH conjugate, cDNA display molecule, synthesized in (5) described above, and the spherical shaped structure of HER2/ERBB2 prepared in (6) as described above, are subjected to in vitro selection under the conditions shown in the following Table 22 according to the following procedure from Round 1 to 5 (which are abbreviated as R1 to R5).

Amount of mRNA/Linker ligation products for cDNA display synthesis are 192 pmol in R1, 12 pmol in R2, and 6 pmol in R3 to R5. From R2 to R5, in order to remove non-specific adsorbents, preselection is conducted. In detail, 100 µL PBST dilution solution containing the cDNA display is prepared, and then, the molecule is bound to streptavidin beads previously washed with 1× Binding buffer. The solution is stirred at room temperature for 1 to 2 hours, and then the tube is stood on the magnetic plate for 2 minutes to collect the supernatant. After repeating the operation twice, the obtained supernatant is dilute with PBST so as to become 1 µM in R1, and 100 nM in R2 to R4 against the immobilized amount of HER2/ERBB2. After that, the molecule is bound to HER2/ERBB2-immobilized beads, and stirred at room temperature for 1 to 2 hours. The tube is stood on the magnetic plate for 2 minutes, and then the supernatant is removed, and the magnetic beads are washed with 100 µL of PBST, from one to three times. Subsequently, 40 µL of 10 mM TCEP buffer (pH 7 to 8) or 10 mM NaOH solution is added as an elution buffer to the tube and incubated for 5 to 30 minutes to recover eluates.

The elution was performed three times for R1 and R2. Also, the elution was performed twice for R3, R4, and R5. TCEP buffer was added for elution of R1 and R2 of first and second elution, then NaOH solution was added for third elution of R1 and R2. Tor the elution of R3, R4, and R5, only TCEP buffer was added. Obtained elution was purified by using Agencourt AMPure XP (Beckman Coulter), following the instruction manual.

TABLE 22

| Rounds | mRNA/Linker ligation product (cDNA display) | Preselection | Washing times |
|---|---|---|---|
| 1 | 192 pmol | none | 1 time |
| 2 | 12 pmol | 2 times | 3 times |
| 3 | 6 pmol | 2 times | 3 times |
| 4 | 6 pmol | 2 times | 3 times |
| 5 | 6 pmol | 2 times | 3 times |

(8) Amplification of the Sample by PCR

The eluates obtained in the pre-selection described above are subjected to PCR, which is conducted by using Prime-STAR HS DNA Polymerase (Takara Bio Inc.), and PCR reaction mixture having the composition shown in the following table 23. The PCR program is as follows: (1) 98° C. for 2 min, (2) 98° C. for 10 sec, (3) 62° C. for 5 sec, (4) 72° C. for 35 sec. Also, step (2) to (4) are repeated 25 cycles, then (5) 72° C. for 1 min. After all the steps are completed, the sample is stored at 10° C. As primers, both of T7omega_New having the sequence of SEQ ID NO: 20 and NewYtag for poly A cnvK having that of SEQ ID NO: 21 are used. The obtained PCR products are purified by using Agencourt AMPure XP, following instruction manual.

TABLE 23

| Composition | Content amount (µL) |
|---|---|
| 5 × PrimeSTAR Buffer | 10 |
| 2.5 mM dNTP Mixture | 4 |
| 10 mM T7omega_New | 1 |
| 10 mM NewYtag for poly A cnvK | 1 |
| Template DNA | 20 |
| 2.5 U/µL PrimeSTAR HS DNA polymerase | 0.5 |
| Nuclease free water (NFW) | 13.5 |

T7 omega New:
(SEQ ID NO: 20)
5'-GAT CCC GCG AAA TTA ATA CGA CTC ACT ATA GGG
GAA GTA TTT TTA CAA CAA TTA CCA ACA-3'

NewYtag for poly A crivK:
(SEQ ID NO: 21)
5'-TTT CCA CGC CGC CCC CCG TCC T-3'

(9) Production of FITC Beads

20 μL of Streptavidin (SA) magnetic beads (Dynabeads MyOne Streptavidin C1: Invitrogen) is added into the Eppendorf tube, and the tube is stood on the magnetic plate for 1 minute to remove the supernatant. Then, 100 μL of PBST is added to the tube to resuspend the beads. After 1-minute pipetting, the tube is stood on the magnetic plate for 1 minute to remove the supernatant.

Subsequently, 20 μL of HEPES buffer containing 20 mM HEPES and 100 mM NaCl is added to the tube to resuspend the beads. After that, 0.6 μL of NHS-Fluorescein solution, which is prepared by dissolving 1 mg of NHS-Fluorescein (5/6-carboxyfluorescein succinimidyl ester, ThermoFisher) into 100 μL of DMF, is added to the tube, and stirred at room temperature for 1 hour. The tube is stood on the magnetic plate to remove the supernatant. Subsequently, 100 μL of PBST is added to the tube and conducted 1-minute pipetting, and then the tube is stood on the magnetic plate for 1 minute to remove the supernatant. The procedure is repeated twice, and then 20 μL of PBST is added to obtain FITC beads solution.

(10) Sorting by Using FACS

2 μL of FITC beads prepared by following the procedures and 0.5 μL of HER2/ERBB2 immobilized beads are mixed in the tube so as to be the ratio at 4:1 in the bead amount, and the tube is stood on the magnetic plate for 1 minute for remove the supernatant. Then, 100 μL of PBST is added to the tube and resuspend the beads. After 1-minute pipetting, the tube is stood on the magnetic plate for 1 minute to remove the supernatant to prepare the beads for FACS sorting. 50 μL of the cDNA display solution (6 pmol), which is prepared from the PCR products obtained in (R4) is added to the obtained beads and stirred at room temperature for 30 minutes. Subsequently, the tube is stood on the magnetic plate for 2 minutes to remove the supernatant; and then 100 μL of PBST is added to the tube and pipetted for 1 minute, the tube is stood on the magnetic plate for 1 minute to remove the supernatant.

After repeating the procedure 3 times, 1 mL of PBST is added to the tube to prepare a sorting solution. The obtained sorting solution is set on FACS (Cell Sorter SH800: SONY), and a sample flow path, and droplet formation conditions at fractionation are setup; and then subjected to sort. Areas showing the magnetic beads are identified by their particle diameters, and then, the areas showing FITC beads or HER2/ERBB2 immobilized beads are identified by fluorescent intensities, when a laser light having 488 nm wavelength is irradiated. Subsequently, the beads are sorted under the maximal collection conditions to collect 500,000 particles in the Eppendorf tube, respectively. Then, the tube is centrifuged at 13,000×g for 10 minutes. After the centrifugation, the tube is stood on the magnetic plate for 10 minutes, and 40 μL of the elution buffer is added and shaken for 10 minutes. Then, the tube is stood on the magnetic plate for 2 minutes to collect the eluates. The obtained elutes are purified by using Agencourt AMPure XP, following the instruction manual attached.

(11) PCR Amplification of the Sample Separated with FACS

PCR is conducted by using PrimeSTAR HS DNA polymerase for amplifying DNA of samples. After the amplification, these samples are purified by using Agencourt AMPure XP, following the instruction manual attached.

(12) Conducting Amplicon Sequencing

In order to confirm convergences of the DNA library which are obtained by in vitro selection cycles and FACS sorting, the DNA sequences are analyzed by using a next generation sequencer (NGS). The samples for the sequencing are prepared according to a method for 2-step PCR Amplicon Library Preparation, which is provided by Illumina, Inc. Firstly, Amplicon PCR is conducted by employing PCR products obtained after each selection as templates, and the following Amplicon forward primer and Amplicon reverse primer, in the PCR reaction mixture having the composition shown in the following Table 24. PCR program is as follows: (1) 98° C. for 2 min, (2) 98° C. for 10 sec, (3) 62° C. for 5 sec, (4) 72° C. for 35 sec. Also, step (2) to (4) are repeated 15 cycles, then (5) 72° C. for 1 min. After all the steps are completed, the sample is stored at 10° C.

TABLE 24

| Composition | Content amount (μL) |
| --- | --- |
| Template DNA (5 ng/μL) | 2.5 |
| 10 mM Amplicon PCR Forward Primer | 0.5 |
| 10 mM Amplicon PCR Reverse Primer | 0.5 |
| 2 × KAPA HiFi HotStart Ready Mix | 12.5 |
| Nuclease free water (NFW) | 9 |

Amplicon PCR Forward Primer:
(SEQ ID NO: 22)
TCG TCG GCA GCG TCA GAT GTG TAT AAG AGA CAG NNN
NAT GGC TGA GGT GCA GCT CGT G Amplicon PCR Reverse Primer:
(SEQ ID NO: 23)
GTC TCG TGG GCT CGG AGA TGT GTA TAA GAG ACA GNN
NNT GAT GAT GAT GGC TAC CAC CTC CCG The obtained PCR products are purified by using Agencourt AMPure XP, following the instruction manual attached. Subsequently, purified samples are subjected to Index PCR, which is conducted by using the items listed in the following Table 25. The PCR program is as follows: at 98° C. for 1 minute; 10 cycles of at 98° C. for 10 seconds, at 55° C. for 5 seconds, and at 72° C. for 17 seconds; and then at 72° C. for 1 minute.

TABLE 25

| Listing of items used in Amplicon PCR | Content amount (μL) |
| --- | --- |
| Amplicon 1st PCR product | 5 |
| 10 mM Nextera XT Index 1 Primers (N7XX) (Illumina) | 1 |
| 10 mM Nextera XT Index 2 Primers (S5XX) (Illumina) | 1 |
| 2 × KAPA HiFi HotStart Ready Mix | 25 |
| Nuclease free water (NFW) | 18 |

The obtained PCR products are purified by using Agencourt AMPure XP, following the instruction manual attached. Subsequently, the purified PCR products are subjected to PAGE to confirm the size of the PCR products. After that, the concentration of PCR products are measured by using Nanodrop™, and the molar concentrations are calculated according to the following equation (1). On the basis of the measured concentrations, the PCR products in the solution are adjusted to 4 nM by adding NFW.

$$\text{DNA conc. [ng/µL]}/(660\text{ [g/mol]} \times 550\text{ [bp]}) \times 10^6 = \text{DNA conc. [nM]} \quad (1)$$

These samples are adjusted according to the recommended protocol for 4 nM library. Final concentration of the sample libraries is denatured or diluted, and then this sample is adjusted to 7 pM. Also, the percentage of PhiX control in a sample library has to be 5%. Subsequently, the prepared samples are subjected to sequence by using both of MiSeq (Illumina) and MiSeq Reagent Nano Kit v2 500 cycle (Illumina).

(13) Extraction of Amino Acid Sequences of the VHH Antibodies and Cluster Analysis of CDR3

Figure 25:
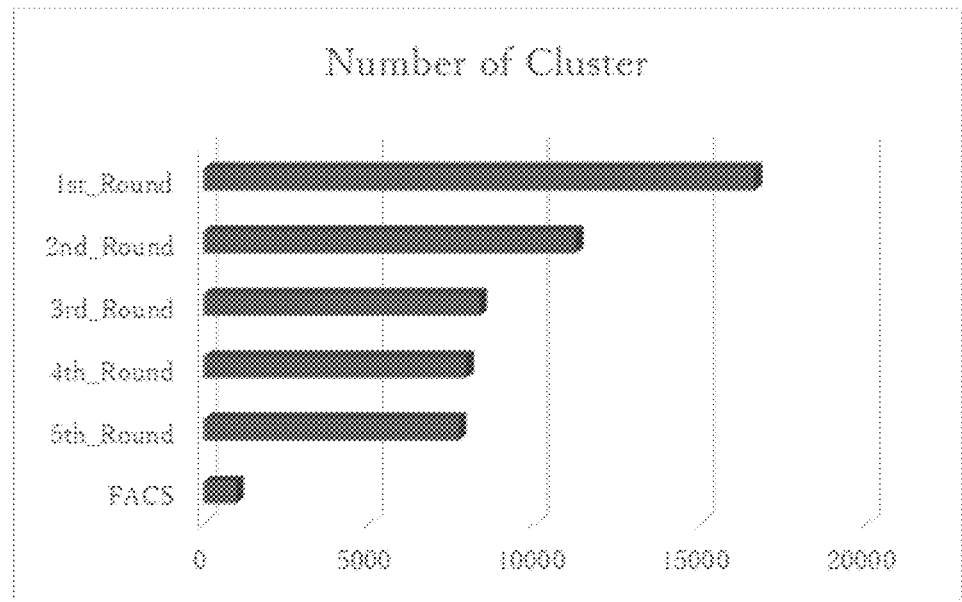
FIG. 25 shows the change of the cluster numbers in each round. Here, the same cluster is defined that it includes peptide sequences having the similarity not less than 80%.

Demultiplexed sequence data by using MiSeq Controller is subjected to data analysis. From the sequence data, VHH antibody coding nucleotide sequence regions are extracted to be translated to amino acid sequences. Subsequently, the number of the amino acid sequences, which have completely matched sequence to each amino acid sequence, are measured from the translated data. Then, one of the complementarity determining regions, CDR3 was used for determining the types of clusters. The sequences of CDR3 in the same cluster group should share more than 80% sequence identity. Then, the numbers of clones are counted in each cluster groups. Also, the number of cluster groups at each rounds of selections were counted. As a result, in R3 to R5, it is neither observed any decreasing of the number of cluster groups nor removal of non-specific adsorbents. Therefore, in these rounds, we could not confirm the clear improvement of the concentration ratio of the bound clones. On the other hand, the sample in R4 is subjected by FACS, we could confirm that the number of cluster groups was drastically decreased and the non-specific adsorbents were extremely efficiently removed (see FIG. 25).

We compared cluster groups which have frequently appeared sequences, and it is 1% of the total number of sequences. After comparison of the superior ranked sequences, the samples obtained in R5 were limited to only three types of sequences. In contrast, the samples obtained by FACS included sixteen types of sequences. In Table 26, top 10 sequences are shown.

According to this result, "cluster without condensation" is a mere group of the sequences which are not able to bind to the target. In contrast, the cluster with condensation by using FACS is the cluster to bind to the target, and FACS greatly contributed to select the cluster which are able to bind to the target. Furthermore, the analysis of the cluster which occupies not less than 1% of the entire cluster gave the result that many of this 1% of sequences have the specific binding activities, and it was demonstrated. Also, since we obtained many of the cluster which occupies not less than 1%, we could obtain the new variety of antibodies which bind to the target. These antibodies are called "hit antibodies".

TABLE 26

| The sequences of CDR 3 in the obtained clones frequently appeared | Cluster Nos. | Sequence of CDR3 | Conc. of the cluster (%) | SEQ ID NO. |
|---|---|---|---|---|
| FACS samples (Top 10 sequence frequently appeared) | 1 | LSGGRQY | 1.77 | 24 |
| | 2 | DPPLDY | 1.46 | 25 |
| | 3 | DTDWGTEGGY | 1.38 | 26 |
| | 4 | NLLHDDCDLGDMVF | 1.33 | 27 |
| | 5 | DDSLCRDYGRGMDS | 1.28 | 28 |
| | 6 | LPNRS | 1.23 | 29 |
| | 7 | SPDYRGGYYYTDEYDY | 1.22 | 30 |
| | 8 | LLGTRLY | 1.19 | 31 |
| | 9 | DTHWGYDS | 1.19 | 32 |
| | 10 | RARYLPADVILSPETAYDY | 1.18 | 33 |
| (R5) sample | 11 | ENGGFGYGQNF | 1.51 | 34 |
| | 12 | RHIVARYEY | 1.44 | 35 |
| | 13 | IRWGTSPDE | 1.32 | 36 |

(Example 8) Screening of Anti HSA (1) Immobilization of HSA on the Spherical Shaped Structure The spherical shaped structure has HSA (Fujifilm Wako Pure Chemical Corporation), the target molecule, on its surface. As the structure, Dynabeads MyOne Streptavidin C1, a supermagnetic polymer bead having 1.0 µm of the particle diameter with bound streptavidin, is employed. HSA is immobilized according to the following procedure.

Firstly, 100 µL of 1×PBS buffer is added to 10 mg HSA, and then 23 µL of 3.3 mM EZ-Link™ Sulfo-NHS-SS-Biotin solution is further added to the solution to prepare the reaction mixture, which is incubate at room temperature for 30 minutes. The reaction mixture is purified by using Zeba™ Spin Desalting Column (ThermoFisher), and 85 µL of Biotinylated Human Serum Albumin was collected.

150 µL of Dynabeads MyOne Streptavidin C1 is added into the Eppendorf tube, and the tube is stood on the magnetic plate for 1 minute to remove the supernatant. Subsequently, 100 µL of 1× Binding buffer containing 10 mM Tris-HCl, 1 M NaCl, 0.1% Tween 20, and 1 mM EDTA (pH 8) is added to the tube to resuspend the beads. After 1-minute pipetting, the tube is stood on the magnetic plate for 1 minute to remove the supernatant. 100 µL of 1 µM Biotinylated HSA solution is added to the tube to stir the beads at room temperature for 30 minutes. The tube is stood on the magnetic plate for 1 minute, and then the beads are washed with 200 µL of 1×PBS for 3 times, and then, 100 µL of PBS is added to the tube to obtain HSA immobilized beads. The protein concentrations of the solutions before and after the immobilization reaction are determined by using NanoDrop™ and their band intensity ratios on SDS-PAGE are compared to estimate yield of the immobilization reaction.

(2) In Vitro Selection

In vitro selection was carried out up to Rounds 1(R1) and 2(R2), according to the following procedure, wherein the cDNA-VHH conjugate, cDNA display molecule synthesized by the same procedure as shown in Example 7 and the spherical shaped structure having HSA on its surface prepared as described above.

The amount of mRNA/Linker ligation product for cDNA display synthesis are 192 pmol in R1, and 48 pmol in R2. In R2, in order to remove the non-specific adsorbents, the preselection is conducted (See, Table 27).

cDNA display molecule prepared as described above is diluted with PBST for preparing 100 µL of the diluted solution in the tube; they are bound to streptavidin binding magnetic beads, the negative beads, which are preliminary washed with 1× Binding buffer. After 12 hours stirring at 4° C., the tube is stood on the magnetic plate for 2 minutes to collect the supernatant, which are diluted with PBST to 1 µM in R1, and 100 nM in R2 against the immobilized HSA amount on the beads. Subsequently, the diluted supernatant containing cDNA display is bound to the HSA immobilized beads, the positive beads, in the tube and stirred at 4° C. for 12 hours.

The tube is stood on the magnetic plate for 2 minutes to remove the supernatant, and then the magnetic beads are washed with 200 µL of PBST. The washing procedure is repeated three times. Subsequently, 30 µL of 10 mM TCEP buffer (pH7 to 8) or 10 mM NaOH solution is added to the tube as the elution buffer, and the tube is incubated for 15 minutes to collect the eluates. The elution is conducted three times both in R1 and R2, and TCEP buffer is used for both in the $1^{st}$ and the $2^{nd}$ elution, and NaOH solution is used for solely the $3^{rd}$ elution.

TABLE 27

| Rounds | mRNA/Linker ligation product (cDNA display) | Preselection | Washing times |
|---|---|---|---|
| 1 | 192 pmol | none | 3 times |
| 2 | 48 pmol | 1 time | 3 times |

(3) Amplification of the Sample by Using PCR

The eluates obtained in the selection as described above are subjected to PCR, which is conducted under the same conditions shown in those of the Example 7 by using PrimeSTAR HS DNA Polymerase (Takara Bio Inc.).

(4) Screening by Using FACS

Biotin Fluorescein (Sigma-Aldrich) diluted to 10 µg/mL with PBST and 20 µL of the HSA immobilized beads solution prepared as described above (1) are mixed in the tube to stirred at room temperature for 30 minutes. Then, the tube is stood on the magnetic plate for 1 minute to remove the supernatant. 200 µL of PBST is added to the tube to conduct pipetting, and then the tube is stood on the magnetic plate for 1 minute to remove the supernatant. The procedure is repeated three times. Subsequently, 20 µL of PBST is added to the tube to prepare FITC modified HSA beads, the positive beads.

0.5 µL of FITC modified HSA beads, the positive beads, and 2 µL of streptavidin beads, the negative beads, are mixed. The cDNA display solution (6 pmol), which is prepared from the PCR products obtained in (R2) is added to the bead mixture, and diluted with PBST to 100 µL. The solution is stirred at room temperature for 1 hours, and then the tube is stood on the magnetic plate for 2 minutes to collect the supernatant. After that, 200 µL of PBST is added to the tube to wash the magnetic beads. The washing procedure is repeated three times. Subsequently, 1 mL of PBST is added to the tube and pipetted so as to sufficiently disperse the beads to prepare a sorting sample.

Obtained sorting samples are set to FACS (Cell Sorter SH800: SONY) for sorting. The area wherein the magnetic beads are existing are identified by the diameters of the beads used, and the areas wherein the positive beads or negative beads are identified on the basis of the fluorescence intensities obtained by irradiating laser light having the wavelength of 488 nm. Subsequently, the fractionation is collected in the fresh tube.

The collected samples are centrifuged by using the centrifuge (TOMY) at room temperature for 1 minute in 15,000 rpm (20,380×g). After that, the samples are stood on the magnetic plate for 2 minutes to remove the supernatant. As the elution buffer, 15 µL of 10 mM TCEP buffer (pH7 to 8) is added to the tube to incubate for 15 minutes to collect the eluates. The elution procedure is repeated twice.

(5) PCR Amplification of FACS Sorted Sample

According to the same procedure described in the example 7, PCR is conducted by using PrimeSTAR HS DNA Polymerase. The obtained PCR products are purified by using Agencourt AMPure XP, following the instruction manual thereof.

(6) Sequencing of the Amplicon

In order to confirm the convergence of the cDNA library which are obtained by the in vitro selection cycles and FACS sorting, the DNA sequences of DNA are analyzed by using NGS. The samples for sequencing are prepared by using the procedure described in the Example 7, according to the protocol of 2-step PCR Amplicon Library Preparation provided by Illumina.

(7) Extraction of Amino Acid Sequence of VHH Antibody and Sequence Analysis

Demultiplexed sequence data by using MiSeq Controller is subjected to data analysis. From the sequence data, VHH antibody coding nucleotide sequence regions are extracted to be translated to amino acid sequences. Subsequently, the number of the amino acid sequences, which have completely matched sequence to each amino acid sequence, are measured from the translated data. Then, one of the complementarity determining regions, CDR3 is used for determining the types of clusters. The sequences of CDR3 in the same cluster group should share more than 80% sequence identity. Then, the numbers of clones are counted in each cluster groups. As a result, for comparing the sequence appearance frequencies of the samples eluted from the beads, it was confirmed that the appearance frequencies of them in FACS screening are increasing from Round 2, and there are several clones showing higher sequence appearance frequencies in the positive beads than those of the negative beads. Particularly, among them, both of Clone A and B showed excellent frequency ratios, FP/N, between the positive beads and the negative beads, 13.7 and 9.3, respectively (Table 28).

TABLE 28

| | NGS sequence appearance frequency | | | | |
|---|---|---|---|---|---|
| | frequency | frequency FACS (%) | | frequency ratio | |
| | Round 2 (R2) | P(FP) | N(FN) | (FP/R2) | (FP/FN) |
| Clone A | 0.48% | 2.28 | 0.166 | 4.75 | 13.7 |
| Clone B | 0.095% | 0.62 | 0.067 | 6.53 | 9.3 |

(8) Construction of the Plasmid for VHH Expression Library

In order to express proteins both of VHH clones A and B, which are chosen from the VHH clones on the basis of NGS analysis, the genes of the VHH clones A and B are separately introduced into the expression plasmid. Both of the genes from the VHH clones and the expression plasmid without any external genes are treated with two restriction enzymes, Sfi I (Thermo Fisher) and Not I (Thermo Fisher); and then, fragment DNAs of the interest are solely chosen and purified by using the conventional method. Subsequently, the VHH clone genes treated with the restriction enzymes and the expression plasmid are ligated by using Ligation Mix (Toyobo). The obtained ligation products are used to transform a competent cell for cloning, JM109 (E. coli). The plasmid is extracted from transformed E. coli to obtain the expression plasmid for the VHH clones A and B.

(9) Preparation of a Recombinant Corynebacterium glutamicum Strain

The obtained plasmid is introduced by using the following electroporation method into Corynebacterium glutamicum strain. Firstly, Corynebacterium glutamicum strain (glycerol stock) is inoculated into CM2G liquid medium, and conducted to shaking culture at 30° C., 160 rpm and for several hours, and the culture medium is collected to a microtube. Subsequently, the tube is centrifuged by using the centrifuge (TAITEC) with 15,000 rpm (20,380×g), for 1 minute to remove the supernatant, and then the pellet is resuspended with the sterilized water. The suspended cells are washed with the sterilized water once, and they are again resuspended by using 100 µL of the sterilized water. The obtained suspension is mixed with each VHH expression plasmid, and they are subjected to the electroporation.

The suspended cells are washed with the sterilized water once, and they are again resuspended by using 100 µL of the sterilized water. The obtained suspension is mixed with each VHH expression plasmid, and they are subjected to the electroporation. 1 mL of CM2G medium is added to the suspension in the tube, and then, the tube is subjected to shaking culture at 30° C., 180 rpm for 1 hour. After that, the cultivate is streaked on a CM2G agar plate containing 25 µg/mL of kanamycin in proper volume, and then incubated at 30° C. for 1 to 2 days to obtain the recombinant Corynebacterium glutamicum strain.

(10) VHH Production

The recombinant Corynebacterium glutamicum strain obtained in the above (9) is inoculated in CM2G medium containing 25 µg/mL of kanamycin, and conducted preculture at 30° C. for overnight shaking to obtain preculture medium. Entire of the medium is inoculated to PM1S medium so as to become 5% (v/v), and then the medium is subjected to the shaking culture at 25° C. for 72 hours. After the termination of the culture, the cultivate is centrifuged with the centrifuge (Thermo Fisher Scientific) by 4,100 rpm (4,000×g), at 4° C. for 30 minutes to collect the supernatant.

Figure 26:
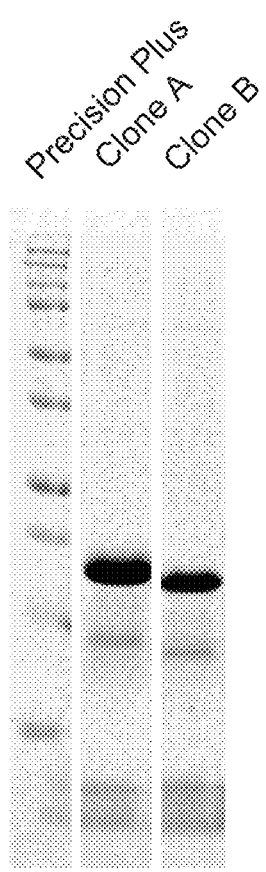
FIG. 26 is a SDS-PAGE image showing results of VHH production by a recombinant *Corynebacterium glutamicum* strain, which expresses genes of Clone A or Clone B. Precision Plus represents a molecular weight marker.

In order to confirm the production of VHH in supernatant of each culture medium, they are subjected to SDS-PAGE under the following conditions: four L of the supernatant as the sample is applied in each well, PAGE is conducted at 150 V for 1 hour. As the molecular weight marker, Precision Plus Protein™ Standards (BIO-RAD) is used. As a result, it was confirmed that both of VHH from the clone A and B were produced in the supernatant of the culture (FIG. 26).

INDUSTRIAL APPLICABILITY

The present invention is useful in the field of pharmaceuticals, particularly, in the field of diagnostic reagents.

Free Text of Sequence Listing

SEQ. ID NO. 1: Nucleotide sequence of a backbone of a photo-crosslinking type linker
SEQ. ID NO. 2: The nucleotide sequence of a side chain of the photo-crosslinking type linker
SEQ. ID NO. 3: The nucleotide sequence of DNA fragment for DNA library synthesis
SEQ. ID NO. 4: The nucleotide sequence of DNA fragment for DNA library synthesis
SEQ. ID NO. 5: The nucleotide sequence of DNA fragment for DNA library synthesis
SEQ. ID NO. 6: A forward primer for PCR
SEQ. ID NO. 7: A reverse primer for PCR
SEQ. ID NO. 8: Amino acid sequence obtained from designed DNA
SEQ. ID NO. 9: The amino acid sequence of LB-1 peptide
SEQ. ID NO. 10: 5' primer for DNA synthesis of SA binding RNA aptamer
SEQ. ID NO. 11: 3' primer for DNA synthesis of RNA aptamer
SEQ. ID NO. 12: 5' primer for DNA synthesis of RNA-nonbinding RNA aptamer
SEQ. ID NO. 13: T7 primer for PCR
SEQ. ID NO. 14: Backbone of the linker shown in FIG. 9
SEQ. ID NO. 15: Backbone of the linker shown in FIG. 8
SEQ. ID NO. 16: VHH specific 5' primer
SEQ. ID NO. 17: VHH specific 3' primer
SEQ. ID NO. 18: 5' primer for overlap PCR
SEQ. ID NO. 19: 3' primer for overlap PCR
SEQ. ID NO. 20: T7omega_New primer
SEQ. ID NO. 21: NewYtag for poly A cnvK primer
SEQ. ID NO. 22: Amplicon PCR Forward Primer
SEQ. ID NO. 23: Amplicon PCR Reverse Primer
SEQ. ID NO. 24: FACS samples (Top 10 sequence frequently appeared)
SEQ. ID NO. 25: FACS samples (Top 10 sequence frequently appeared)
SEQ. ID NO. 26: FACS samples (Top 10 sequence frequently appeared)
SEQ. ID NO. 27: FACS samples (Top 10 sequence frequently appeared)
SEQ. ID NO. 28: FACS samples (Top 10 sequence frequently appeared)
SEQ. ID NO. 29: FACS samples (Top 10 sequence frequently appeared)
SEQ. ID NO. 30: FACS samples (Top 10 sequence frequently appeared)
SEQ. ID NO. 31: FACS samples (Top 10 sequence frequently appeared)
SEQ. ID NO. 32: FACS samples (Top 10 sequence frequently appeared)
SEQ. ID NO. 33: FACS samples (Top 10 sequence frequently appeared)
SEQ. ID NO. 34: (R5) sample
SEQ. ID NO. 35: (R5) sample
SEQ. ID NO. 36: (R5) sample
SEQ. ID NO. 37: Amino acid sequence of CDR3 included in Clone A
SEQ. ID NO. 38: Amino acid sequence of CDR3 included in Clone B
SEQ. ID NO. 39: mRNA sequence of FIG. 8
SEQ. ID NO. 40: mRNA sequence of FIG. 9

What is claimed is:

1. A method of identifying antibody CDR3 clusters using high speed in vitro screening of a library selected from the group consisting of a cDNA library and a nucleic acid aptamer library comprising:
   (i) preparing a positive spherical shaped structure by binding a target molecule to a spherical shaped molecule, wherein the target molecule is immobilized on the positive spherical shaped structure, wherein the positive spherical shaped structure may contain a fluorescent label;
   (ii) preparing a negative spherical shaped structure, wherein the target molecule is not immobilized on the negative spherical shaped structure, wherein the negative spherical shaped structure may contain a fluorescent label;
   (iii) forming a positive spherical shaped conjugate or a negative spherical shaped conjugate by binding a target detecting molecule capable of binding to the target molecule to the positive spherical shaped structure or to the negative spherical structure, wherein the target detecting molecule is selected from the library having a size equal to or more than $10^{10}$ or equal to or less than $10^{14}$, wherein the target detecting molecule may contain a fluorescent label;
   (iv) separating the positive and the negative spherical shaped conjugates using a fluorescence cell sorter;
   (v) selecting the separated positive and the separated negative spherical shaped conjugates at least 1 time and then eluting the selected conjugates to obtain an eluted sample;
   (vi) amplifying a nucleic acid in the eluted sample using PCR to obtain PCR products;
   (vii) separating the PCR products using the fluorescence cell sorter; and
   (viii) conducting amplicon sequencing for CDR3 cluster analysis to identify the antibody CDR3 clusters.

2. The method of identifying antibody CDR3 clusters using the high speed in vitro screening according to the claim 1, wherein the spherical shaped structure is selected from the group consisting of: a liposome, a Sepharose bead, a silica bead and a latex bead; or is selected from the group consisting of: a liposome-coated Sepharose bead, a liposome-coated silica bead, and a liposome-coated latex bead.

3. The method of identifying antibody CDR3 clusters using the high speed in vitro screening according to the claim 2, wherein the spherical shaped structure has a diameter between 0.5 μm to 20 μm.

4. The method of identifying antibody CDR3 clusters using the high speed in vitro screening according to the claim 1, wherein the target detecting molecule is either a nucleic acid-linker conjugate obtained from the cDNA library using a cDNA display method or a nucleic acid aptamer obtained from the nucleic acid-linker conjugate.

5. The method of identifying antibody CDR3 clusters using the high speed in vitro screening according to the claim 1, wherein the target detecting molecule is directly bound to the surface of the spherical shaped structure via a functional group, or bound to it via the target molecule which is immobilized on the surface of the spherical structure.

6. The method of identifying antibody CDR3 clusters using the high speed in vitro screening according to the claim 5, wherein the functional group is selected from the group consisting of: a carboxyl group, an amino group, a hydroxyl group, and a thiol group.

7. The method of identifying antibody CDR3 clusters using the high speed in vitro screening according to the claim 5, wherein the target molecule is selected from the group consisting of: a biotin, a streptavidin, an azide obtained using click chemistry, and a N-hydroxysuccinimide ester (NHS).

8. The method of identifying antibody CDR3 clusters using the high speed in vitro screening according to the claim 1, wherein the antibody CDR3 cluster of VHH contains at least 10 different peptide sequences.

9. The method of obtaining antibody CDR3 clusters using the high speed in vitro screening according to the claim 8, wherein the CDR3 cluster of VHH having at least 10 different peptide sequences is selected from the group consisting of SEQ ID NOS: 24 to 33.

* * * * *